(12) United States Patent
Hauptman et al.

(10) Patent No.: US 12,239,469 B2
(45) Date of Patent: Mar. 4, 2025

(54) ANALYTE DATA PROCESSING, REPORTING, AND VISUALIZATION

(71) Applicant: Dexcom, Inc., San Diego, CA (US)

(72) Inventors: Alexis P. Hauptman, Portland, OR (US); Douglas Scott Kanter, San Diego, CA (US); Janna Caryn Kimel, Portland, OR (US); Lee Anne Marie Mojica Mercado, Eastvale, CA (US); Sonya Ann Sokolash, Portland, OR (US); Travis Kroeker, Rockville, MD (US)

(73) Assignee: Dexcom, Inc., San Diego, CA (US)

( * ) Notice: Subject to any disclaimer, the term of this patent is extended or adjusted under 35 U.S.C. 154(b) by 269 days.

(21) Appl. No.: 17/652,273

(22) Filed: Feb. 23, 2022

(65) Prior Publication Data

US 2022/0265224 A1  Aug. 25, 2022

Related U.S. Application Data

(60) Provisional application No. 63/153,524, filed on Feb. 25, 2021.

(51) Int. Cl.
| | |
|---|---|
| G16H 15/00 | (2018.01) |
| A61B 5/00 | (2006.01) |
| A61B 5/145 | (2006.01) |
| G06F 16/907 | (2019.01) |

(52) U.S. Cl.
CPC ........ *A61B 5/7475* (2013.01); *A61B 5/14546* (2013.01); *A61B 5/742* (2013.01); *G06F 16/907* (2019.01); *G16H 15/00* (2018.01); *G06F 2203/04803* (2013.01)

(58) Field of Classification Search
None
See application file for complete search history.

(56) References Cited

U.S. PATENT DOCUMENTS

| | | | |
|---|---|---|---|
| 7,900,186 B2* | 3/2011 | Lucassen .................. | G06F 8/38 717/104 |
| 10,854,337 B2 | 12/2020 | McRaith et al. | |
| 11,666,702 B2* | 6/2023 | Morawiec ............. | G06T 11/206 705/2 |
| 2002/0178185 A1* | 11/2002 | Kuchinsky .............. | G06F 16/21 715/201 |
| 2004/0078378 A1* | 4/2004 | Bala ........................ | G06F 16/26 |
| 2004/0201588 A1* | 10/2004 | Meanor ................. | G06T 11/206 345/440 |
| 2007/0016449 A1* | 1/2007 | Cohen .................... | G16H 15/00 128/898 |

(Continued)

OTHER PUBLICATIONS

Medtronic MiniMed, Inc., "CareLink Pro User Guide," 2010, https://www.medtronicdiabetes.com/sites/default/files/library/download-library/user-guides/carelink-v3_0/en_carelink_pro_user_guide.pdf.*

(Continued)

*Primary Examiner* — Ryan Barrett
(74) *Attorney, Agent, or Firm* — Patterson + Sheridan, LLP

(57) ABSTRACT

Certain aspects of the present disclosure provide techniques for processing and presenting analyte data. Some example aspects may describe techniques for generating and providing a user interface view of a user's performance report for display. Some example aspects may describe techniques for providing one or more user interface views for display on one or more widgets.

20 Claims, 89 Drawing Sheets

(56) References Cited

U.S. PATENT DOCUMENTS

| | | | |
|---|---|---|---|
| 2009/0192745 A1* | 7/2009 | Kamath | A61B 5/14532 702/85 |
| 2009/0228253 A1* | 9/2009 | Tolone | G06Q 10/10 703/6 |
| 2011/0004085 A1* | 1/2011 | Mensinger | A61B 5/7275 600/365 |
| 2011/0201911 A1* | 8/2011 | Johnson | G16H 40/67 345/173 |
| 2012/0023421 A1* | 1/2012 | Demant | G06F 9/452 715/765 |
| 2012/0066092 A1* | 3/2012 | Swinson | G06Q 30/0613 705/26.41 |
| 2013/0035871 A1* | 2/2013 | Mayou | G16H 50/20 702/26 |
| 2013/0196616 A1* | 8/2013 | Zalmanovitch | H04M 15/854 455/405 |
| 2015/0289823 A1* | 10/2015 | Rack-Gomer | A61B 5/7282 600/365 |
| 2015/0355790 A1* | 12/2015 | O'Mahony | G06F 3/04842 715/771 |
| 2016/0098848 A1* | 4/2016 | Zamanakos | A61B 5/7275 345/440 |
| 2016/0328991 A1* | 11/2016 | Simpson | G09B 19/0092 |
| 2017/0049386 A1* | 2/2017 | Abraham | A61M 5/1723 |
| 2017/0116380 A1* | 4/2017 | Wiedeback | H04L 63/083 |
| 2018/0228408 A1* | 8/2018 | Raisoni | A61B 5/14532 |
| 2019/0053765 A1 | 2/2019 | Budiman et al. | |
| 2019/0252079 A1* | 8/2019 | Constantin | A61B 5/7275 |
| 2019/0320976 A1* | 10/2019 | Roslin | G16H 20/60 |
| 2021/0014710 A1* | 1/2021 | Raju | H04W 4/38 |
| 2021/0030323 A1* | 2/2021 | Hayter | A61B 5/14532 |
| 2021/0177360 A1* | 6/2021 | Montgomery | G16H 40/60 |
| 2022/0051797 A1* | 2/2022 | Saleh | G16H 50/20 |
| 2023/0329647 A1* | 10/2023 | Armada | G09G 5/14 |

OTHER PUBLICATIONS

Ascensia Diabetes Care US Inc., "Contour Diabetes app User Guide," Jan. 23, 2020, https://web.archive.org/web/20200123033159/ https://www.contournextone.com/siteassets/pdf/90001318_cntr_diabetes_app_gde_usr_usen_web.pdf.*

Anonymous, "Dexcom Clarity," Jan. 1, 2018, Retrieved from the Internet: URL: https://s3-us-west-2.amazonaws.com/dexcompdf/ Dexcom_Clarity_User_Guide_Home_User.pdf, Retrieved on [May 31, 2022], pp. 1-28.

Anonymous, "Patient Guide to Reports," Jan. 1, 2020, Retrieved from the Internet: URL: https://uk.provider.dexcom.com/sites/g/files/rrchkb126/files/document/2021-09/LBL018585%20Rev002%20Dexcom%20CLARITY%20Patient%20Guide%20to%20Reports%20OUS%20English%20mmol%20(2).pdf, Retrieved on [May 31, 2022], pp. 1-8.

International Search Report and Written Opinion for Application No. PCT/US2022/070802 mailed Jun. 10, 2022, 17 pages.

Miriam L., et al., "Glycemic Control in People with Type 1 Diabetes using a Hybrid Closed Loop System and Followed by Telemedicine During the COVID-19 Pandemic in Italy," Diabetes Research and Clinical Practice, Amsterdam, Sep. 12, 2020, vol. 169, XP086390554, ISSN: 0168-8227, DOI: 10.1016/J.DIABRES.2020.108440, pp. 1-8.

Robert A. V., et al., "The Comprehensive Glucose Pentagon: A Glucose-Centric Composite Metric for Assessing Glycemic Control in Persons With Diabetes," Journal of Diabetes Science and Technology Diabetes Technology Society Reprints and Permissions, Jul. 27, 2017, vol. 12, No. 1, pp. 114-123, XP055926924, DOI: 10.1177/193229681771856, Retrieved from the Internet: URL: https://journals.sagepub.com/doi/pdf/10.1177/1932296817718561.

* cited by examiner

500

Weekly Report Nov 8, 2019 - Nov 21, 2019

ıhı Dexcom

Time in Range

0% Very High
38% High
56% In Range
4% Low
2% Very Low

Decrease since last week: -7%

Target Range:
Day (6:00 AM - 10:00 PM) 80 - 180 mg/dL
Night (10:00 PM - 6 AM) 90 - 200 mg/dL

Average Glucose
156 mg/dL

Standard Deviation
49 mg/dL

Patterns

Daytime Lows
You had a pattern of significant lows between 6:05am and 7:55am. 2 low events contributed to this pattern. None of the contributing events were rebound lows.

Nighttime Highs
You had a pattern of significant highs between 10:05pm and 11:55pm. 2 high events contributed to this pattern. None of the contributing events were rebound highs.

Trends

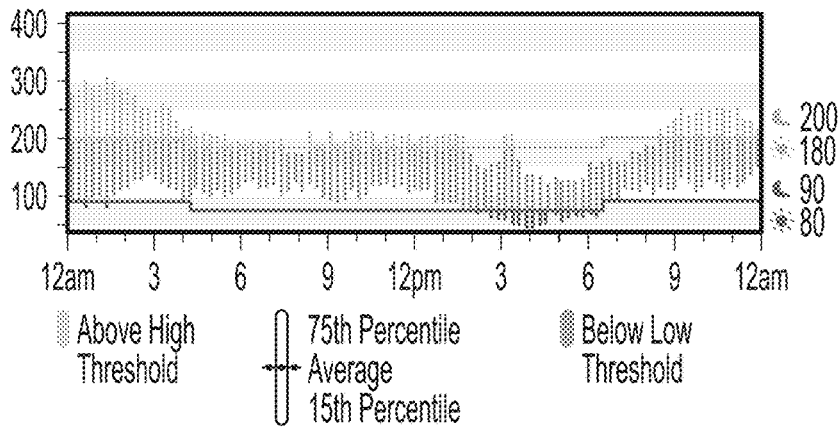

Visit Dexcom on the web for all your CGM glucose reports.
Your signed up for this Dexcom Weekly Summary with the Dexcom app. Unsubscribe.

FIG. 5

800e
Patterns
1 Nighttime Lows
You had a pattern of significant lows between # am/pm and # am/pm. # low events contributed to this pattern. ## of the contributing events were rebound lows.
2 Daytime Highs
You had a pattern of significant highs between # am/pm and # am/pm. # high events contributed to this pattern. ## of the contributing events were rebound highs.
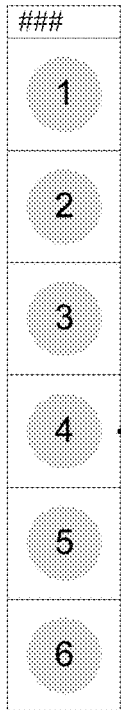
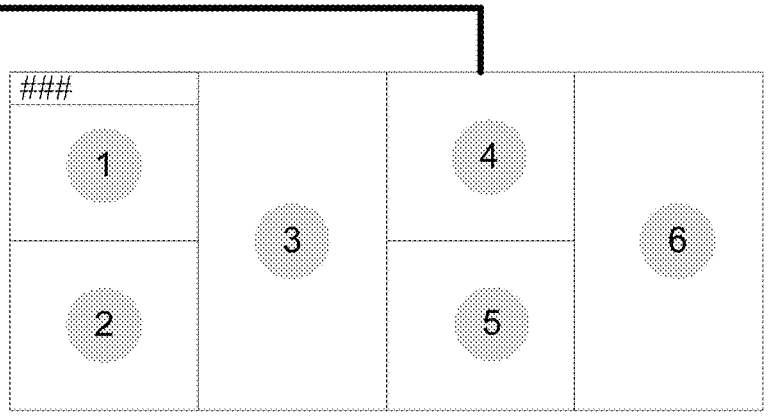
FIG. 8E 800g To view all your CGM glucose reports, visit the # # # app.

GO TO ###

This email was sent # # #

You are receiving it because you signed up for # # # weekly Email Reports.   Click here to unsubscribe.

IMPORTANT NOTICE: This email, including any attachments, may contain information that is confidential and/or privileged. If you are not the intended recipient, your use, disclosure, copying, or distribution of this email is unauthorized and strictly prohibited. Please notify us immediately and delete this email if you learn or have reason to believe that you received it in error. Nothing in this email constitutes a binding signature, offer, acceptance or contract # # # unless expressly so stated in this email.

Emails, including any attachments, sent to and from this address will be received or otherwise recorded by # # #, and are subject to archival, monitoring and review by # # # and/or disclosure to third parties as may be necessary or required by law.

FIG. 8G

Patterns

① Nighttime Lows

You had a pattern of significant lows between 5:05am and 6:55am. 2 low events contributed to this pattern. None of the contributing events were rebound lows.

② Daytime Highs

You had a pattern of significant highs between 8:50am and 3:40pm. 4 high events contributed to this pattern. Two of the contributing events were rebound highs.

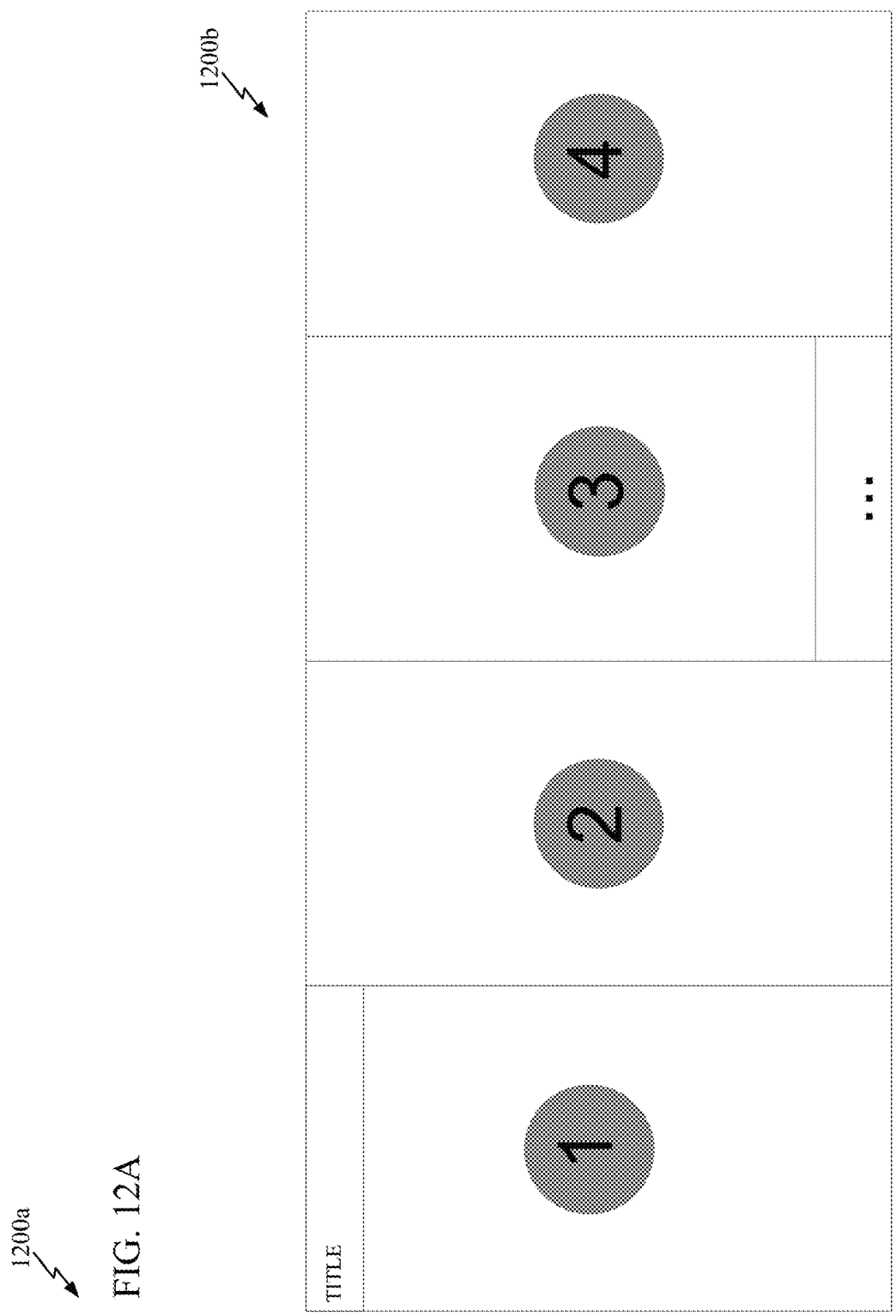
FIG. 12A
FIG. 12B
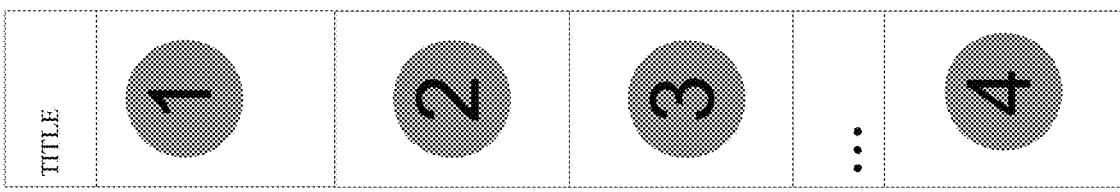

FIG. 12G

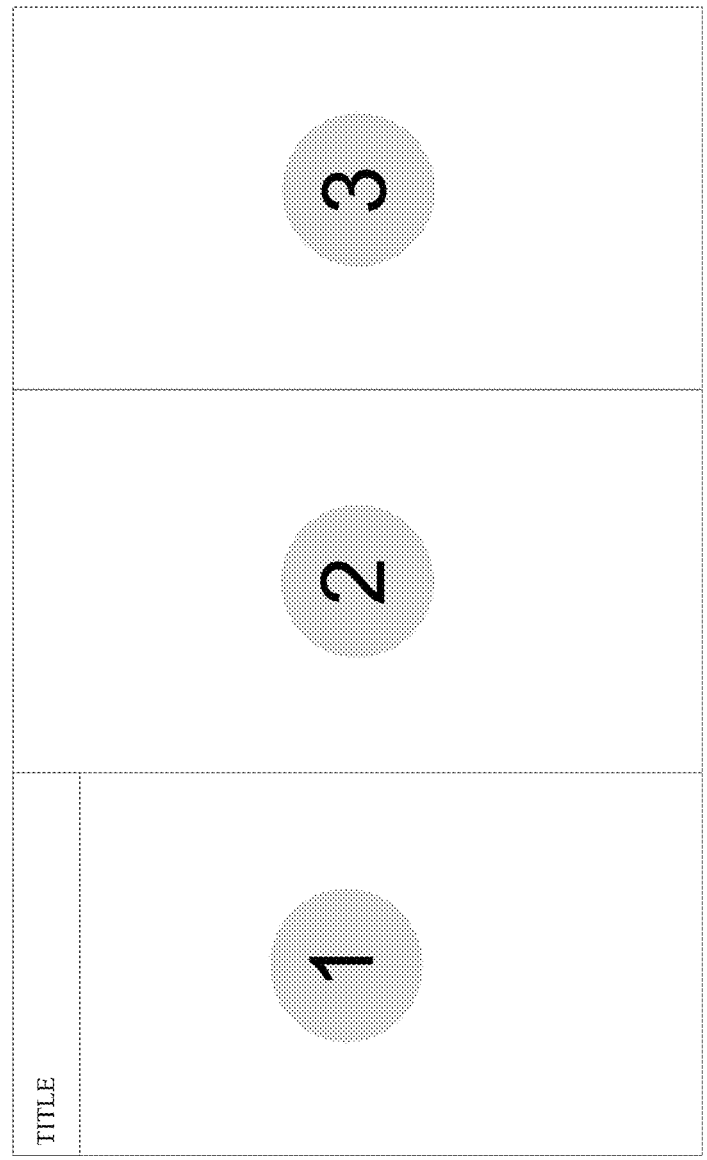
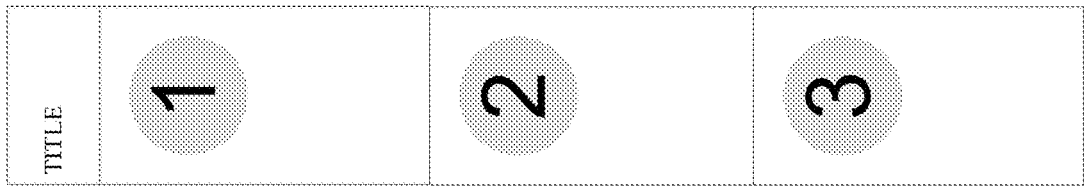
FIG. 13A
FIG. 13B

| | Example Widget Types | Fig. |
|---|---|---|
| Summary Type Widgets | Summary of the host's percentage of time spent in a target glucose range and the host's average glucose over 7 days | 19 |
| | Summary of the host's average glucose, the host's standard deviation, and the host's glucose management indicator (GMI) percentage over 14 days | 20 |
| | Summary of the host's percentage of time spent in a target glucose range, the host's average glucose, and the host's standard deviation over 14 days | 21 |
| | Summary of the host's percentage of time spent in a target glucose range, the host's average glucose, and the host's GMI percentage over 14 days | 22 |
| | Summary of the host's percentage of time spent in a target glucose range, very high and high glucose ranges, and very low and low glucose ranges over 14 days | 23 |
| | Summary of the host's percentage of time spent in a target glucose range, very high and high glucose ranges, and very low and low glucose ranges over 14 days plus an indication of the positive or negative percentage of change compared to the prior 14 days | 24 |
| | Summary of the host's percentage of time spent in a target glucose range, very high and high glucose ranges, and very low and low glucose ranges over 14 days, the host's average glucose, and the host's GMI percentage over 14 days | 25A-B |
| | Summary of the host's percentage of time spent in a target glucose range, very high & high glucose ranges, and very low & low glucose ranges over 30 days plus an indication of the positive or negative percentage of change compared to the prior 30 days, the host's avg. glucose, the host's GMI percentage, and an indication of a pattern (e.g., host's daytime high or nighttime low glucose patterns) over 30 days | 26A-B |
| | Summary of the host's percentage of time spent in a target glucose range comparing the current week, last week, this month, and year to date (YTD) percentages | 27 |
| | Summary of the host's percentage of time spent in a target glucose range comparing the last 7 days, the last 14 days, and the last 30 days plus an indication of the host's average glucose and standard deviation over the last 7 days, the last 14 days, and the last 30 days | 28 |
| | Summary of the host's percentage of time spent in a target glucose range, very high and high glucose ranges, and very low and low glucose ranges and an indication of the hours/minutes the host spent in each of these ranges over 7 days | 29 |
| | Summary of the hours/minutes host spent in a target glucose range, a high glucose range, and a low glucose range over 7 days | 30 |
| | Summary of the number of high and low events the host participated in over 7 days | 31 |
| | Summary of the host's time in range may be presented in a graph with a line of best fit indicating the host's time in range trend over a twelve hour period (e.g., 12:00 AM – 12:00 AM) for 3 days and an indication of the data included in the summary graph | 32 |

FIG. 18A
1800A

| | Example Widget Types | Fig. |
|---|---|---|
| Motivation Type Widgets | Horizontal bar graph illustrating the host's percentage of time spent in a target glucose range per day for a 7 day period compared to a goal percentage of time to be spent in the target glucose range per day | 33A-E |
| | Vertical bar graph illustrating the host's percentage of time spent in a target glucose range per day for a 7 day period compared to a goal percentage of time to be spent in the target glucose range per day | 34 |
| | Vertical bar graph illustrating the host's percentage of time spent in a target glucose range for today compared to a goal percentage of time to be spent in the target glucose range per day | 35A-B |
| | Horizontal bar illustrating a number of hours the host spent in a target glucose range today compared to a goal number of hours to be spent in the target glucose range per day | 36 |
| | Indication of the host's best day over the past 7 days with a summary of the host's average glucose, the host's percentage of time spent in a target glucose range, and the host's standard deviation for that day | 37 |
| | Indication of the host's best day over the past 7 days with a summary of the host's average glucose and the host's percentage of time spent in a target glucose range for that day | 38 |
| | Indication of the host's best day over the past 7 days with a summary of the host's average glucose, the host's standard deviation, and the host's percentage of time spent in a target glucose range for that day plus an indication of the host's percentage of time spent in a target glucose range for the host's second best day and third best day | 39 |
| | Comparison of the host's best day, average day, and trouble day for the past week with a summary of the host's average glucose, the host's standard deviation, and the host's percentage of time spent in a target glucose range for each of those days | 40 |
| | Comparison of the host's best day, average day, and trouble day for the past 7 days with a summary of the host's average glucose and the host's percentage of time spent in a target glucose range for each of those days | 41 |
| | Comparison of the host's percentage of time spent in a target glucose range for the last 4 weeks plus comparison to a goal percentage of time to be spent in the target glucose range per day | 42 |
| | Number of continuous days the host has spent in a target glucose range with a notification to lower or increase the target glucose range | 43 |

FIG. 18B
1800B

| | Example Widget Types | Fig. |
|---|---|---|
| Event Type Widgets | Summary of the host's glucose level at the start of each logged event and 2 hours after the start of the logged event | 44 |
| | Indication of the host's glucose level at the start of each logged event and a trend of fluctuations in the host's glucose level following each event logged (e.g., 1 hour after logged event, 2 hours after logged event, 3 hours after logged event, etc.) | 45 |
| | Summary of the host's glucose level per event per day at the start of each logged event, 1 hour after the start of the logged event, and 2 hours after the start of the logged event | 46 |
| | Trend of the host's glucose levels, insulin units, carbs logged, steps logged, and sleep logged over the past 24 hours | 47A-B |
| | Day-by-day bar graph illustrating the host's percentage of time spent in a target glucose range per day for a 7 day period and an average number of carbs consumed per day | 48 |
| | Bar graph illustrating the host's average steps and average glucose per day | 49 |
| | Day-by-day bar graph illustrating the host's average steps and average glucose per day | 50 |
| | Scatter plot illustrating the host's average steps and average glucose per day | 51 |
| Other Type Widgets | Summary of the host's average glucose for each day of the week over the last 30 days (or last week) compared to a goal average glucose per day | 52 |
| | Trend of the host's average glucose levels for a 24 hour period over the last 14 days | 53A-B |
| | Trends of best hours in a 24 hour day, over a 14 day period, where the host has the highest percentage of time spent in the target glucose range plus a notification on how much time the host must stay in the target glucose range to reach a goal percentage of time in range | 54 |
| | Summary of the host's percentage of time spent in a target glucose range, very high and high glucose ranges, and very low and low glucose ranges over 14 days, the host's average glucose over 14 days, and the host's GMI percentage over 14 days plus a trend of the host's average glucose levels over the last 14 days | 55 |

| | Glucose mg/dL | At Event | + 1 hr | + 2 hr |
|---|---|---|---|---|
| Aug 9th | Ev time | ## | ## | ## |
| Yesterday | Ev time | ## | ## | ## |
| | Ev time | ## | ## | ## |
| Today | Ev time | ## | ## | ## |
| | Ev time | ## | ## | ## |
| | Ev time | ## | ## | ## |

ANALYTE DATA PROCESSING, REPORTING, AND VISUALIZATION

CROSS-REFERENCE TO RELATED APPLICATION(S)

This application claims priority to U.S. Provisional Application No. 63/153,524 filed Feb. 25, 2021, which is hereby assigned to the assignee hereof and hereby expressly incorporated by reference herein in its entirety as if fully set forth below and for all applicable purposes BACKGROUND

FIELD OF THE DISCLOSURE

Aspects of the present disclosure generally relate to continuous analyte monitoring and, more specifically, to analyte data processing, reporting, and visualization.

DESCRIPTION OF RELATED ART

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take a timely SMBG measurement and, consequently, may be unaware whether his or her blood glucose value is indicative of a dangerous situation.

A variety of non-invasive, transdermal (e.g., transcutaneous) and/or implantable electrochemical sensors are being developed for detecting and/or quantifying blood glucose values. These devices generally transmit raw or minimally processed data for subsequent analysis at a remote device. The remote device may have a display that presents information to a user hosting the sensor. In some systems, a patient may check his or her glucose level on a hand held computing device. There are challenges to presenting this information discreetly and reliably. Moreover, there are challenges to efficiently analyze this information such that reports and insights may be presented to the diabetic user for continuous management of the diabetic condition.

SUMMARY

The systems, methods, and devices of the disclosure each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features of this disclosure provide advantages that include improved analysis and presentation of analyte data.

Methods, means for, apparatus, processors and/or processing systems, and computer-readable mediums and/or computer program products, are provided for processing and visualization of analyte data.

Certain aspects of the present disclosure provide a method for generating a user interface view associated with sensor data representative of a glucose concentration level in a host. The method may include accessing sensor data, where the sensor data may include a plurality of blood glucose readings associated with the host during a plurality of analysis time periods in a current week. Each blood glucose reading may be indicative of a blood glucose concentration level of the host at a respective time. The method may include determining an average blood glucose concentration level of the host for the current week based on the plurality of blood glucose readings. The method may include generating a performance report. The performance report may include, but is not limited to including, the average blood glucose concentration level of the host for a first time period and a comparison of the average blood glucose concentration level of the host for the first time period to average blood glucose concentration levels of the host for at least two previous time periods of similar duration, a per-day average blood glucose concentration level of the host, per-day percentages of blood glucose concentration level of the host at one or more blood glucose concentration level ranges, or a combination thereof. The information in the report may be customizable by the user. The method may include generating a user interface view of the performance report. The method may include providing the user interface view of the performance report for display.

Certain aspects of the present disclosure provide a method for generating a user interface view associated with sensor data representative of a glucose concentration level in a host. The method may include accessing first data associated with blood glucose concentration level of a host, the first data associated being with a first time period. The method may include analyzing the first data to generate a first one or more user interface views associated with the first data for display on one or more widgets. The method may include providing the first one or more user interface views for display on the one or more widgets. The method may include automatically updating the first one or more user interface views for display on the one or more widgets. Automatically updating the first one or more user interface views may include accessing second data associated with blood glucose concentration level of the host, the second data being associated with a second time period, analyzing the second data to generate a second one or more user interface views associated with the second data for display on the one or more widgets, and providing the second one or more user interface views for display on the one or more widgets. The one or more widgets may be customizable by the user.

It is to be understood that both the foregoing general description and the following detailed description are example and explanatory only and are not restrictive. Further features and/or variations may be provided in addition to those set forth herein. For example, the aspects described herein may be directed to various combinations and subcombinations of the disclosed features and/or combinations and subcombinations of several further features disclosed below in the detailed description.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the drawings. It is to be noted, however, that the appended drawings illustrate only certain typical aspects of this disclosure and are therefore not to be considered limiting of its scope, for the description may admit to other equally effective aspects.

FIG. 5 illustrates an example user interface view associated with sensor data representative of glucose concentration level(s) in a host, in accordance with some example aspects of the present disclosure.

FIGS. 8B-8G illustrate enlarged views of features one through six shown in the vertical and horizontal wireframes of FIG. 7 and FIG. 8A, respectively, in accordance with some example aspects of the present disclosure.

FIG. 12A illustrates an example user interface view associated with sensor data representative of glucose concentration level(s) in a host in a vertical layout which corresponds to the wireframe of FIG. 11A, in accordance with some example aspects of the present disclosure.

FIG. 12B illustrates an example user interface view associated with sensor data representative of glucose concentration level(s) in a host in a horizontal layout which corresponds to the wireframe of FIG. 11B, in accordance with some example aspects of the present disclosure.

FIGS. 12C-12G illustrate enlarged views of features one through four shown in the vertical and horizontal user interface views of FIG. 12A and FIG. 12B, in accordance with some example aspects of the present disclosure.

FIG. 13A illustrates an example wireframe of another example user interface view in a vertical horizontal layout, in accordance with some example aspects of the present disclosure.

FIG. 13B illustrates an example wireframe of another example user interface view in a horizontal layout, in accordance with some example aspects of the present disclosure.

FIG. 18 is a table categorizing example analyte data widgets, in accordance with some example aspects of the present disclosure.

FIG. 46 illustrates another example event type widget, in accordance with some example aspects of the present disclosure.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Figure 1:
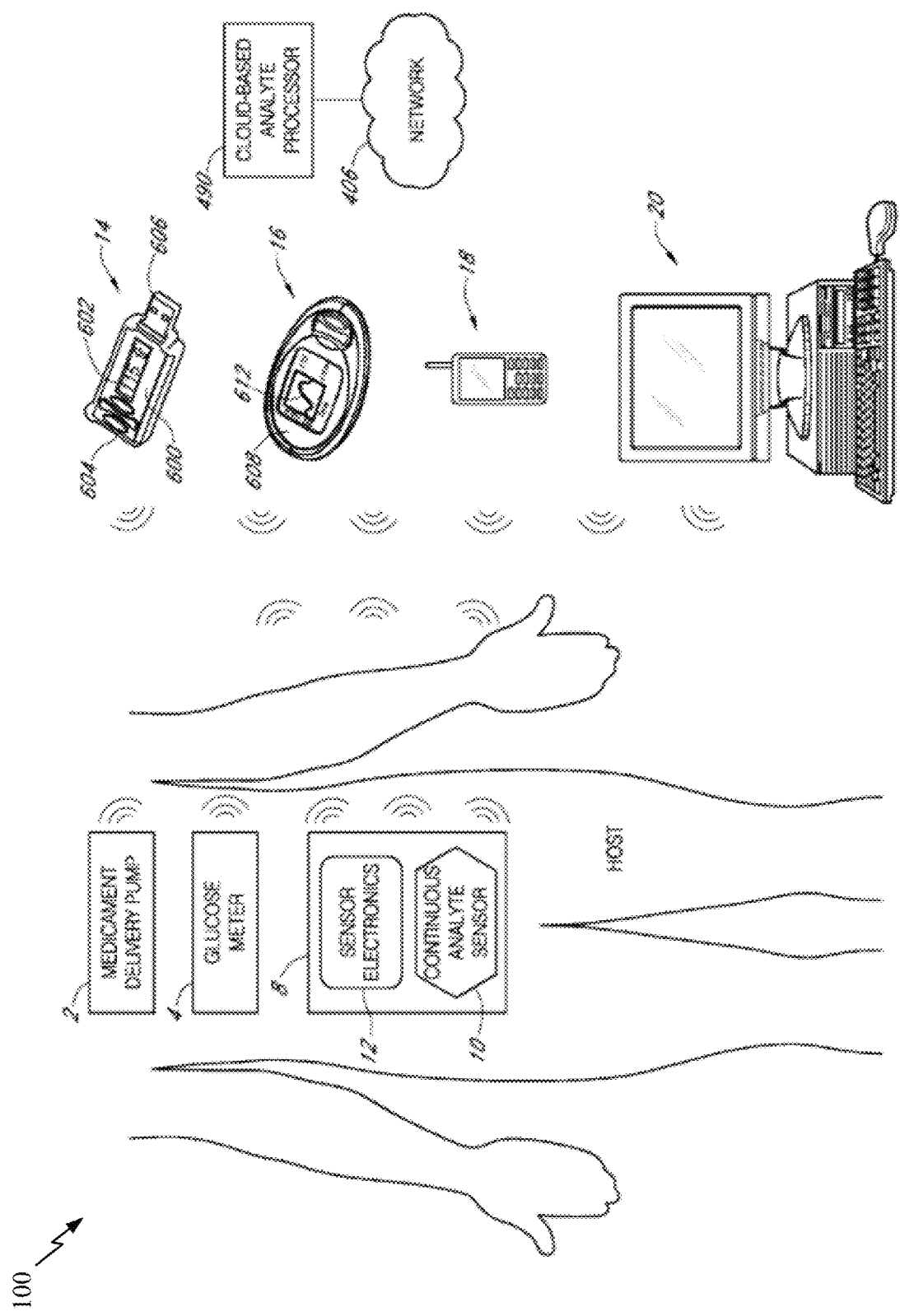
FIG. 1 is a diagram conceptually illustrating an example system including an example continuous analyte sensor with sensor electronics, in accordance with some example aspects of the present disclosure.

Data visualization is the process of translating large data sets and metrics into charts, graphs, and other visuals. The resulting visual representation of data makes it easier to identify and/or share real-time trends, outliers, and new insights about the information represented in the data. Perhaps one of the most pivotal advantages of data visualization is that digital visualization facilitates the easy and quick assimilation of large amounts of data. Visualization allows analysts and end users to recognize patterns and relationships in large volumes of data that may not be easily seen in raw data or reports. This may help in identifying emerging trends, for example, to allow a user to address health issues before they become bigger problems. The goal is to provide actionable insights that help drive change. For ease of explanation, a user herein, may refer to a patient (also referred to as a host); however, a user may refer to the patient's caregiver, or any other individual with an interest in the patient's well-being.

Health data visualization is increasingly a major focus in health analytics. Visualizing health data is a powerful way to share urgent health information swiftly and effectively. When implemented correctly, health data visualization may provide numerous benefits to an end user. For example, data visualization tools may promote the improved absorption of health information, provide quick access to meaningful health insights, communicate findings in a constructive way to engage and inform users of future and/or current health issues, and encourage user interaction with data to make informed lifestyle decisions and changes to stimulate a healthy lifestyle.

There is a growing emphasis on self-monitoring applications that allow patients to measure their own physical health parameters. Data visualization techniques and tools play an important role in the continuous management of one's health. For example, data visualization techniques and tools may be used to efficiently analyze, report, and provide insights to a diabetic user for continuous management of a diabetic condition.

Aspects of the present disclosure provide apparatus, methods, processing systems, and computer-readable mediums for analyte data processing, reporting, and visualization.

The term "analyte" as used herein is a broad term used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. Analytes for measurement by the devices and methods may include, but may not be limited to, potassium, glucose, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); androstenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, glucose-6-phosphate dehydrogenase, hemoglobin A, hemoglobin S, hemoglobin C, hemoglobin D, hemoglobin E, hemoglobin F, D-Punjab, hepatitis B virus, HCMV, HIV-1, HTLV-1, MCAD, RNA, PKU, *Plasmodium vivax,* 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free 3-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sisomicin; somatomedin C; specific antibodies recognizing any one or more of the following that may include (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. Ions are a charged atom or compounds that may include the following (sodium, potassium, calcium, chloride, nitrogen, or bicarbonate, for example). The analyte can be naturally present in the biological fluid, for example, a metabolic product, a hormone, an antigen, an antibody, an ion and the like. Alternatively, the analyte can be introduced into the body or exogenous, for example, a contrast agent for imaging, a radioisotope, a chemical agent, a fluorocarbon-based synthetic blood, a challenge agent analyte (e.g., introduced for the purpose of measuring the increase and or decrease in rate of change in concentration of the challenge agent analyte or other analytes in response to the introduced challenge agent analyte), or a drug or pharmaceutical composition, including but not limited to exogenous insulin; glucagon, ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA), and intermediaries in the Citric Acid Cycle.

While the analyte for measurement and visualization by the devices and methods described herein is glucose, other analytes listed, but not limited to, above may be considered. Biological parameters, such as body temperature, heart rate, metabolic function, respiratory rate, and the like, may be also be considered.

Aspects provide for a report that may be generated by a processor based on analyte data, for example, continuous glucose monitoring (CGM) data. The report may also be generated based on information input from a user and/or other information. The report may include information, such as an average analyte concentration level of the user for the current week and a comparison of the average analyte concentration level of the user for the current week to analyte concentration levels of the user for at least two previous weeks, and/or a per-day average analyte concentration level of the user, per-day percentages of analyte concentration levels of the user at one or more analyte concentration level ranges. The information in the report may be customizable by the user. Aspects of the disclosure provide for various data associated with continuous analyte monitoring that can be processed and used to generate one or more user views that may be presented on one or more widgets to a user. The information and user views can be updated based on the continuously monitored data and/or based on other parameters. The widgets may include summary type widgets, motivation type widgets, event type widgets, and/or other widgets. The widgets may also be customizable by a user.

FIG. 1 is a diagram conceptually illustrating an example system 100 including an example continuous analyte sensor with sensor electronics, in accordance with certain aspects of the present disclosure. For example, the system 100 may be configured to provide a report, based on continuously monitored analyte data, in accordance with certain aspects discussed in more detail with respect to FIGS. 5-14. The system 100 may be configured to provide one or more widgets based on continuously monitored analyte data, in accordance with certain aspects discussed in more detail herein with respect to FIGS. 15-55.

The system 100 includes a continuous analyte sensor system 8 including sensor electronics 12 and a continuous analyte sensor 10. The system 100 may include other devices and/or sensors, such as a medicament delivery pump 2 and a glucose meter 4. The continuous analyte sensor 10 may be physically connected to a sensor electronics 12 and may be integral with (e.g., attached and non-releasable) or releasably attachable to the continuous analyte sensor 10. The sensor electronics 12, medicament delivery pump 2, and/or glucose meter 4 may couple with one or more devices, such as display devices 14, 16, 18, and/or 20.

In some aspects, the system 100 may include an analyte processor 490 configured to analyze analyte data (and/or other patient related data) provided via network 406 (e.g., via wired, wireless, or a combination thereof). As later shown in FIG. 4, in certain embodiments, analyte processor 490 is a cloud-based processor that is configured to analyze analyte data received through network 406 from continuous analyte sensor system 8 and/or other devices, such as display devices 14, 16, 18, and/or 20 and the like, associated with the user and generate reports providing high-level information, such as statistics, regarding the measured analyte over a certain time frame. In embodiments where the analyte processor 490 is a cloud-based processors, the generated reports may be provided, in the form of user interface (UI) views, to UIs (e.g., UIs 410A-C of FIG. 4) of display devices 14, 16, 18, and/or 20.

Figure 4:
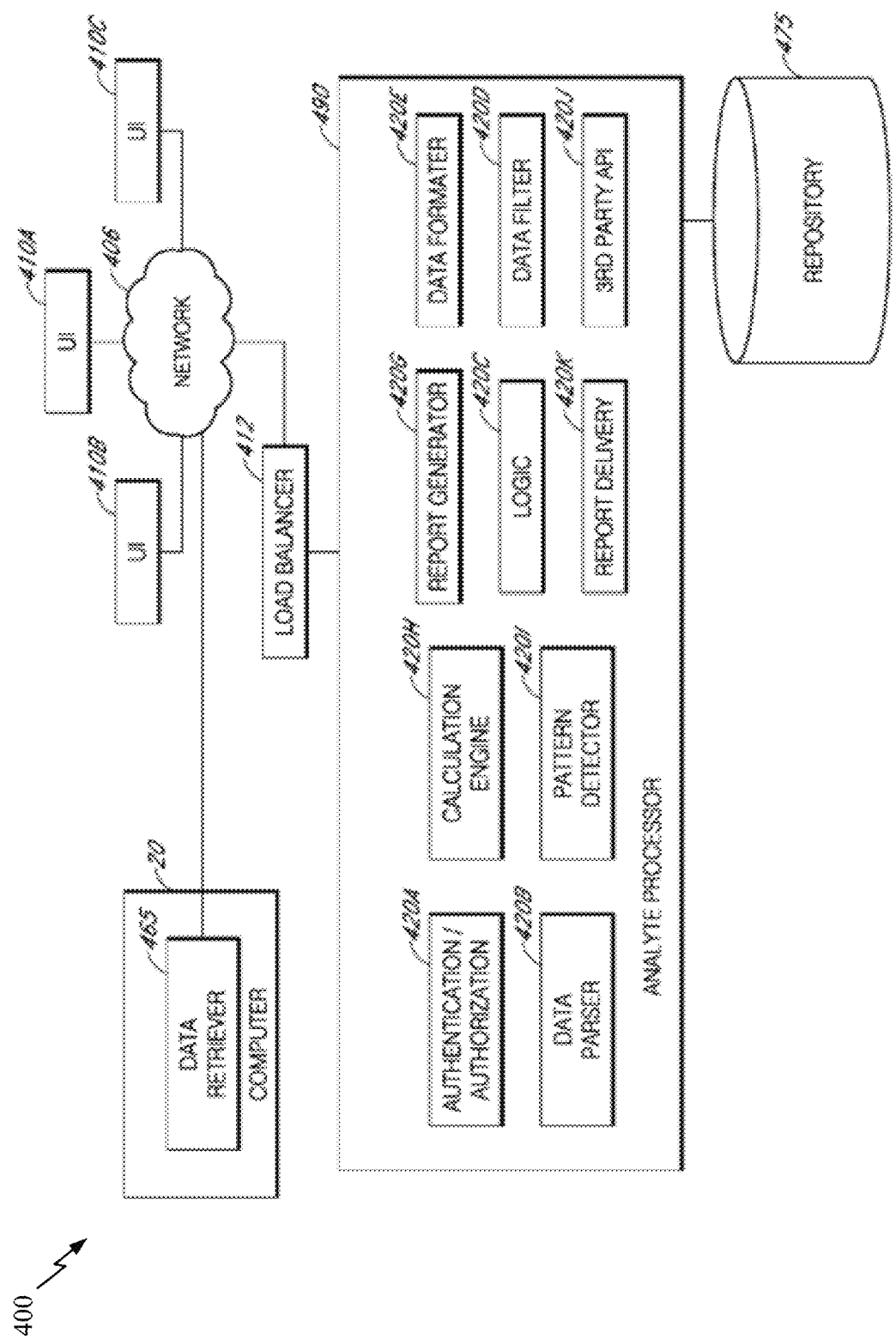
FIG. 4 is a block diagram conceptually illustrating an analyte processing system, in accordance with some example aspects of the present disclosure.

Although not shown in FIG. 4, in certain embodiments, the analyte processor may be one of display devices 14, 16, 18, or 20 that is configured to analyte data received from continuous analyte sensor system 8 and/or other devices, such as the other display devices. In such embodiments, analyte processor 490 receives analyte data (e.g., directly) from continuous analyte sensor system 8 and generates the UI views, reports, etc., described herein. In yet other embodiments, some of functionalities 420A-420J of analyte processor 490 may be executed by one or more of display devices 14-20 while the remaining functionalities may be executed by a cloud-based server.

In some aspects, analyte processor 490 or a report generator therein may generate a view for display at a user interface and/or for display on one or more widgets at a user interface. The user interface view may include one or more graphical representations comprising a plurality of different graphically distinct elements representative of processed analyte data and/or other information.

In some aspects, system 100 may generate performance reports and/or user interface views dynamically. For example, the analyte processor 490 may receive a request to generate a report or a user interface view. In response to the request, the analyte processor 490 may then select the reports and/or interface views to provide. In certain embodiments, this selection may be performed based on metadata. The metadata may include information about the request, information about or representative of the user (e.g., user's personal information, user's analyte information as provided by continuous analyte sensor system 8, etc.), the type of device being used to display the report and/or measure the analyte concentration level, rules, and the like.

The selection may be considered dynamic in the sense that the report and/or user interface view selection varies for each request based on metadata. The report or user interface view may then be generated to include at least one selected report and/or user interface view and then provided to a user interface for presentation.

In some aspects, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof to provide measurement of levels of the analyte via a continuous analyte sensor, such as a continuous glucose sensor. An example implementation of the sensor electronics 12 is described further below with respect to FIG. 2.

The sensor electronics 12 may, as noted, couple (e.g., wirelessly and the like) with one or more devices, such as display devices 14, 16, 18, and/or 20. The display devices 14, 16, 18, and/or 20 may be configured for presenting (and/or alarming) information, such as sensor information transmitted by the sensor electronics 12 for display at the display devices 14, 16, 18, and/or 20.

The display devices may include a relatively small, key fob-like display device 14, a relatively large, hand-held display device 16, a cellular phone display device 18 (e.g., a smart phone, a tablet, and the like), a computer 20, and/or any other user equipment configured to at least present information (e.g., a medicament delivery information, discrete self-monitoring glucose readings, heart rate monitor, caloric intake monitor, and the like).

In some aspects, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device) and may be configured to display certain types of displayable sensor information, such as a numerical value and an arrow.

In some aspects, the relatively large, hand-held display device 16 may comprise a hand-held receiver device, a palm-top computer, and/or the like. This large display device 16 may include a relatively larger display (e.g., larger than the small display device) and may be configured to display information, such as a graphical representation of the continuous sensor data including current and historic sensor data output by continuous analyte sensor system 8.

In some aspects, the continuous analyte sensor 10 may comprise a sensor for detecting and/or measuring analytes, and the continuous analyte sensor 10 may be configured to continuously detect and/or measure analytes as a non-invasive device, a subcutaneous device, a transdermal device, and/or an intravascular device. In some example aspects, the continuous analyte sensor 10 may analyze a plurality of intermittent blood samples, although other analytes may be used as well.

In some aspects, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In aspects in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a user. The data stream may be raw data signal, which is converted into a calibrated and/or filtered data stream used to provide a value of glucose to a user or a caretaker (e.g., a parent, a relative, a guardian, a teacher, a doctor, a nurse, or any other individual that has an interest in the wellbeing of the user). Moreover, the continuous analyte sensor 10 may be implanted as at least one of the following types of sensors: an implantable glucose sensor, a transcutaneous glucose sensor, implanted in a user vessel or extracorporeally, a subcutaneous sensor, a refillable subcutaneous sensor, an intravascular sensor.

Although the description herein refers to some examples that include a continuous analyte sensor 10 comprising a glucose sensor, the continuous analyte sensor 10 may comprise other types of analyte sensors, as well. Moreover, although some aspects may refer to the glucose sensor as an implantable glucose sensor, other types of devices capable of detecting a concentration of glucose and providing an output signal representative of glucose concentration may be used, as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2:
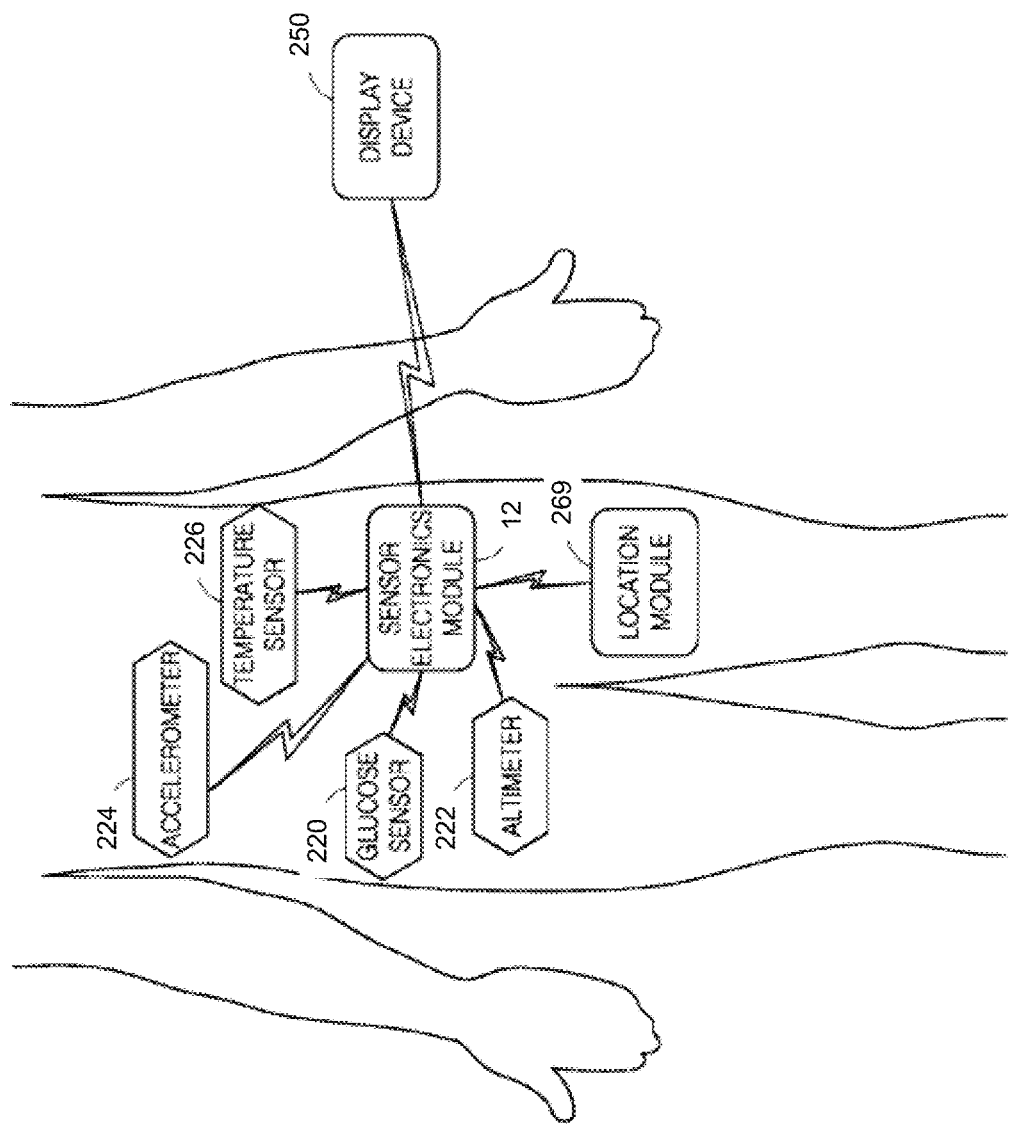
FIG. 2 is a block diagram conceptually illustrating a sensor electronics module communicating with multiple sensors, in accordance with some example aspects of the present disclosure.

FIG. 2 is a block diagram 200 conceptually illustrating a sensor electronics module communicating with multiple sensors, in accordance with certain aspects of the present disclosure. As shown in FIG. 2, a sensor electronics module 212 may be in communication with multiple sensors, including a glucose sensor 220, an altimeter sensor 222, an accelerometer sensor 224, a temperature sensor 226, and a location module 269 (e.g., a global positioning system (GPS) processor or other source of location information) in accordance with some example aspects. Although FIG. 2 illustrates the sensor electronics module 212 in communication with specific sensors, other sensors and/or devices may be used. Other devices and/or sensors may include, for example, heart rate monitors, blood pressure monitors, pulse oximeters, an impedance sensor, a dialysis machine, caloric intake devices, and medicament delivery devices. Moreover, one or more of these sensors may provide data to an analyte processing system 400 (referred to herein as "processing system 400") and/or analyte processor 490 described further below. In some aspects, a user may manually provide some of the data to processing system 400 and/or analyte processor 490. For example, a user may provide calorie consumption information via a user interface to processing system 400 and/or analyte processor 490.

In the example illustrated in FIG. 2, each of the sensors 220, 222, 224, and/or 226 may communicate sensor data wirelessly to the sensor electronics module 212. In some examples, the sensor electronics module 212 may include one or more of the sensors 220, 222, 224, and/or 226. In some example, the sensors 220, 222, 224, and/or 226 may be combined in any other configuration, such as, for example, a combined glucose/temperature sensor (e.g., or a multi-analyte sensor) used to transmit sensor data to the sensor electronics module 212 using common communication circuitry. Depending on the example, fewer or additional sensors may communicate with the sensor electronics module 212. In some examples, one or more of the sensors 220, 222, 224, and/or 226 may be directly coupled to the sensor electronics module 212 (e.g., coupled via one or more electrical communication wires).

The sensor electronics module 212 may generate and transmit a data package to a device, such as display device 250. Display device 250 may be any electronic device configured to receive, store, retransmit, and/or display displayable sensor data. Display device 250 may be any of the display devices 14, 16, 18, and/or 20 illustrated in FIG. 1. The sensor electronics module 212 may analyze the sensor data from the multiple sensors and determine which displayable sensor data is to be transmitted based on one characteristics of the user, the display device 250, a user of the display device 250, and/or characteristics of the sensor data. Thus, the customized displayable sensor information transmitted to the display device 250 may be displayed on the display device with minimal processing by the display device 250.

Figure 3B:
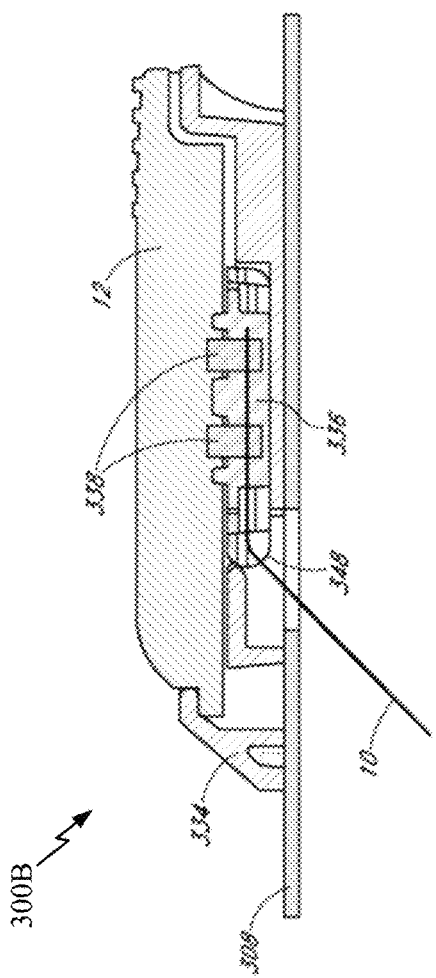
FIGS. 3A and 3B illustrate different views of a sensor system including a mounting unit and sensor electronics attached thereto, in accordance with some example aspects of the present disclosure.
Figure 3A:
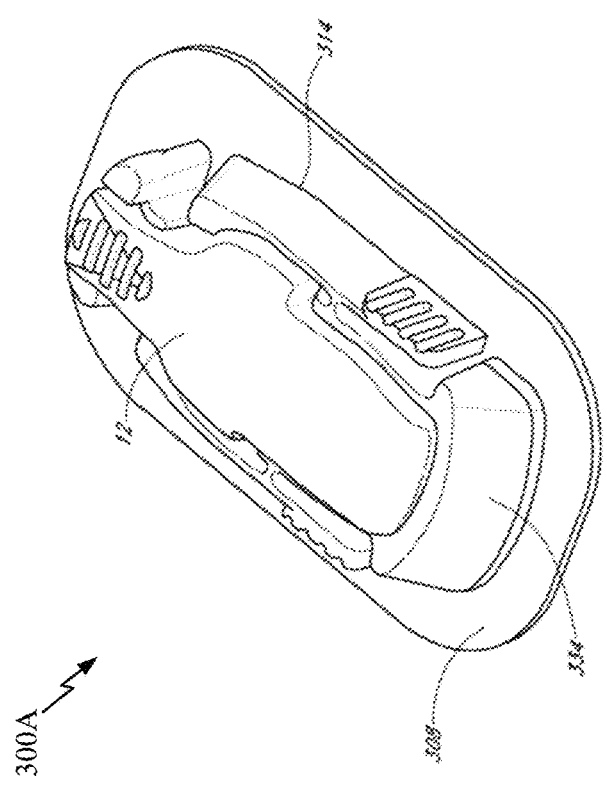

FIGS. 3A and 3B are perspective and side views, 300A and 300B, respectively, of a sensor system including a mounting unit 314 and sensor electronics 12 attached thereto. In an example, shown in its functional position, the mounting unit 314 may be matingly engaged with the sensor electronics 12. In some examples, the mounting unit 314, also referred to as a housing or sensor pod, may include a base 334 adapted for fastening to a user's skin. The base 334 may be formed from a variety of hard or soft materials, and may comprise a low profile for minimizing protrusion of the device from the user during use. The base 334 may be formed at least partially from a flexible material, which is believed to provide, in some aspects, numerous advantages over other transcutaneous sensors, which, unfortunately, can suffer from motion-related artifacts associated with the user's movement when the user is using the device. The mounting unit 314 and/or sensor electronics 12 may be located over the sensor insertion site to protect the site and/or provide a minimal footprint (utilization of surface area of the user's skin).

In some example aspects, a detachable connection between the mounting unit 314 and sensor electronics 12 may be provided. The detachable connection may enable improved manufacturability. Namely, the relatively inexpensive mounting unit 314 may be disposed of when replacing the sensor system after its usable life, while the relatively more expensive sensor electronics 12 may be reusable with multiple sensor systems. In some example aspects, the sensor electronics 12 may be configured with signal processing. For example, the sensor electronics 12 may be configured to filter, calibrate, and/or provided with other algorithms useful for calibration and/or display of sensor information.

In some example aspects, the contacts 338 may be mounted on or in a subassembly (hereinafter referred to as a contact subassembly 336) configured to fit within the base 334 of the mounting unit 314 and a hinge 348 that allows the contact subassembly 336 to pivot between a first position (for insertion) and a second position (for use) relative to the mounting unit 314. The hinge may provide pivoting, articulating, and/or hinging mechanisms, such as an adhesive hinge, a sliding joint, and the like. The action of the hinge may be implemented, in some aspects, without a fulcrum or a fixed point about which the articulation occurs. In some example aspects, the contacts 338 may be formed from a conductive elastomeric material, such as a carbon black elastomer, through which the continuous analyte sensor 10 extends, although the contacts may be formed in other ways as well.

In some example aspects, the mounting unit 314 may be provided with an adhesive pad 308, disposed on the mounting unit's back surface and including a releasable backing layer. Thus, removing the backing layer and pressing the base 334 of the mounting unit onto the user's skin may allow for adherence of the mounting unit 314 to the user's skin. Additionally or alternatively, an adhesive pad may be placed over some or all of the sensor system after sensor insertion is complete to ensure adhesion, and optionally to ensure an airtight seal or watertight seal around the wound exit-site (or sensor insertion site). Appropriate adhesive pads may be chosen and designed to stretch, elongate, conform to, and/or aerate the region (e.g., user's skin). The configurations and arrangements that provide water resistant, waterproof, and/or hermetically sealed properties may be provided with some of the mounting unit/sensor electronics aspects described herein.

FIG. 4 is a block diagram conceptually illustrating an example analyte processing system, in accordance with some example aspects of the present disclosure. As shown in FIG. 4, the processing system 400 may include one or more user interfaces 410A-C, such as a browser, an application, a widget, and/or any other type of user interface configured to allow accessing and/or interacting with analyte processor 490 via, for example, network 406 and a load balancer 412. The analyte processor 490 may further be coupled to repository 475. User interfaces 410A-C may be associated with or provided as part of display devices 14, 16, 18, 20 and/or any other display devices used by a user to view the user interface views, reports, etc., described herein.

Processing system 400 may also receive data from source systems, such as health care management systems, patient management systems, prescription management systems, electronic medical record systems, personal health record systems, and the like. This source system information may provide metadata for dynamic report generation.

Processing system 400 may be implemented in a variety of configurations including stand-alone, distributed, and/or cloud-based frameworks. Processing system 400 may be implemented in a cloud-based framework, such as a software-as-a-service (SaaS) arrangement in which the analyte processor 490 is hosted on computing hardware, such as servers and data repositories maintained remotely from an entity's location (e.g., remote from a user, a health service provider, and like end-user) and accessed over network 406 by authorized users via a user interface, such as user interface 410A, 410B, and/or 410C, and/or a data retriever 465.

In addition to the example illustrated in FIG. 4, processing system 400 may be implemented as a SaaS-based system including a plurality of servers, each of which may be virtualized to provide one or more analyte processors 490. Moreover, each of the virtualized analyte processors 490 may serve a different tenant, such as an end-user, a clinic, a user wearing a sensor, and the like. To make more efficient use of computing resources of a SaaS provider and to provide important performance redundancies and/or reliability, it may, in some aspects, advantageous to host multiple tenants (e.g., users, clinics, etc. at user interfaces 410A-C and/or data retriever 465) on a single processing system 400 that includes multiple servers and that maintains data for all of the multiple tenants in a secure manner at repository 475 while also providing customized solutions that are tailored to each tenant.

Referring again to FIG. 4, in some example aspects, processing system 400 may provide a cloud-based diabetes data management framework configured to receive patient-related data from various devices. Various devices may include, and is not limited to, a medical device, a glucose meter, a continuous glucose monitor, a continuous analyte sensor system 8, display devices 14, 16, 18, and/or 20, source systems, a device providing food consumption information (e.g., such as carbohydrates) associated with food consumed by a user, medicament delivery data, time of day, temperature sensors, and/or exercise/activity sensors. In some example aspects, the cloud-based diabetes data management may receive the data programmatically with little (or no) intervention on the part of a user. The data received from devices, source systems, and the like, may be in a variety of formats and may be structured or unstructured. For example, in some example aspects, the processing system 400 may receive raw sensor data, which has been minimally processed or analyzed. The received data may then formatted, processed (e.g., analyzed), and/or stored in order to enable analyte data visualization.

For example, a data retriever 465 may be implemented at one or more devices, such as computer 20 coupled to continuous analyte sensor system 8. In this example, data retriever 465 may format sensor data into one or more common formats compatible with analyte processor 490 and may provide the formatted data to analyte processor 490 such that analyte processor 490 may analyze the formatted data. Although FIG. 4 depicts a single data retriever 465, in some example aspects, a plurality of data retrievers 465 may be used to format data from a plurality of devices and/or systems. In certain embodiments, data retriever 465 may execute on or be hosted at any other one of display devices, such as display devices 14, 16, and/or 18, in communication with continuous analyte sensor system 8.

In some example aspects, the data retriever 465 may be accessed through a kiosk including a processor, such as a dedicated computer, configured with a user interface, or may be accessed via a secure web-based interface residing on a non-dedicated computer.

In some example aspects, the first time a processor (e.g., a computer, a smart phone, and any other device) accesses processing system 400, the data retriever may be programmatically installed on the processor by downloading software for the data retriever to the processor's memory. The downloaded software may then be programmatically installed on the processor, and then data retriever may generate a view which may be presented on a user interface.

In some aspects, this user interface may allow a user to select an icon, such as a fetch icon, to programmatically start a data transfer to analyte processor 490. For example, a user selects the fetch icon at the user interface on a processor, such as computer 20, which initiates a data transfer from a continuous analyte sensor system 8 coupled to data retriever 465 and analyte processor 490. In some aspects, the fetch icon may be implemented as a software widget. Moreover, the software widget may be placed on a webpage, so that when selected a fetch process begins for a registered user.

Moreover, the software associated with the data retriever 465 may include a self-updating mechanism, so that when a fetch is selected at the user interface, the data retriever programmatically checks for an update (e.g., software, drivers, data, and the like) at analyte processor 490 (or another designated computer) and installs the update. The update may be performed programmatically with little (or no) intervention by a user. Data downloads from a device or system to the data retriever 465 may be performed using a wired connection, such as a device-specific download cable, or wirelessly, when the device and the processor are equipped for wireless data transfer.

The analyte processor 490 may check data downloaded by the data retriever 465 for transmission-related errors, data formatting, device-related error codes, validity of the data, duplicate data points, and/or other aspects of the data. Moreover, if out-of-range data points or device errors are found, the analyte processor 490 may identify those data points. For example, the analyte processor 490 may flag those data points, correct the identified data points programmatically or by a system administrator, and store the corrected data points. Moreover, the analyte processor 490 may be configured by a user, such as a clinician, doctor, and the like, to perform additional data processing steps, such as correcting time of day, correcting the date, and analyzing data by specific cohorts, groups, and/or relationships (e.g., demographics, such as age, city, state, gender, ethnicity, Type I diabetes, Type II diabetes, age of diabetes diagnosis, lab results, prescription drugs being used, self-reported conditions of the patient, diagnosed conditions of the patient, responses to questions posed to patient, and any other metadata representative of the user). Once the analyte processor 490 performs initial data processing (e.g., checks, cleaning, and analysis), the processed data and/or the raw data provided by the data retriever may be stored at repository 475.

The processing at analyte processor 490 may also include associating metadata with the data received from the devices and/or sensors. Examples of metadata may include, but is not limited to, patient information, keys used to encrypt the data, patient accelerometer, location data (e.g., location of patient or location of patient's clinic), time of day, date, type of device used to generate associated sensor data. The patient information may include the patient's age, weight, sex, home address and/or any past health-related information, such as whether the patient has been diagnosed as a type 1 or type 2 diabetic, high-blood pressure, or as having any other health condition.

The processing may also include analysis, such as determining one or more descriptive measurements and/or generating one or more user interface views based on received information, the metadata, and descriptive measurements. These descriptive measurements may include statistics (e.g., median, inner and outer quartile ranges, mean, sum, n, standard deviation, and coefficients of variation). Examples of user interface views are depicted in FIGS. 7-14F and 19-55.

In the example of FIG. 4, user interfaces 410A-C may be used by one or more entities, such as end-users, health care providers, clinics, patients, research groups, health systems, medical device manufacturers and the like. These entities may remotely access processing system 400 via user interface 410A-C (e.g., of display devices 14, 16, 18, and/or 20) to request an action, such as retrieve analyte data, provide analyte data, request analysis of analyte data, request generation of reports including modules having views presenting descriptive measurements of the analyte data, present analyte data and reports, and the like. Other examples of actions include providing sensor data, such as glucose data, carbohydrate data, insulin pump data, and the like, to the analyte processor 490, initiating processing of the sensor data, initiating analysis of the sensor data, and storing data at repository 475. In some example aspects, the computing resources provided by analyte processor 490 may comprise one or more physical servers virtualized to provide the analyte processing services disclosed herein.

The data retriever 465 may obtain (e.g., receive, retrieve, etc.) data from one or more sources and provide any obtained data in a format compatible for use within analyte processor 490. In some aspects, data retriever 465 may be implemented in one or more of the source systems and/or devices providing data to analyte processor 490. For example, data retriever 465 may be implemented in one or more devices, such as continuous analyte sensor system 8, continuous analyte sensor 10, display devices 14, 16, 18, and/or 20, medicament delivery pump 2, glucose meter 4, computers/processors coupled to those devices, and any other device capable of providing data to analyte data processing system 400. In these aspects, data retriever 465 may receive data from a user device and format the data in a format compatible with analyte processor 490. The data retriever 465 may also be implemented on source systems, such as disease management systems, weight management systems, prescription management systems, electronic medical records systems, personal health record systems, and the like. In these aspects, data retriever 465 may obtain data from the source system and format the data in a format compatible with analyte processor 490.

In some example aspects, data retriever 465 may, as noted, be downloaded and/or provided automatically to a device, a computer, a system, and the like. For example, when a user on a computer first accesses analyte data processing system 400, analyte data processing system 400 may automatically install and configure the data retriever 465 on the user's computer. Once the install is complete, the data retriever 465 may begin fetching data for processing system 400 and format, if needed, the data to allow processing of the fetched data by analyte processor 490. To further illustrate by way of an example, the data retriever 465 may be downloaded onto a device, such as computer 20. In this example, when computer 20 receives sensor data from sensor electronics module 12, a data retriever 465 may provide sensor data and/or metadata in a format compatible with analyte processor 490.

In some example aspects, the analyte processor 490 may process the received data by performing one or more of the following: associate metadata with the data received from the devices, sensors, source system, and/or data retriever, determine one or more descriptive measurements, such as statistics (e.g., median, inner and outer quartile ranges, mean, sum, n, and standard deviation), validating and verifying the integrity of the received data from the devices, sensors, source system, and/or data retriever, process received data based on metadata (e.g., to select certain patients, devices, conditions, diabetic type, and the like), and/or correlate received data from the devices, sensors, source system, and/or data retriever so that the data may be compared and combined for processing and analyzing.

Moreover, the results of any processing performed by analyte processor 490 may be used to generate views presenting descriptive measurements and/or comparisons of the analyte data (e.g., user interface views depicted in FIGS. 7-14F and 19-55). The descriptive measurements and/or comparisons may be presented, for example, as graphs, bar graphs, static charts, charts, badges, tables, figures, maps, plots, and/or other visualizations.

Figure 57:
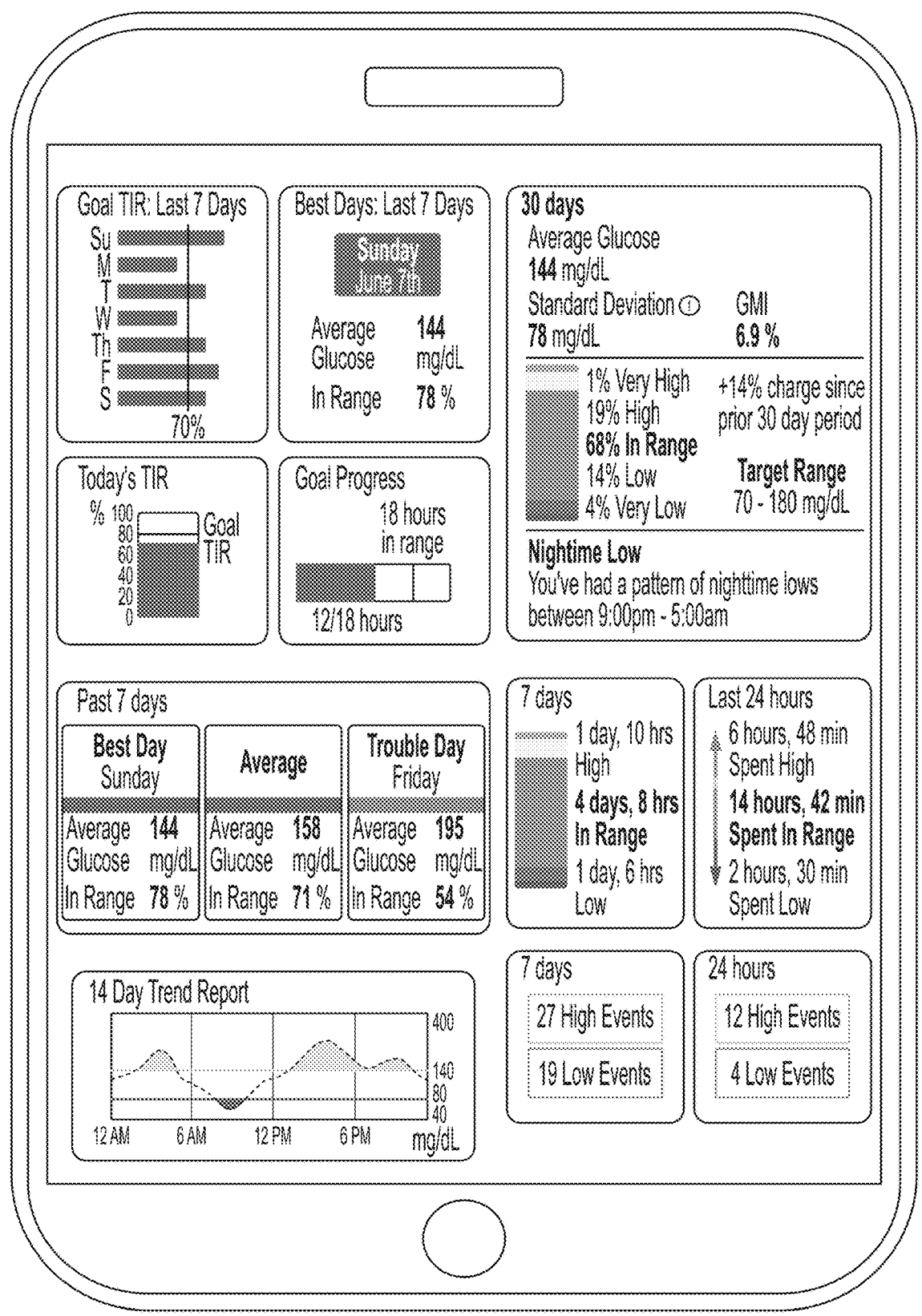
FIG. 57 illustrates an example user interface that may include various widgets, in accordance with some example aspects of the present disclosure.

Furthermore, the outputs generated by processing system 400 may be provided via one or more delivery mechanisms, such as report delivery module 420K. For example, the report delivery module 420K may provide outputs generated by analyte data processing system 400 via email (e.g., as illustrated in FIGS. 7-14F), secure email, print, text, presentations for display at a user interface (such as at user interface 410A-C hosted at a tablet, phone (e.g., as illustrated in FIG. 57), or other processor), machine-to-machine communications (e.g., via third party interface 420J), and any other communication mechanism.

In some example aspects, the views may be customized dynamically for use by, for example, an entity, such as an end-user, a clinician, a healthcare provider, or a device manufacturer. Furthermore, the views may be customized based on the types and/or quantity of sensors and systems providing data to processing system 400 and metadata or the types thereof available to processing system 400. This customization may be performed by a user, by processing system 400 programmatically, or a combination of both.

Analyte processor 490 may include, in some example aspects, an authenticator/authorizer 420A for authorizing access to analyte processor 490, a data parser 420B for parsing requests sent to analyte processor 490, a calculation engine 420H for receiving data from sensors and processing the received data into counts for use with histograms, logic 420C, a data filter 420D, a data formatter 420E, a report generator 420G, a pattern detector 420I, a report delivery module 420K for delivering views in a format for the destination, and a third party access application programming interface to allow other systems and device to access and/or interact with analyte processor 490.

Analyte processor 490 may receive a request from a user interface, such as user interface 410A-C, to perform an action (e.g., provide data, store data, analyze/process data, request a report, and the like). Before analyte processor 490 services the request, the analyte processor 490 may process the request to determine whether the request is authorized and authenticated. For example, authenticator and authorizer 420A may determine whether the sender of the request is authorized by requiring a user to provide a security credential (e.g., a user identifier, a password, a stored security token, and/or a verification identifier provided by text message, phone, or email) at a user interface presented on a computer. If authorized, authenticator and authorizer 420A may authenticate the sender of the request to check whether a security credential associated with sender of the request indicates that the sender (e.g., a user at user interface 410A) is indeed permitted to access a specific resource at analyte data processing system 400 in order to perform the action, such as store (or upload) data at repository 475, perform analyze/process data, and/or request user interface view generation.

To further illustrate, the data retriever 465 associated with a continuous analyte sensor system 8 and a computer 20 may be authorized and authenticated by authenticator and authorizer 420A to access analyte processor 490 in order to write data to a buffer or other storage mechanism, such as repository 475. On the other hand, an entity, such as a user, at user interface 410A may be authorized and then authenticated by authenticator and authorizer 420A to access analyte processor 490, but only permitted to access certain information. In this second example, the user at user interface 410A may be authorized and authenticated to access repository 475 to view certain information corresponding to the user's own analyte data (e.g., glucose data) and access reports generated for the analyte data, but the user will not be authorized and authenticated to access another user's data.

Once authorized and/or authenticated, the request received at analyte processor 490 may then be parsed by data parser 420B to separate any data, such as sensor data, metadata, and the like, from the request. In some aspects, data parser 420B may perform check data formatting, device-related error codes, validity of the data, duplicate data points, and/or other aspects of the data. Moreover, the data parser 420B may associate additional metadata with the separated data. The metadata may include any of the metadata described herein, including an owner of the data, a key to track the data, an encryption key unique to each user, time of day, date information, one or more locations where the data is (or will be stored), and the like. In some example aspects, the data parsing 420 may provide data to the calculation engine 420H for formatting the data into counts and histograms as described further below.

In some example aspects, the request (or the parsed data therein) may be processed by calculation engine 420H. The calculation engine 420H may preprocess the data received from devices, sensors, and the like to form "counts." The counts may represent a measured value, such as an analyte value measured by a sensor, a glucose value measured by a sensor, a continuous glucose value measured by a sensor, and/or other diabetes related information, such as carbohydrates consumed, temperature, physical activity level, and the like, and how often that measured value occurred.

The calculation engine 420H may then use the count 508 to perform additional processing. The additional processing may include storing the count in repository 475, which may include one or more databases to store the counts. Moreover, the count may be stored with metadata, such as time of day/date information. Furthermore, the count may be encrypted, as noted, before storage in repository 475.

The calculation engine 420H may also use the count to update one or more histograms. For example, rather than keep track of and process a user's analyte levels over a certain period of time using raw sensor data values, the calculation engine 420H may convert the data values into counts. The counts may be added to histograms, for a given user.

In some example aspects, the calculation engine 420H may generate a plurality of histograms for a given user for a plurality of given time periods.

In some example aspects, the calculation engine 420H may also update other histograms representative of aggregate count information.

Although the description with respect to the calculation engine 420H refers to a histogram, the histogram, as used herein, refers to a data structure that includes one or more values associated with one or more time intervals. For example, the histogram may represent one or more values, such as frequency of occurrence, associated with bins corresponding to one or more time intervals. Moreover, this data structure may be stored at a database, such that the data structure is readily accessed with a read, such as in a row of a database (or, for example, in a column if a column database is used).

In some example aspects, repository 475 stores the histograms including counts in a database. For example, repository 475 may store data for a user that covers a time frame, such as 1 day, 2 days 7 days, 14 days, 30 days, and/or any other time frame. In this example, the days may be subdivided into epochs, each of which has a corresponding histogram stored in repository 475. Moreover, each histogram may be stored as a row (or column) in a database at repository 475 to facilitate fast data access.

Logic 420C of FIG. 4 may also process requests to perform an action (e.g., store, retrieve, process, analyze, report data, etc.) at analyte processor 490. Logic 420C may also determine one or more descriptive measurements, such as statistics (e.g., a median, inner and outer quartile ranges, a mean, a sum, a standard deviation, and the like) based on counts, histograms, and/or received sensor data. The logic 420C may provide these descriptive measurements to the report generator 420G to enable report generation (e.g., generation of a view for presentation at user interfaces 410A-C). For example, the mean may be determined by summing the product of the count and the bin value and then dividing that sum by the sum of the counts.

Pattern detector 4201 of FIG. 4 may perform pattern detection on data (e.g., sensor data representative of blood glucose data, analytes, insulin pump data, carbohydrate consumption data, and the like) processed by analyte processor 490 and stored at repository 475. Moreover, the pattern detector 4201 may detect patterns retrospectively for a predetermined time period defined by processing system 400 and/or a user.

In some example aspects, the pattern detector 4201 may receive input data from the repository 475. The input data may include, for example, analyte concentration data, for example from a continuous analyte sensor, other analyte data, such as rate of change, predictive concentrations etc. In some example aspects, input data may also include other data such as temperature data, accelerometer data, insulin pump data, carbohydrate consumption data, food intake data, nutrition intake or breakdown information, time of day, exercise and/or activity data, awake/sleep time intervals, medications information, or other similar data relating to activities of the user that may impact one or more biological parameters of the user.

Moreover, the input data may comprise historical data obtained over a time frame, such as 8 hours, 1 day, 2 days, 7 days, 14 days, 30 days, and/or any other time frame. For example, the input data may include "counts" representative of monitored analyte detection levels (e.g., glucose concentration levels) received and stored at processing system 400 over a period covering a four-week (or more) time frame. As mentioned above, "counts" may be stored in repository 475 with metadata, such as time of day/date information, to be used as input data at a later time. In another example, the input data may include histograms updated by "counts" of the user. The histogram may include an x-axis of analyte concentration values and a y-axis of the number of occurrences for each analyte concentration value. The histogram associated with a given user/patient may be an example of input data used by pattern detector 4201.

The pattern detector 4201 may analyze the input data for patterns. For example, patterns may be recognized based on one or more predefined rules (also referred to as criteria or triggers). Furthermore, the one or more predefined rules may be variable and adjustable based user input. For example, some types of patterns and rules defining patterns may be selected, turned on and off, and/or modified by a user, a user's physician, or a user's guardian, although processing system 400 may select, adjust, and/or otherwise modify rules programmatically as well. In another example aspect, one or more patterns may be based on predefined rules set by factory settings or device settings.

The pattern detector 4201 may detect the pattern and generate an output, which may be provided to report generator 420G. Moreover, the output may include a retrospective analysis of the input data and any patterns determined by pattern detector 4201.

The data filter 420D may be used to check whether an output generated by analyte processor 490, such as a response for certain types of data, a report, and the like, does not violate a data rule. For example, the data filter 420D may include a data rule to check whether a response includes data, such as PII, to a destination which is not authorized or allowed to receive the response (e.g., based upon authorization and authentication and the corresponding role of the user making the request).

The data formatter 420E may format data for delivery based on the type of destination. For example, the data formatter 420E may format a view based on whether it is being sent to a printer, a user interface, a secure email, another processor, and/or any other similar device or platform.

The report generator 420G may generate one or more reports and/or user interface views. The reports/views may provide descriptive information, such as statistical information, representative of the sensor data received at analyte processor 490. Moreover, the report/view may provide a retrospective analysis of the sensor data stored at repository 475. For example, the report/view may provide statistical information based on sensor data (and/or corresponding histograms including counts) over a time frame, such as 8 hours, 1 day, 2 days, 7 days, 14 days, 30 days, and/or any other time frame. Moreover, the report/view may allow a user to view the information and identify trends and other health related issues.

In some example aspects, report generator 420G generates reports and/or views based on data received and/or stored at processing system 400 (e.g., using sensor data, metadata, counts, histograms, information associated with a request to generate a report, and the like). For example, report generator 420G may select one or more features or modules for providing as part of UIs displayed (FIGS. 5-57) to a user based on a request received by a user to generate a report. In certain embodiments, the request may include information such as the identity of the patient, identity of the requesting device, a type of report being requested, and/or the like. The request may also specify a time frame for the report and/or as any other information required to authenticate the device requesting device or user.

The report generator 420G may also select one or more features or modules for providing as part of UIs displayed (FIGS. 7-14F and 19-55) to a user based on metadata including rules, templates, and/or the like. This metadata may describe one or more of the following: types of data available; amount of data; types of devices being used; user preferences; size of the user interface available to present report; patient demographics; patient information including report preferences, types and quantity of devices used, and display size being used to present the report, and other data related to the user, devices, and the like; rules, such as whether a module can be used with certain devices (for example, certain reports may only be suitable for continuous blood glucose, rather than discrete measurements), whether a module can be used with certain patient conditions (for example, a caregiver may establish a rule requiring a certain report based on a patient's demographic, history, or condition), whether a module may be used on certain display sizes, whether a module may be used given a certain volume of data or device type; and/or one or more templates. For example, the selection of modules may be performed based on metadata including user preferences for certain modules, a type of device being used, a display area of the device, and a rule defining which modules can be used given the type of device, a patient state/condition, and the display area of the device. Furthermore, the metadata may be stored at a repository, such as repository 475, although some of the metadata or may be provided as part of the request received at 710.

A template may define the placement of one or more modules in a report. The framework defining the placement of each module may be a template (also referred to as a model or a wireframe). Moreover, templates may be defined for certain devices or displays, so that when the request is made and/or metadata obtained, the report generator 420G can dynamically select, based on metadata, one or more modules into the predefined template. For example, a certain display device may be of a size which allows four modules to be displayed in one way, while another display device may be of a size which allows the four modules to be displayed in a different way, and so forth.

In some exemplary implementations, the metadata may include a plurality of predefined templates configured for a specific patient, a specific caregiver, a specific medical professional, a group of patients (e.g., cohorts), a businessperson, and/or the like. As such, modules may be dynamically selected based on an evaluation of the metadata. Moreover, the use of the templates may, in some implementations, allow the dynamic generation of modules to be performed more rapidly, when compared to not using the templates. In any case, when the report generator 420G selects which modules 710A-D are to be included in the report, the report generator 420G may then obtain the underlying data (for example, sensor data, demographics, and the like) to be used in the selected modules. Examples of reports and/or user interface views that include features (also referred to as modules) are depicted in FIGS. 7-14F and 19-55.

According to certain aspects, logic 420C and pattern detector 4201 may be used to determine one or more descriptive measurements, patterns, or relationships for effective visualization. As described previously, logic 420C may determine a median, inner and outer quartile ranges, a mean, a sum, a standard deviation, and other statistical measurements based on counts, histograms, and/or received sensor data. Pattern detector 4201 may analyze relationships among the data to determine patterns. Relationships in the input data that may result in an identified pattern may include, for example, an analyte level that exceeds a target analyte range (e.g., which may be defined by a user, a health care provider, processing system 400, or a combination thereof), an analyte level that is below a target analyte range, a rapid change in analyte levels from low to high (or vice versa), times of day when a low, a high, an at range, or rapid analyte level event occurs, days when a low, a high, an at range, and/or a rapid analyte level event occurs.

Additional examples of the types of relationships in the input data that may be considered a pattern include very high and/or very low analyte events by time of day. As an example, in aspects where the analyte for measurement may be glucose, a pattern may be identified in situations where the user has low analyte concentrations around the same time in the day (e.g., a hypoglycemic event). Another type of pattern, which may be identified, is a "rebound high" situation. For example, a rebound high may be defined as a situation where a user overcorrects a hypoglycemic event by overly increasing glucose intake, thereby going into a hyperglycemic event. These events may be detected based on one or more predefined rules. Patterns that may be detected include a hyperglycemic pattern, a hypoglycemic pattern, patterns associated with a time of day or week, a weighted scoring for different patterns based on frequency, a sequence, and a severity.

In some aspects, patterns may be based on a custom sensitivity of a user/patient, a transition from a very low to a very high pattern, an amount of time spent in a severe event, and a combination of analyte change and time information. Detected patterns may also be patterns of high variability of analyte data. Further, a pattern may be based on a combination of previous pattern data and a currently detected situation, whereby the combined information generates a predictive alert.

FIG. 5 illustrates an example user interface view 500 associated with sensor data representative of analyte level (s), specifically glucose concentration level(s), in a user, in accordance with some example aspects of the present disclosure. Patterns and statistics identified by logic 420C and pattern detector 4201 may be presented in a performance report. As shown in FIG. 5, a weekly report may be provided to a user of a diabetes management application to provide relevant insights into a user's retrospective glucose values, patterns, and trends over time.

In a first feature of the user interface view 500, a time in range stacked bar graph, representing a percentage of time the user was in a target glucose range, a very high or high glucose range, and a very low or low glucose range over a specified period (e.g., any continuous seven day period), may be provided. The target glucose range may be defined as a different range for daytime (e.g., 6:00 AM-10:00 PM in the example shown) and nighttime (e.g., 10:00 PM-6:00 AM in the example shown) hours. The user's percentage of time in range may also be compared to the previous week's percentage of time in range. In some examples, the stacked bar graph may be presented using different colors to differentiate the percentages of time the user was in a target glucose range, a very high or high glucose range, and a very low or low glucose range over a specified period. In some examples, the stacked bar graph may be presented using different size blocks (stacked in the stacked bar graph) for each of the ranges. The varying sizes may correlate to the amount of time the user spent in each range. For example, the largest block size in the stacked bar graph may represent the glucose range the user spent the most amount of time in over a specified period of time, while the smallest block size in the stacked bar graph may represent the glucose range the user spent the least amount of time in over a specified period of time.

In a second feature of the user interface view 500, average glucose and standard deviations statistics (e.g., determined by Logic 420C) may be presented to a user. The average glucose and standard deviation may be calculated based on a specified period (e.g., any continuous seven day period).

In a third feature of the user interface view 500, a user's patterns of daytime lows/highs and nighttime lows/highs may be reported. A daytime or nighttime low pattern may be identified in situations where the user has a pattern of low glucose concentration levels around similar times each day in a specified period (e.g., any continuous seven day period). A daytime or nighttime high pattern may be identified in situations where the user has a pattern of high glucose concentration levels around similar times each day in a specified period (e.g., any continuous seven day period).

In a fourth feature of the user interface view 500, a compilation of a user's time in range may be presented in a scatter plot with a line of best fit. The line of best fit expresses the relationship between the data points and identifies a user's time in range trend over a period of time (e.g., a twelve hour period, 12:00 AM-12:00 AM in the example shown) for a specified period (e.g., any continuous seven day period). Additionally, target glucose ranges, for both daytime and nighttime hours, may be provided in the graph. The target glucose ranges may be defined as a different range for daytime and nighttime hours. For example, as shown in the fourth feature, the graph may identify a daytime target glucose range using a figure in the shape of a sun (e.g., daytime range shown in the feature is 80-180 mg/dL) and may identify a nighttime target glucose range using a figure in the shape of a moon (e.g., nighttime range shown in the feature is 90-200 mg/dL). The fourth feature may also provide different color bar graphs to make the distinction between a user's time in a high or very high glucose range, a user's time in a low or very low glucose range, and a user's time in glucose range over a twelve hour period for a specified period.

In a fifth feature of the user interface view 500, a hyperlink may be provided to a user for access to more detailed continuous glucose monitoring (CGM) reports on a website.

In some examples, features one through five may be presented in a vertical format to the user such that feature one may be at the top of the page (e.g., email) and feature five may be at the bottom of the page.

Aspects of the present disclosure provide improvements in data visualization of analyte data, including identifying new patterns and relationships for improved communication of data-driven insights and trends to a user. For example, the present disclosure provides improved methods, such as operations 600 shown in FIG. 6, for generating improved user interface views, shown in FIGS. 7-14F. The user interface views, shown in FIGS. 7-14F are improved in comparison to user interface view illustrated in FIG. 5. For example, additional information is provided that may be used by the user to regulate the user's behavior, such as to control the user's blood glucose concentration levels. While the analyte for measurement and visualization by the devices and methods described herein is glucose, other biological parameters and/or analytes may be considered, as well.

Example Analyte Date Processing and Weekly Report

Figure 6:
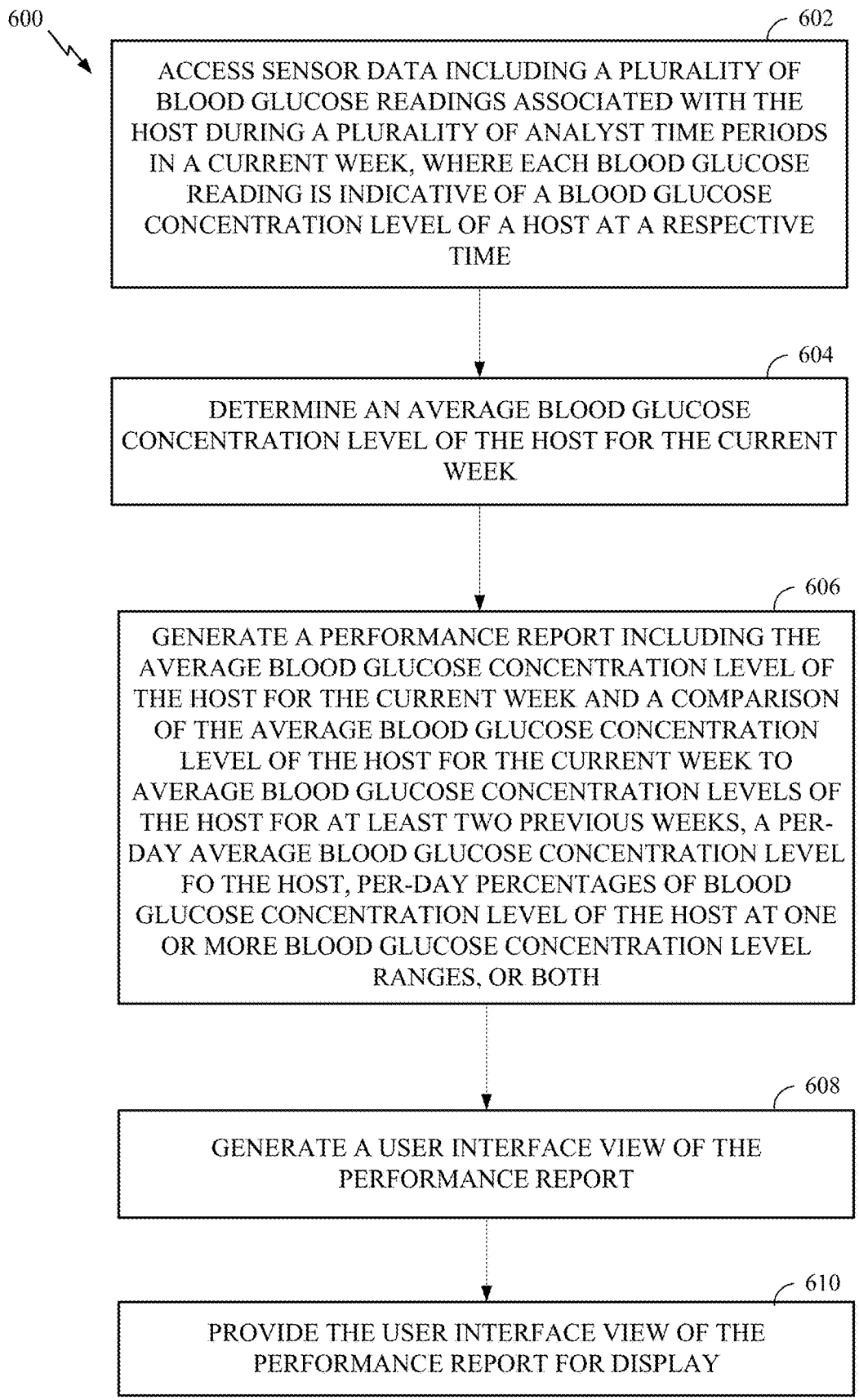
FIG. 6 is a flow diagram illustrating example operations for generating a user interface view associated with sensor data representative of glucose concentration level(s) in a host, in accordance with some example aspects of the present disclosure.

FIG. 6 is a flow diagram illustrating example operations 600 for generating a user interface view associated with sensor data representative of glucose concentration level(s) in a user, in accordance with some example aspects of the present disclosure. Operations 600 may be performed by a processing system, such as the analyte processor 490. In some examples, the operations 600 may be used for generating one or more of the reports illustrated in FIGS. 7-14F and described in more detail below.

Operations 600 may begin, at 602, by accessing sensor data including a plurality of blood glucose readings associated with the user during a plurality of analysis time periods in a current week. Each blood glucose reading is indicative of a blood glucose concentration level of the user at a respective time. In some examples, the plurality of blood glucose readings may be collected by a continuous glucose monitor (CGM) worn by the user. In some examples, the plurality of blood glucose readings may be stored in the repository 475 and accessed by the analyte processor 490.

At 604, operations 600 may include determining an average blood glucose concentration level of the user for the current week. For example, the calculation engine 420H at the analyte processor 490 may compute the average blood glucose concentration level based on the plurality of blood glucose readings.

At 606, operations 600 may include generating a performance report. The performance report may include the average blood glucose concentration level of the user for the current week and a comparison of the average blood glucose concentration level of the user for the current week to average blood glucose concentration levels of the user for at least two previous weeks, a per-day average blood glucose concentration level of the user, per-day percentages of blood glucose concentration level of the user at one or more blood glucose concentration level ranges, or a combination thereof. For example, the performance report may be a weekly performance report (e.g., one of the reports shown in FIGS. 7-14F). The performance report may be generated by the report generator 420G of the analyte processor 490. In some examples, the calculation engine 420H, pattern detector 4201, and/or logic 420C may determine (e.g., compute, process, and/or generate) the information included in the performance report.

At 608, operations 600 may include generating a user interface view of the performance report.

At 610, operations 600 may include providing the user interface view of the performance report for display. In some examples, the user interface view may be provided via email to a user device for display at a user interface. In some examples, the user interface view may provide for display within an application running on a user device for display at a user interface.

Figure 7:
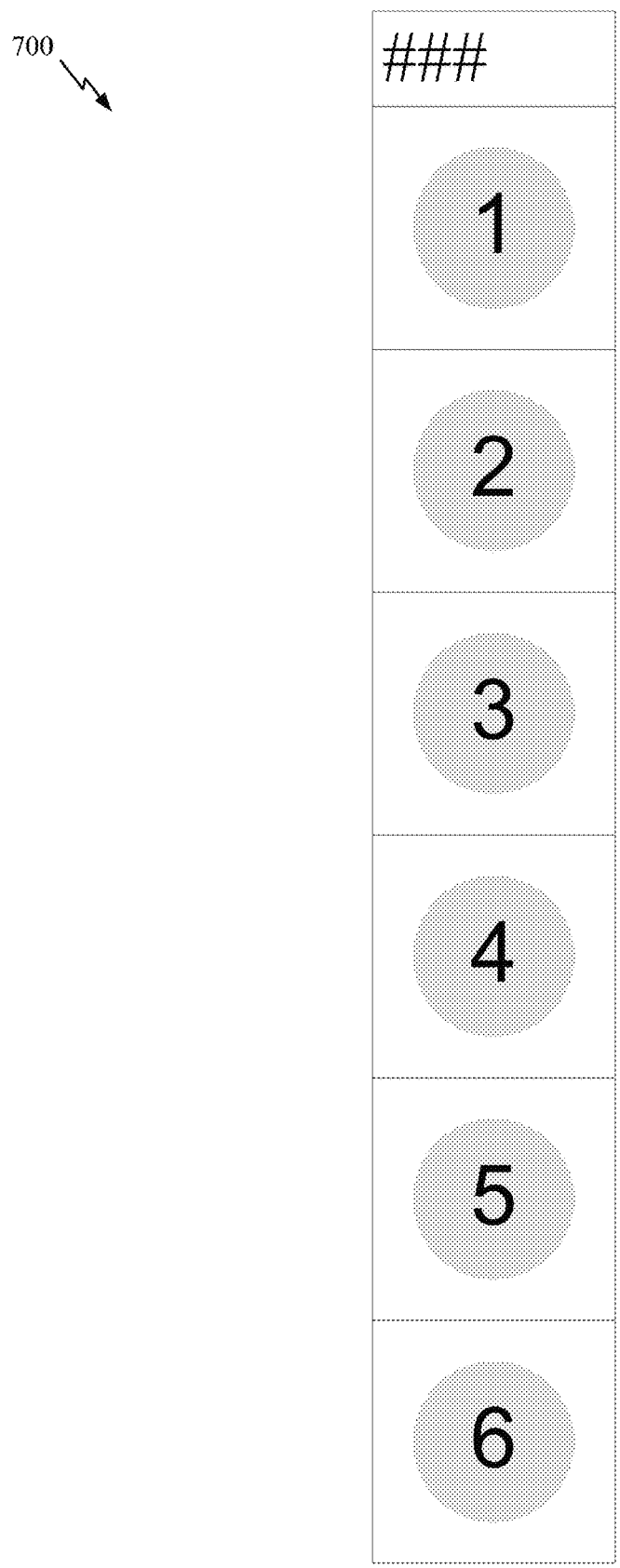
FIG. 7 illustrates an example wireframe of a user interface view in a vertical layout, in accordance with some example aspects of the present disclosure.
Figure 8A:
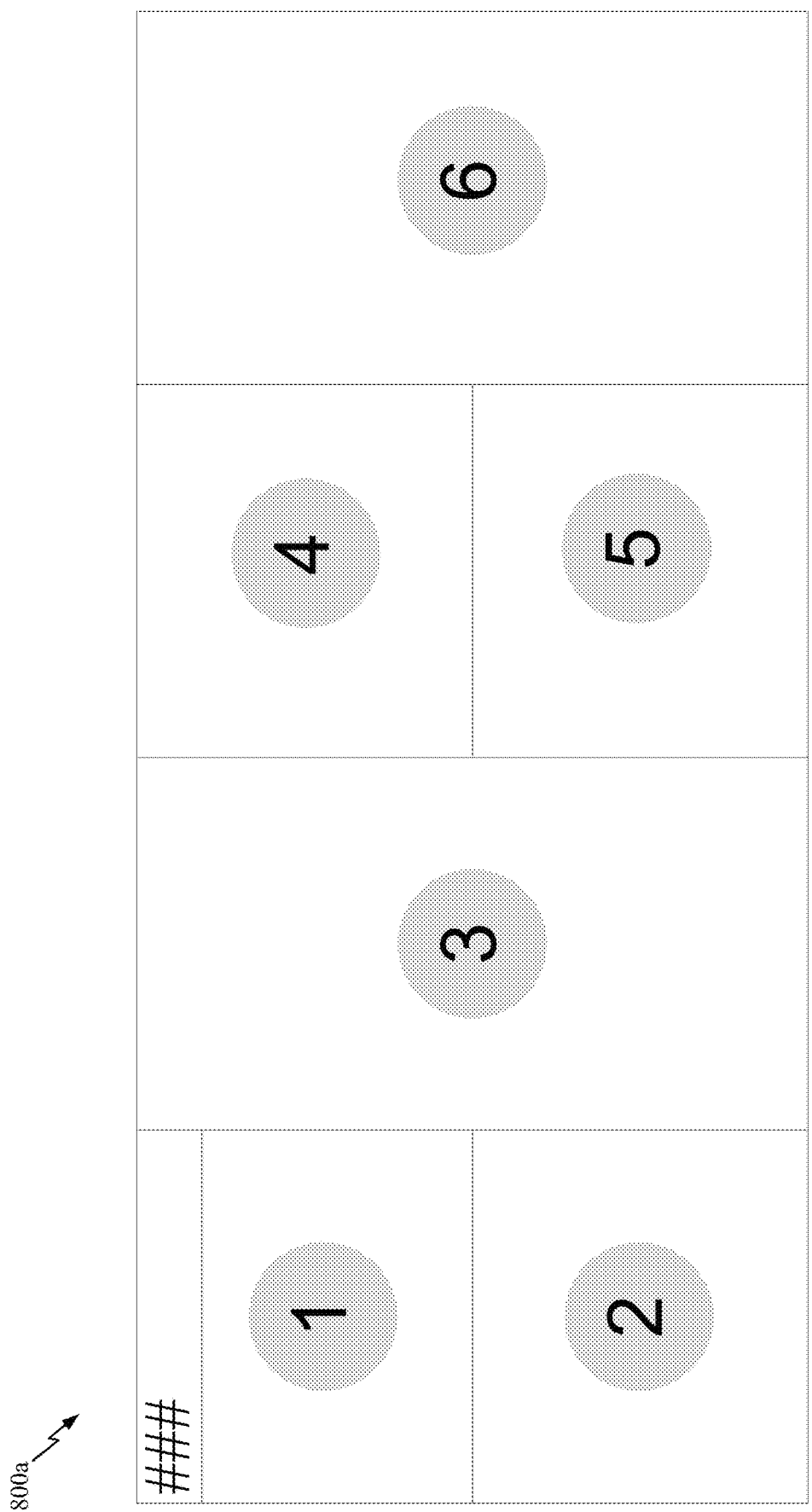
FIG. 8A illustrates an example wireframe of a user interface view in a horizontal layout, in accordance with some example aspects of the present disclosure.

FIG. 7 illustrates an example wireframe 700 of a user interface view in a vertical layout and FIG. 8A illustrates an example wireframe 800a of the user interface view in a horizontal layout, in accordance with some example aspects of the present disclosure. FIGS. 8B-8G illustrate enlarged views of features (e.g., modules) one through six shown in the vertical and horizontal wireframes, 700 and 800a, respectively, and are described in more detail further below.

Figure 8B:
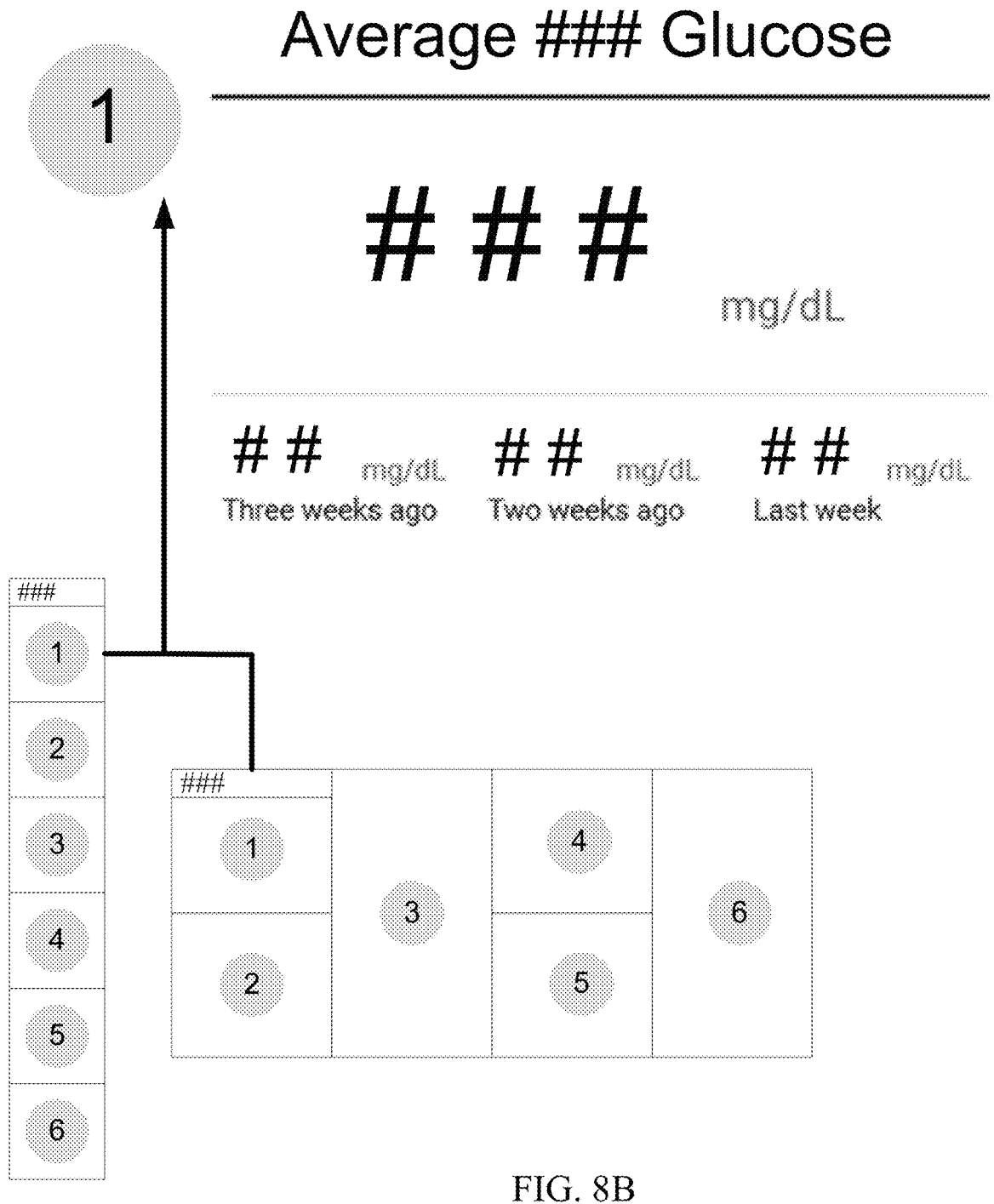
Figure 8C:
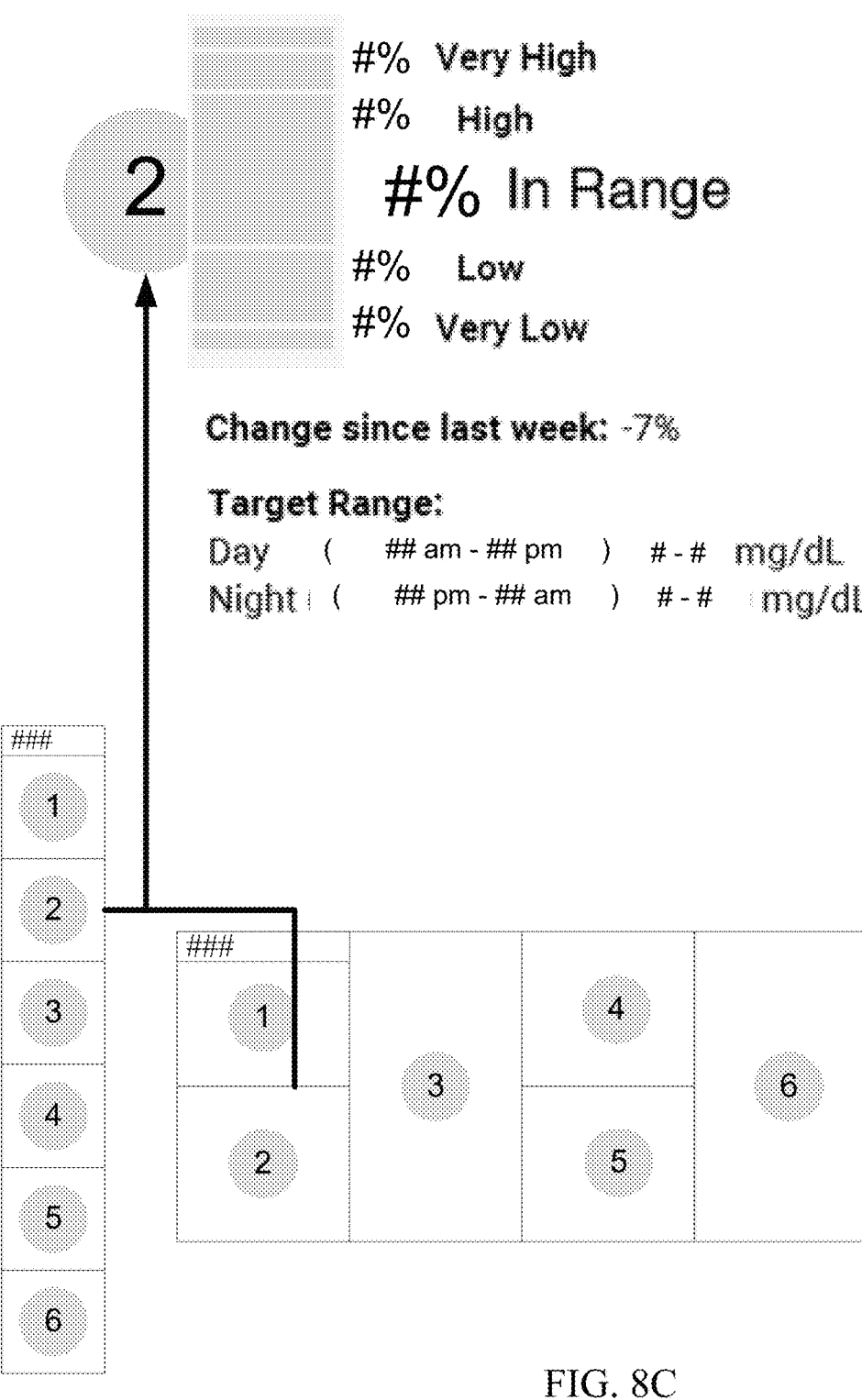
Figure 8D:
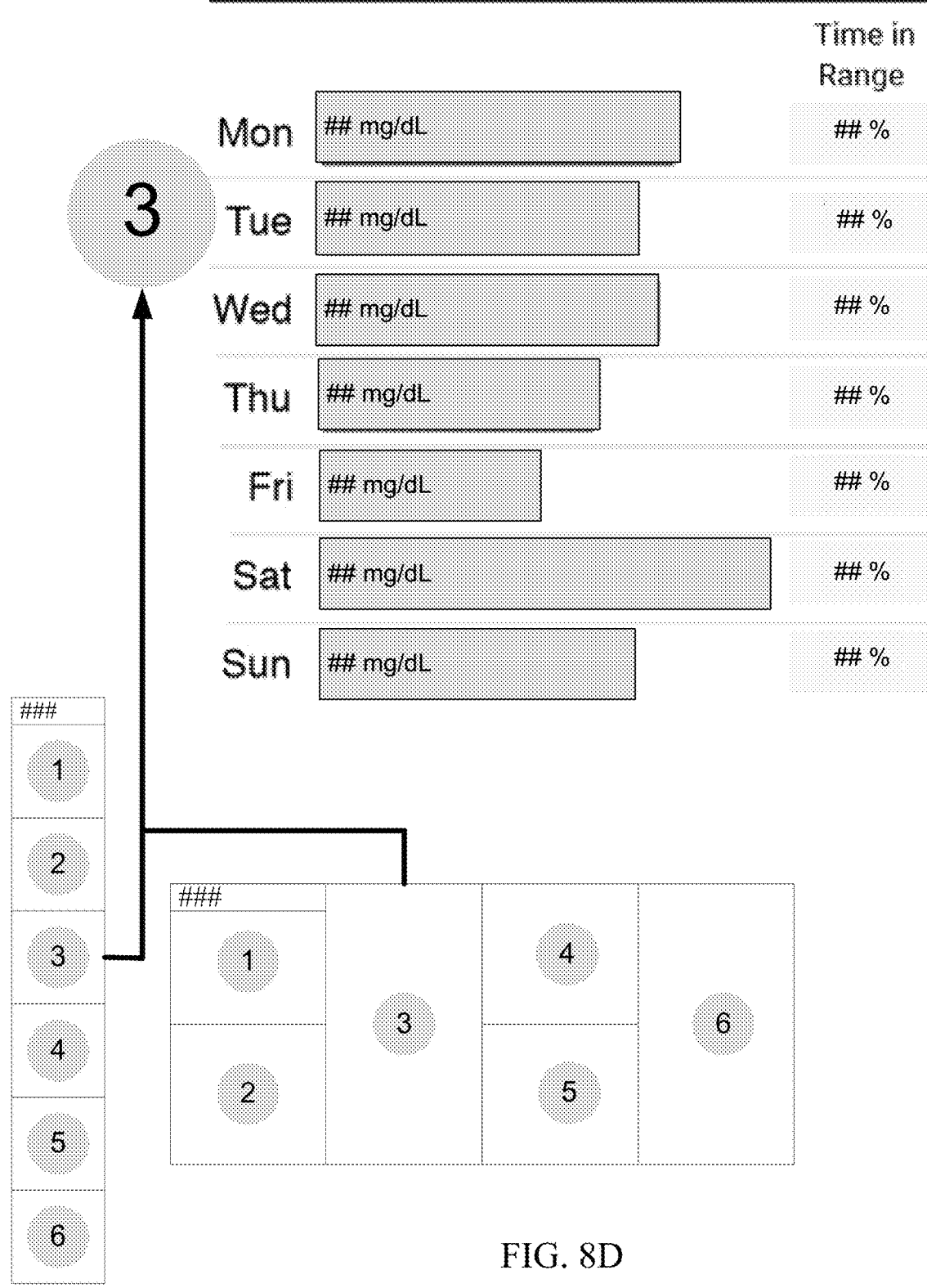
Figure 8F:
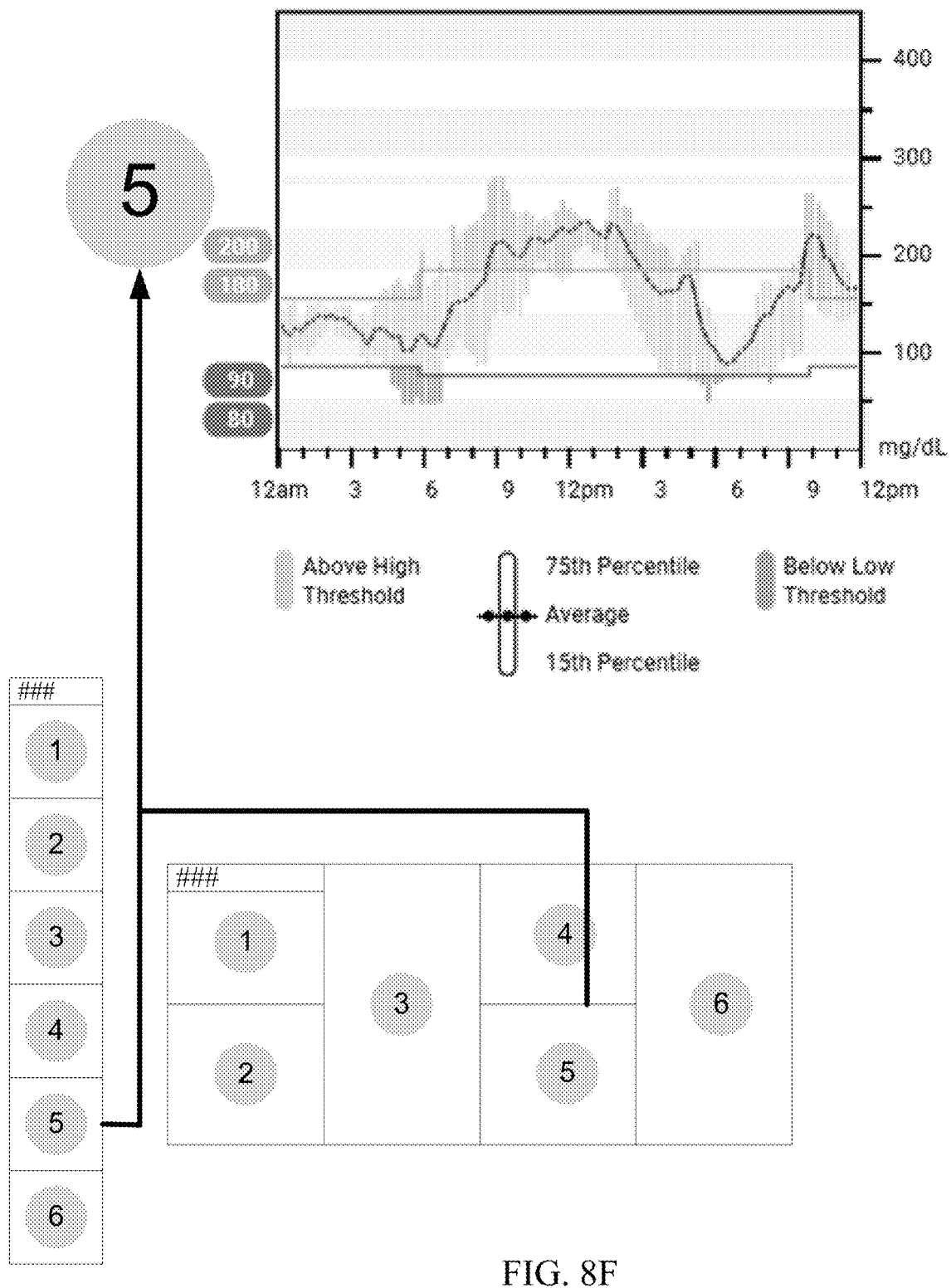
Figure 9:
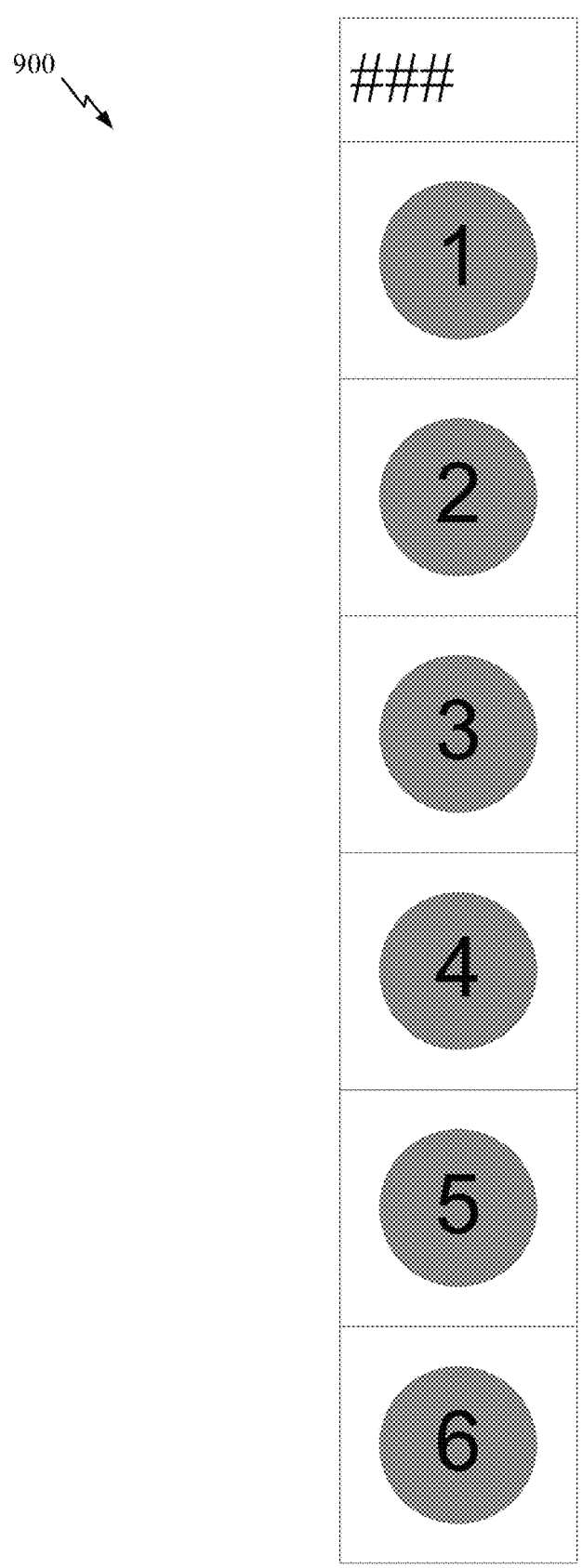
FIG. 9 illustrates an example user interface view associated with sensor data representative of glucose concentration level(s) in a host in a vertical layout which corresponds to the wireframe of FIG. 7, in accordance with some example aspects of the present disclosure.
Figure 10A:
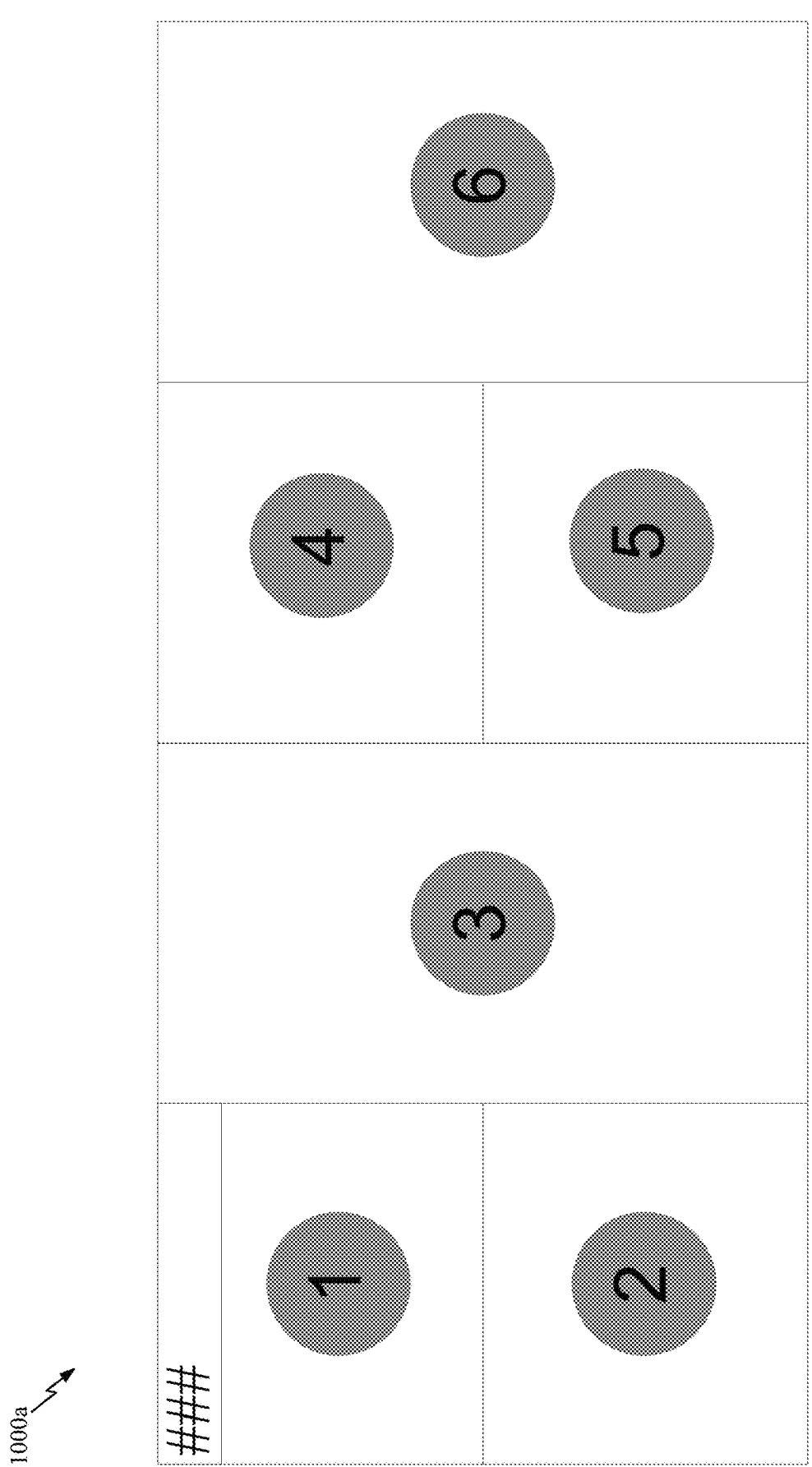
FIG. 10A illustrates an example user interface view associated with sensor data representative of glucose concentration level(s) in a host in a horizontal layout which corresponds to the wireframe of FIG. 8A, in accordance with some example aspects of the present disclosure.

FIG. 9 illustrates an example user interface view 900 associated with sensor data representative of glucose concentration level(s) in a user in a vertical layout which corresponds to the wireframe 700 of FIG. 7 and FIG. 10A illustrates an example user interface view 1000a in a horizontal layout which corresponds to the wireframe 800a of FIG. 8, in accordance with some example aspects of the present disclosure. FIGS. 10B-10G illustrate enlarged views of features one through six shown in the vertical and horizontal user interface views, 900 and 1000a, respectively, and are described in more detail further below.

A horizontal or vertical display of the user interface view may be based on a type or configuration of a user device. For example, a vertical layout may be useful for a phone, tablet, or other smaller user device, while a horizontal layout may be useful for a desktop computer or a laptop computer. Although both horizontal and vertical orientations are shown, only one orientation may be displayed to the user. In some aspects, the orientation of the user interface view may be automatically selected and displayed based on a type of a user device.

Figure 10B:
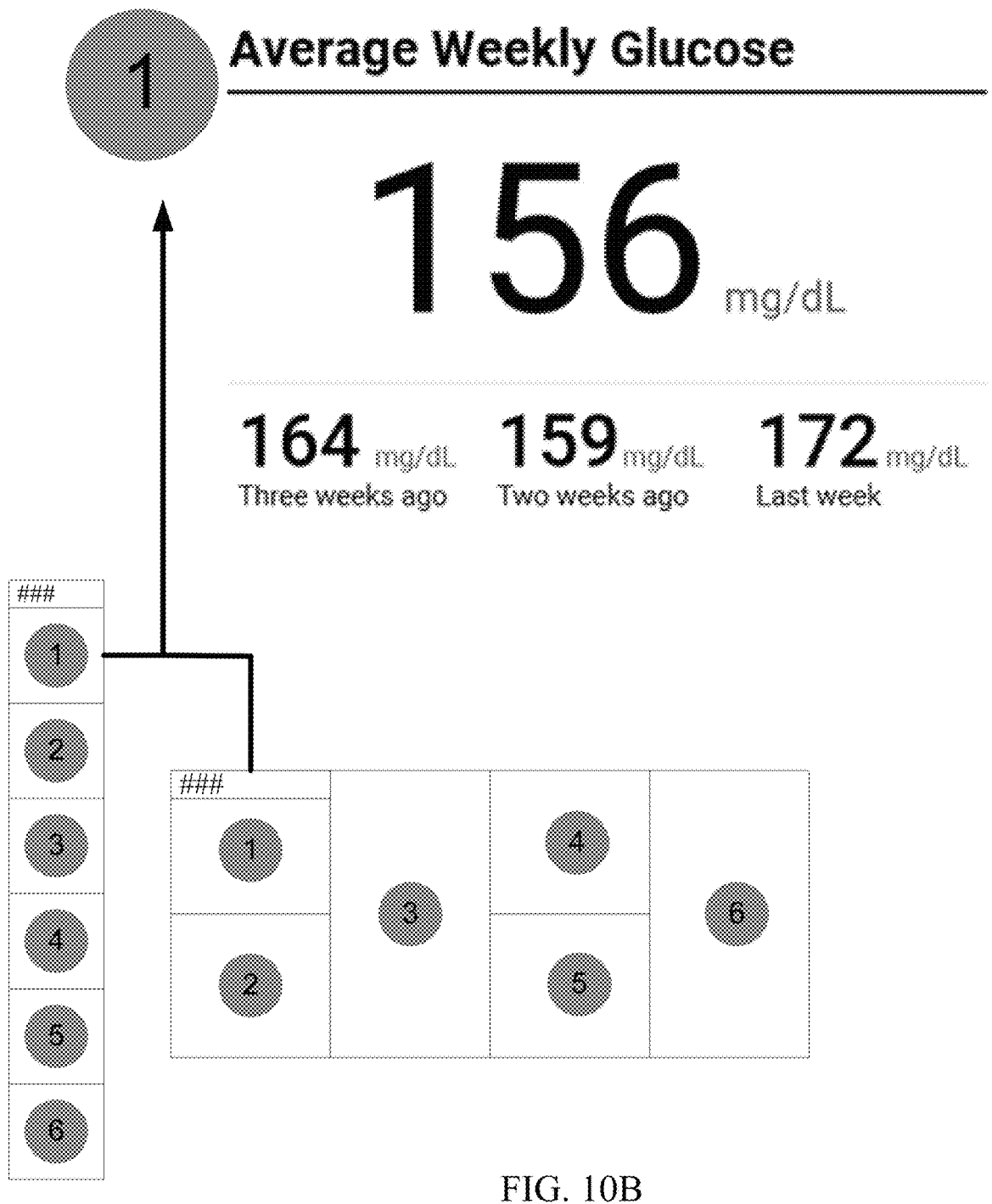
FIGS. 10B-10G illustrate enlarged views of features one through six shown in the vertical and horizontal user interface views of FIG. 9 and FIG. 10A, respectively, in accordance with some example aspects of the present disclosure.
Figure 10C:
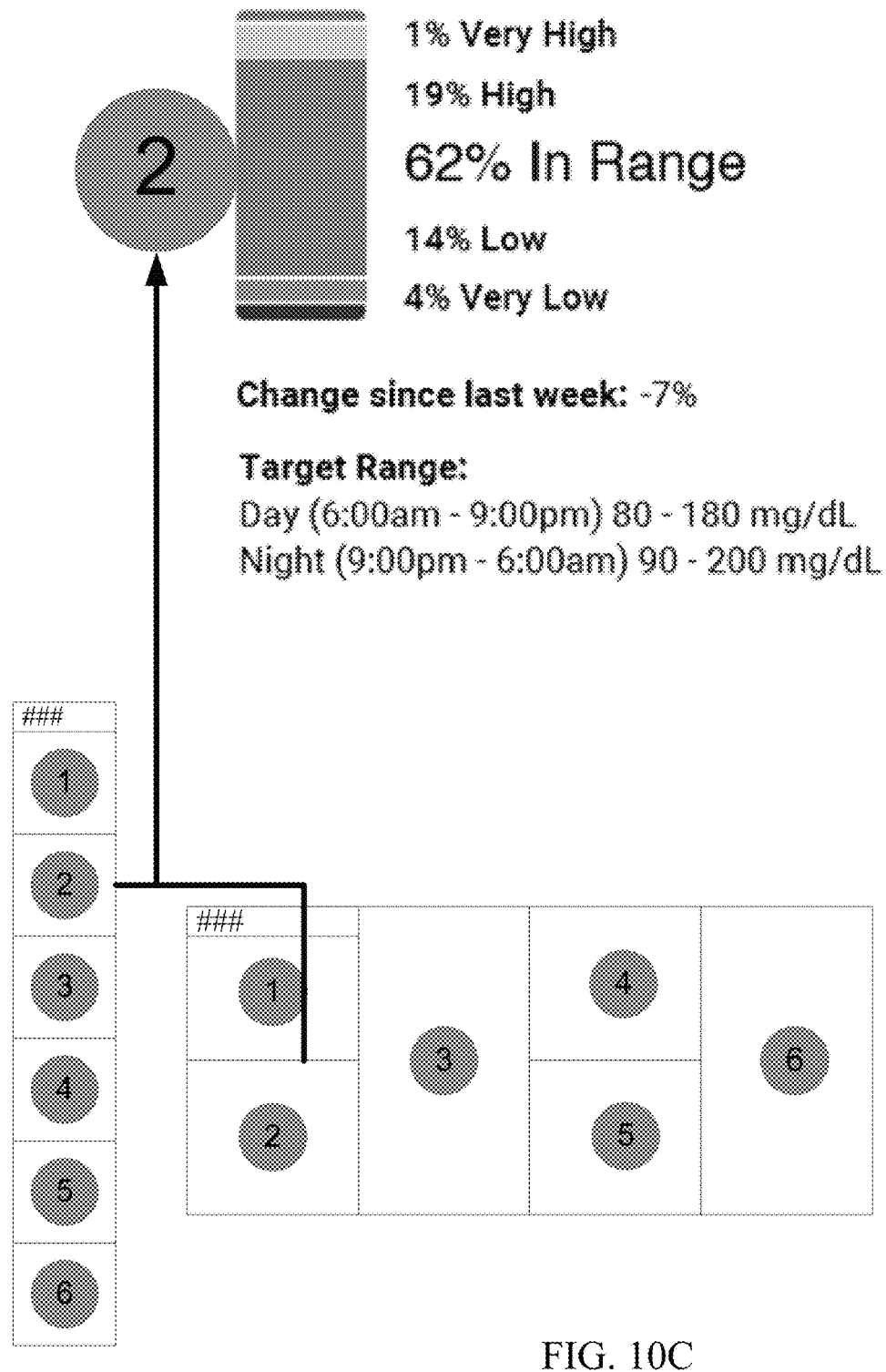
Figure 10D:
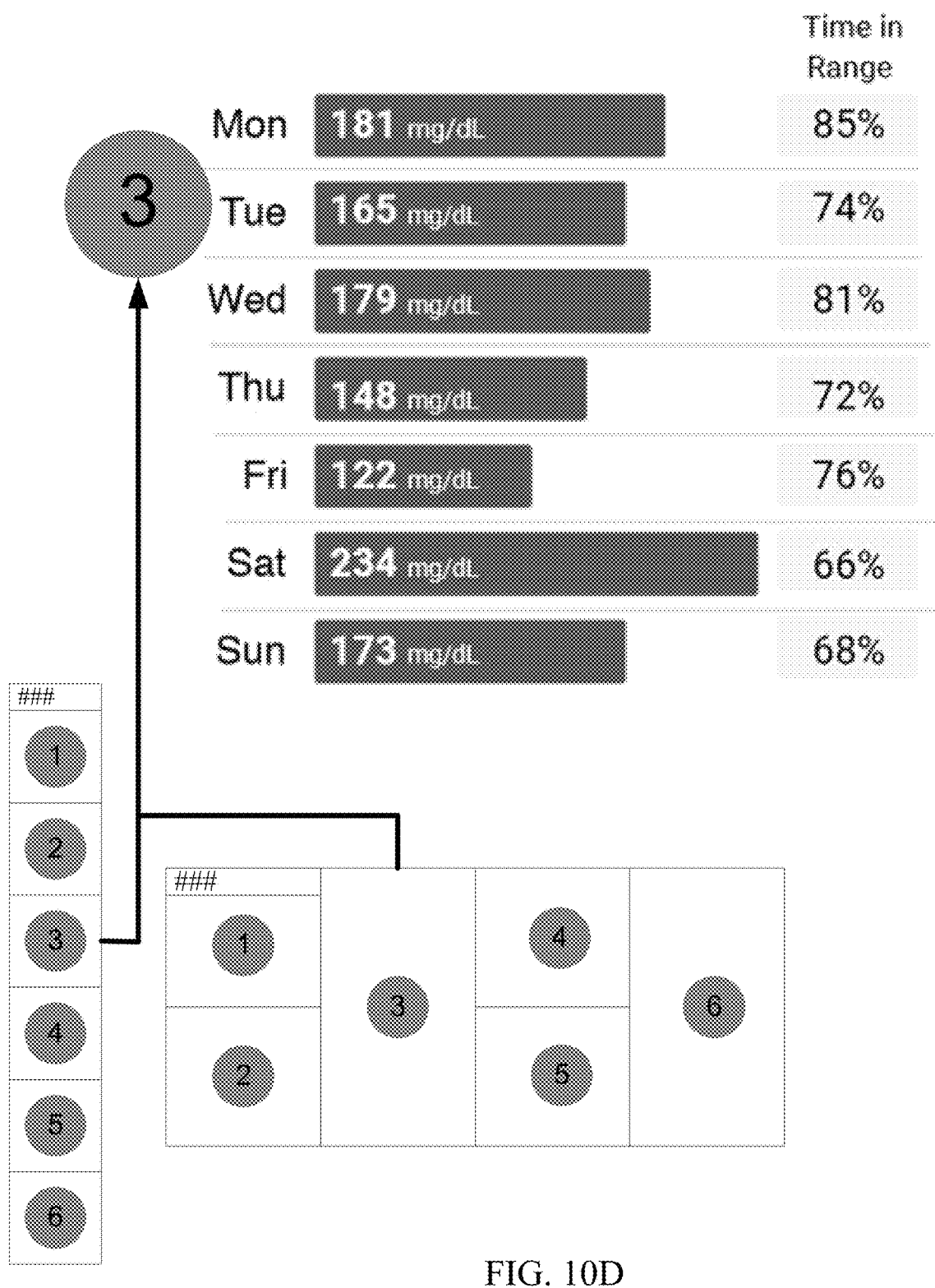
Figure 10E:
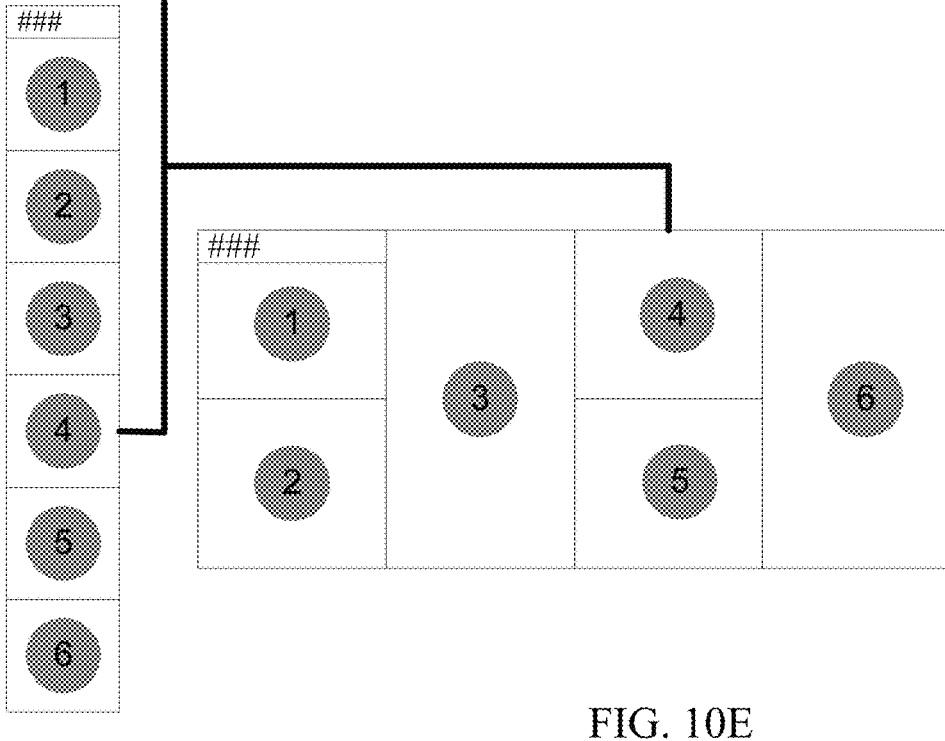
Figure 10F:
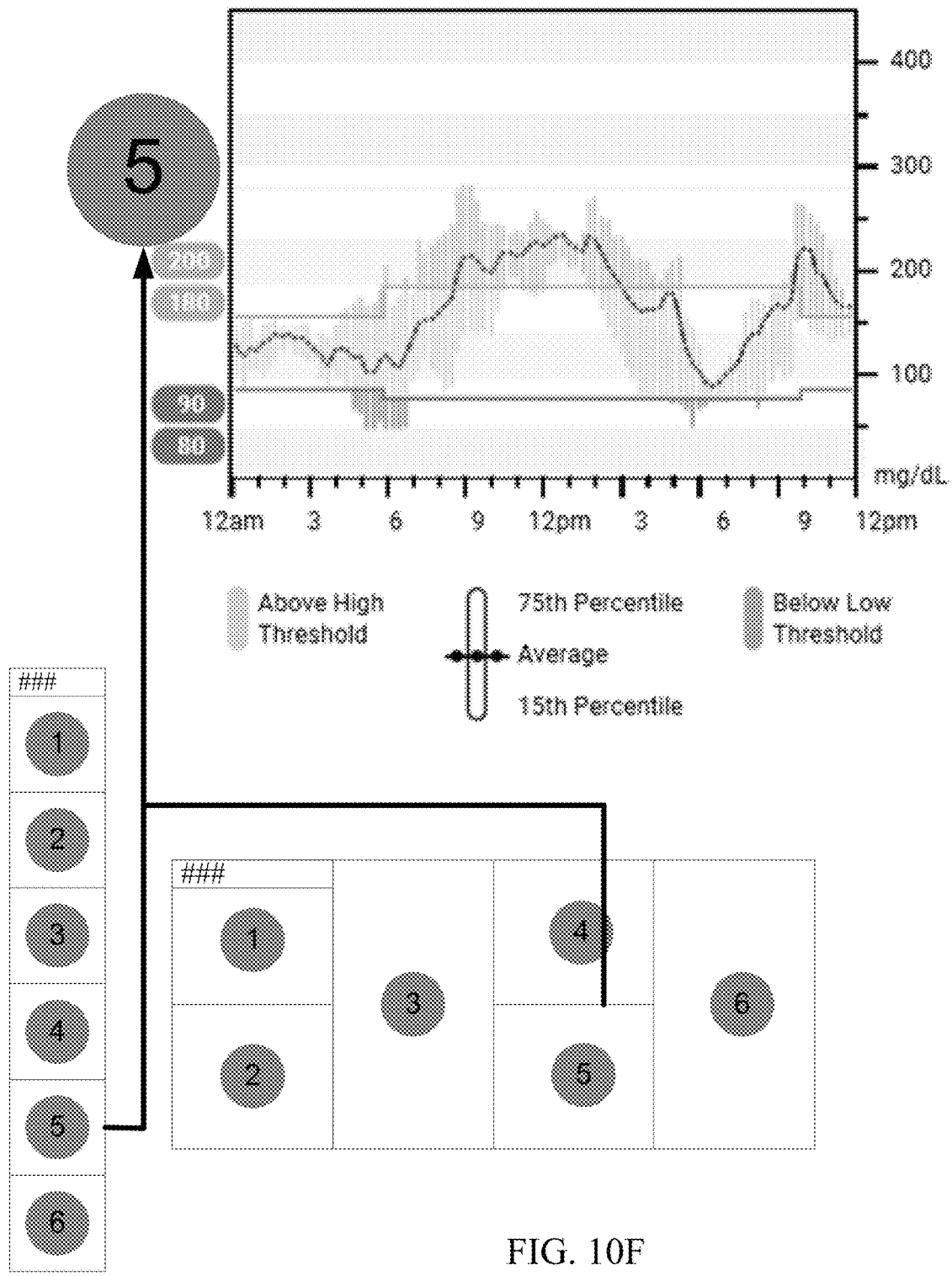
Figure 10G:
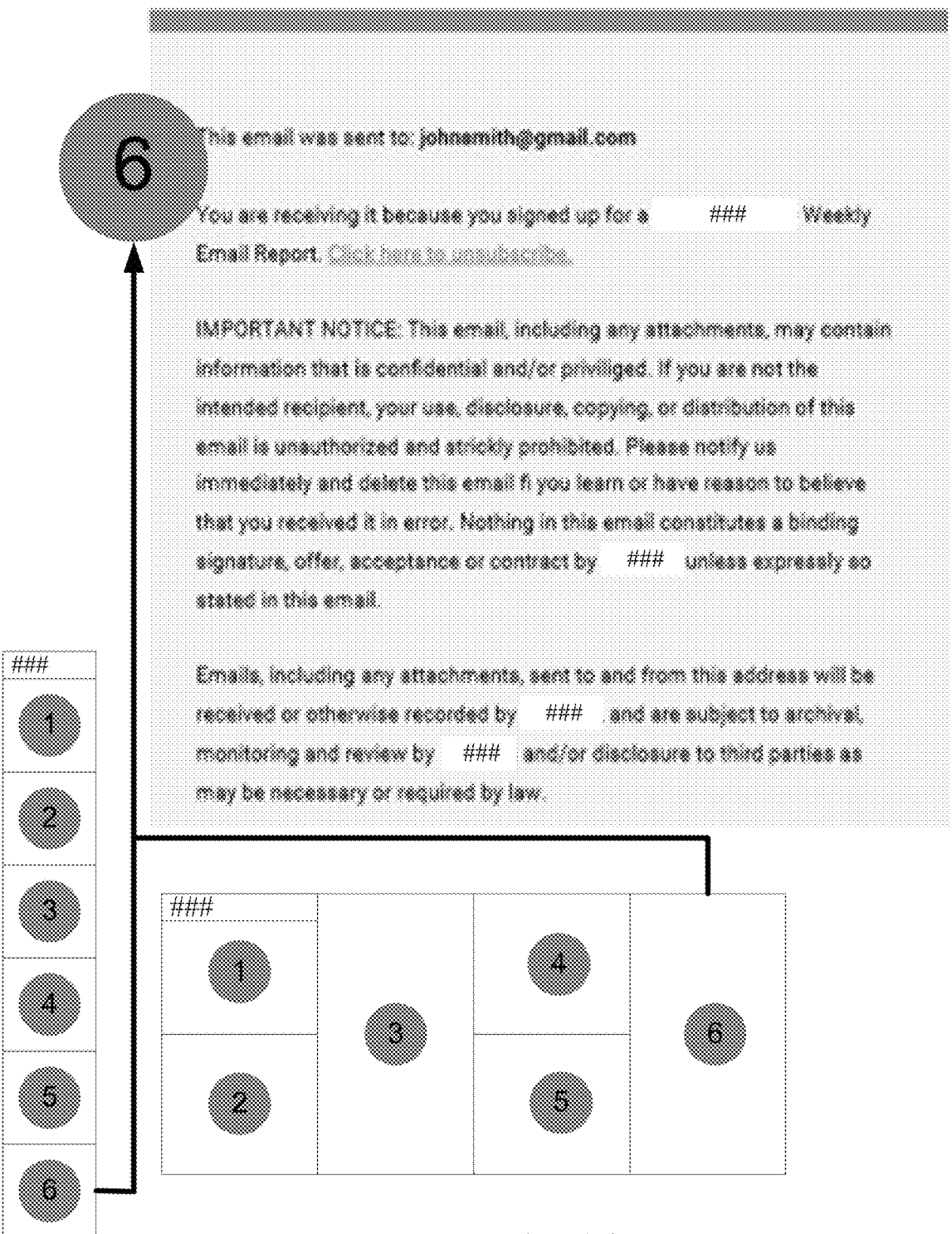

As shown in the example user interface views of FIGS. 9-10G, and corresponding wireframes of FIGS. 7-8G, a weekly report may be provided to a user of a diabetes management application to provide relevant insights into a user's retrospective glucose values, patterns, and/or trends over time.

The report may provide an average weekly glucose for one or more time ranges (e.g., weeks). The time range and the number of time ranges may be configurable. The average weekly glucose may be computed by calculation engine 420H and/or logic 420C of FIG. 4. As shown in FIGS. 8B and 10B, in a first feature 800b, 1000b of wireframes 700, 800a and user interface views 900, 1000a, a visualization comparing an average blood glucose concentration level of a user for the current week to average blood glucose concentration levels of the user for at least two previous weeks (e.g., average blood glucose concertation level three weeks ago, two weeks ago, and last week) may be provided.

As shown in FIGS. 8B and 10B, a first feature 800b, 1000b of wireframes 700, 800a and user interface views 900, 1000a may further provide a date associated with the time range (e.g., Sep. 6, 2020 through Sep. 11, 2020) for the user's average glucose (e.g., 156 mg/dL in the example in FIG. 10B). To provide context to this glucose average, the user's average glucose may be compared to an average glucose calculated for one or more previous weeks (e.g., "Last week", "Two weeks ago", "Three weeks ago" in the example in FIG. 10B). This comparison visualization may provide insight on the user's blood sugar consistency, improvement, and/or poor performance over multiple weeks.

As shown in FIGS. 8D and 10D, a third feature 800d, 1000d of wireframes 700, 800a and user interface views 900, 1000a may provide a visualization comparing the per-day average blood glucose concentration levels of a host and the per-day percentages of blood glucose concentration levels of a host at one or more blood glucose concentration level ranges. The per-day average blood glucose concentration levels may be computed by calculation engine 420H and/or logic 420C of FIG. 4 based on continuously monitored blood glucose data. The report may also provide per-day percentages of blood glucose concentration levels of a user at one or more blood glucose concentration level ranges. For example, pattern detector 4201, calculation engine 420H, and/or logic 420C of FIG. 4 may compare blood glucose concentration level data throughout the course of a 24 hour period to a predetermined target or "normal" blood glucose concentration level value or range to identify periods in which the user's blood glucose concentration level is "in range" or "out of range". The analyte processor can then determine a percentage of time during a 24 hour period that the user's blood glucose concentration level was "in range" (referred to herein as "time in range" or "TIR").

As shown in FIGS. 8D and 10D, a day-by-day bar graph may be presented to illustrate the user's blood glucose concentration levels. A day-by-day breakdown may allow the user to understand their problem days throughout the week and adjust their lifestyle, diet, or other associated factors accordingly. The visualization may also provide a percentage of time in range per day to provide additional context to the user's average daily glucose concentration levels. For example, as shown in FIG. 10D, on Saturday the host may experience their highest average glucose of the week at 234 mg/dL. With a corresponding 66% time in the target glucose range, the user may be able to conclude that a majority of the time outside of their target range was spent in a high or very high glucose range (instead of a low or very low glucose range).

As shown in FIGS. 8G and 10G, a sixth feature 800g, 1000g of wireframes 700, 800a and user interface views 900, 1000a may be a button provided to re-direct the user to a website or an application (app) on the user's device that provides the user's and/or host's more detailed continuous glucose monitoring (CGM) reports. Whether the button re-directs the user to a website or redirects the user to an app may depend on the type or configuration of the user device being used to display the button. Unlike the hyperlink of feature five in FIG. 5, the button may be larger than the hyperlink thereby capturing the user's attention and encouraging greater interaction between the user and the user interface.

A second feature 800c, 1000c shown in FIGS. 8C and 10C, a fourth feature 800e, 1000e shown in FIGS. 8E and 10E, and a fifth feature 800f, 1000f shown in FIGS. 8F and 10F of wireframes 700, 800a and user interface views 900, 1000a, corresponding to the time in range stacked bar graph, the patterns summary, and the trends summary, may be similar to features one, three, and four depicted in FIG. 5.

In some examples, features one through six of wireframes 700, 800a and user interface views 900, 1000a may be presented chronologically: from top to bottom, as shown in the vertical layouts of FIGS. 7 and 9, or from left to right, as shown in the horizontal layouts in FIGS. 8A and 10A. In some examples, feature one may be stacked on top of feature two in the horizontal layout. In some examples, feature four may be stacked on top of feature five in the horizontal layout. In some example, features one through six may be presented in any random order.

Figure 11A:
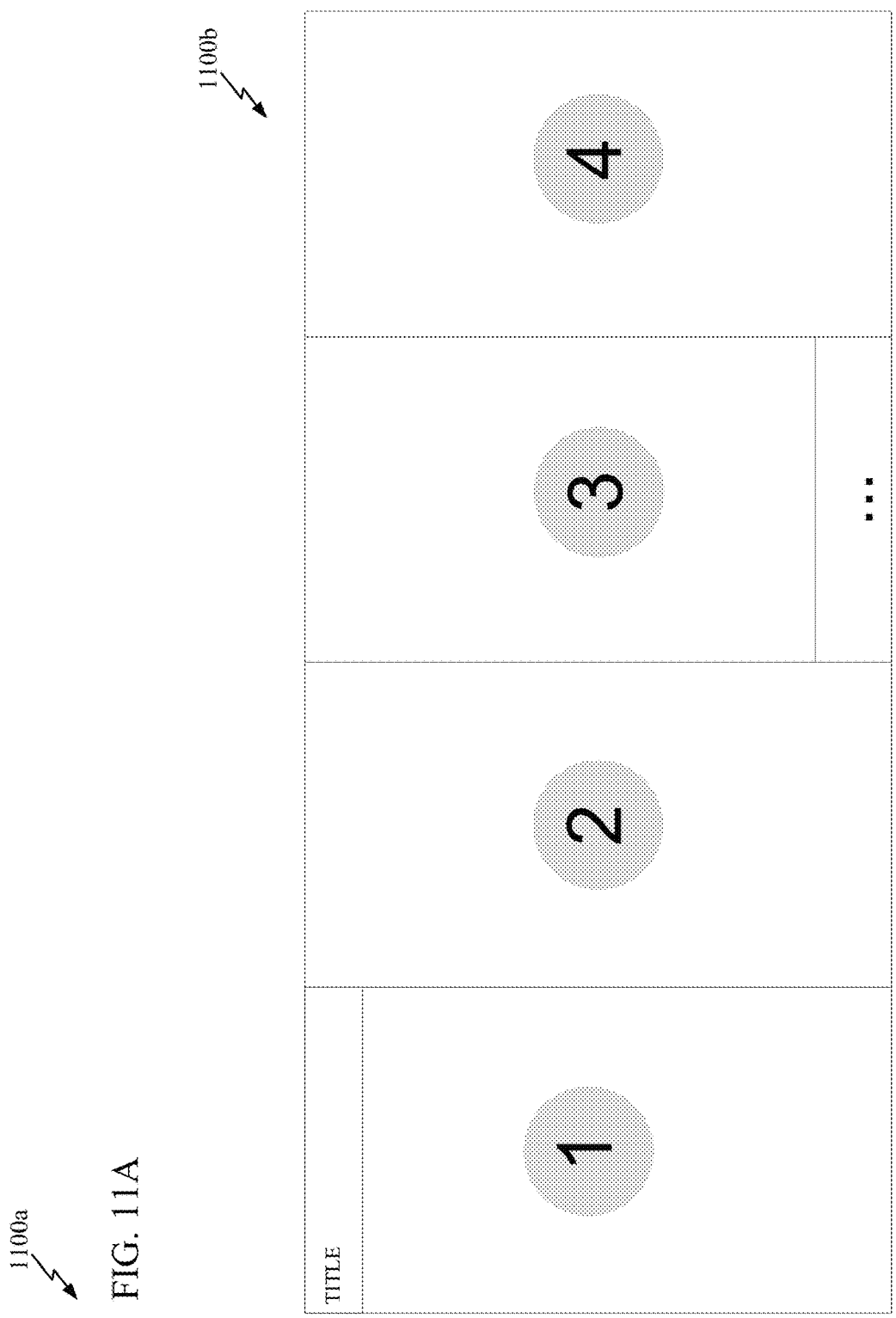
FIG. 11A illustrates an example wireframe of another example user interface view in a vertical layout, in accordance with some example aspects of the present disclosure.
Figure 11B:
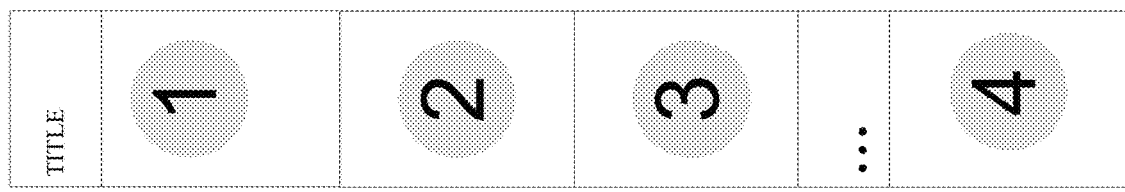
FIG. 11B illustrates an example wireframe of another user interface view in a horizontal layout, in accordance with some example aspects of the present disclosure.

FIG. 11A illustrates an example wireframe 1100a of another example user interface view in a vertical layout, and FIG. 11B illustrates an example wireframe 1100b of the user interface view in a horizontal layout, in accordance with some example aspects of the present disclosure. FIGS. 11C-11F illustrate enlarged views of features one through four shown in the vertical and horizontal wireframes, 1100a and 1100b, respectively, and are described in more detail further below.

Figure 12C:
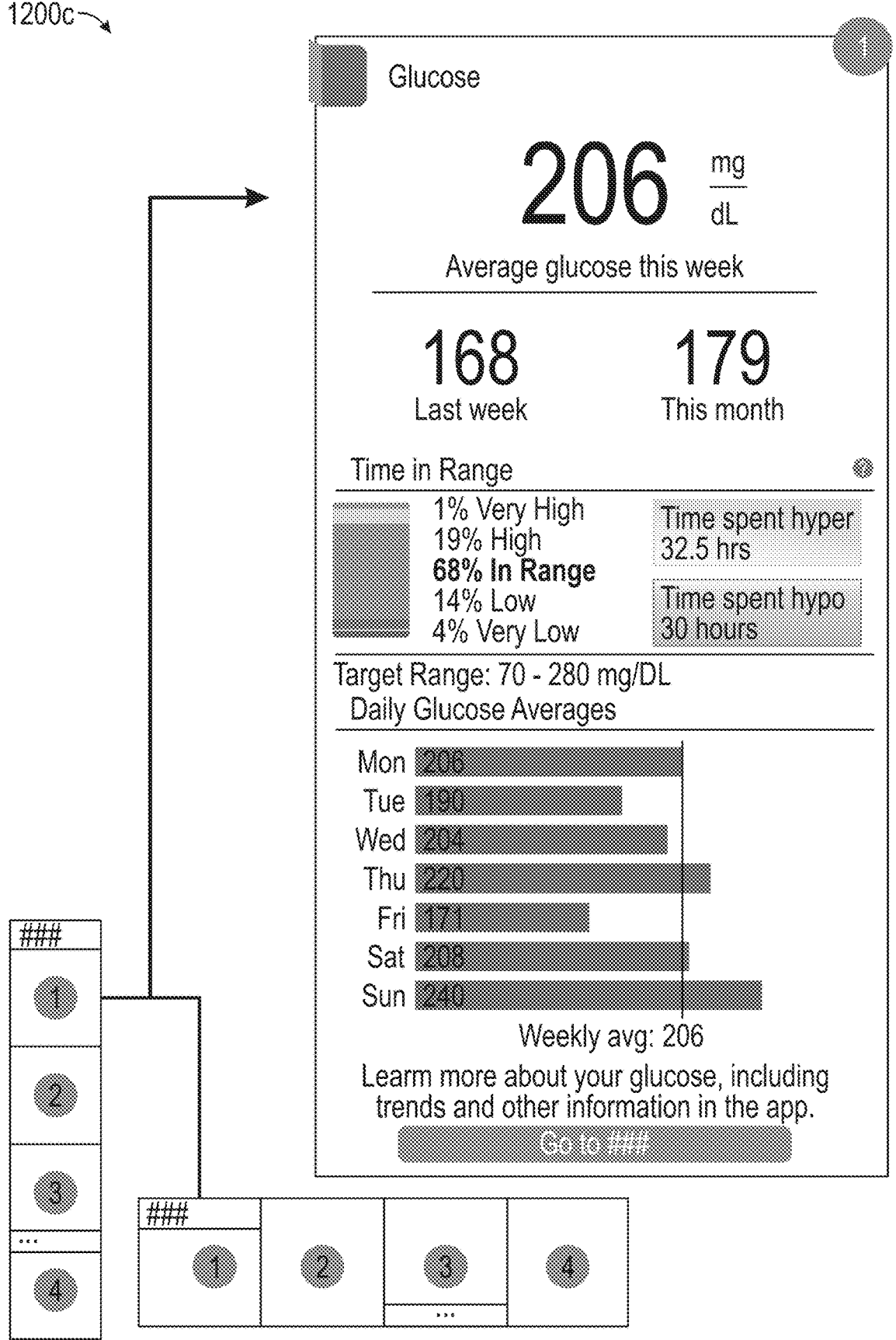

FIG. 12A illustrates an example user interface view 1200a associated with sensor data representative of glucose concentration level(s) in a user in a vertical layout which corresponds to the wireframe 1100a and FIG. 12B illustrates an example user interface view 1200b in a horizontal layout which corresponds to the wireframe 1100b, in accordance with some example aspects of the present disclosure. FIGS. 12C-12G illustrate enlarged views of features one through four shown in the vertical and horizontal user interface views, 1200a and 1200b, and are described in more detail further below.

Although both horizontal and vertical orientations are shown, only one orientation may be displayed to the user. In some aspects, the orientation of the user interface view may be automatically selected and displayed based on a type of a user device.

As shown in the example user interface views of FIGS. 12A and 12B, and corresponding wireframes of FIGS. 11A and 11B, a weekly report may be feature based, beginning with glucose and adding other interchangeable elements, to provide relevant insights into a user's retrospective glucose values, patterns, and trends over time with respect to other factors such as insulin, meals, and/or other factors which may affect the user's glucose levels. In some examples, a user may be able to switch the presented categories on the user interface by interacting with a button provided on the user interface view (e.g., "Switch it up!" button provided in FIG. 12G).

Figure 11C:
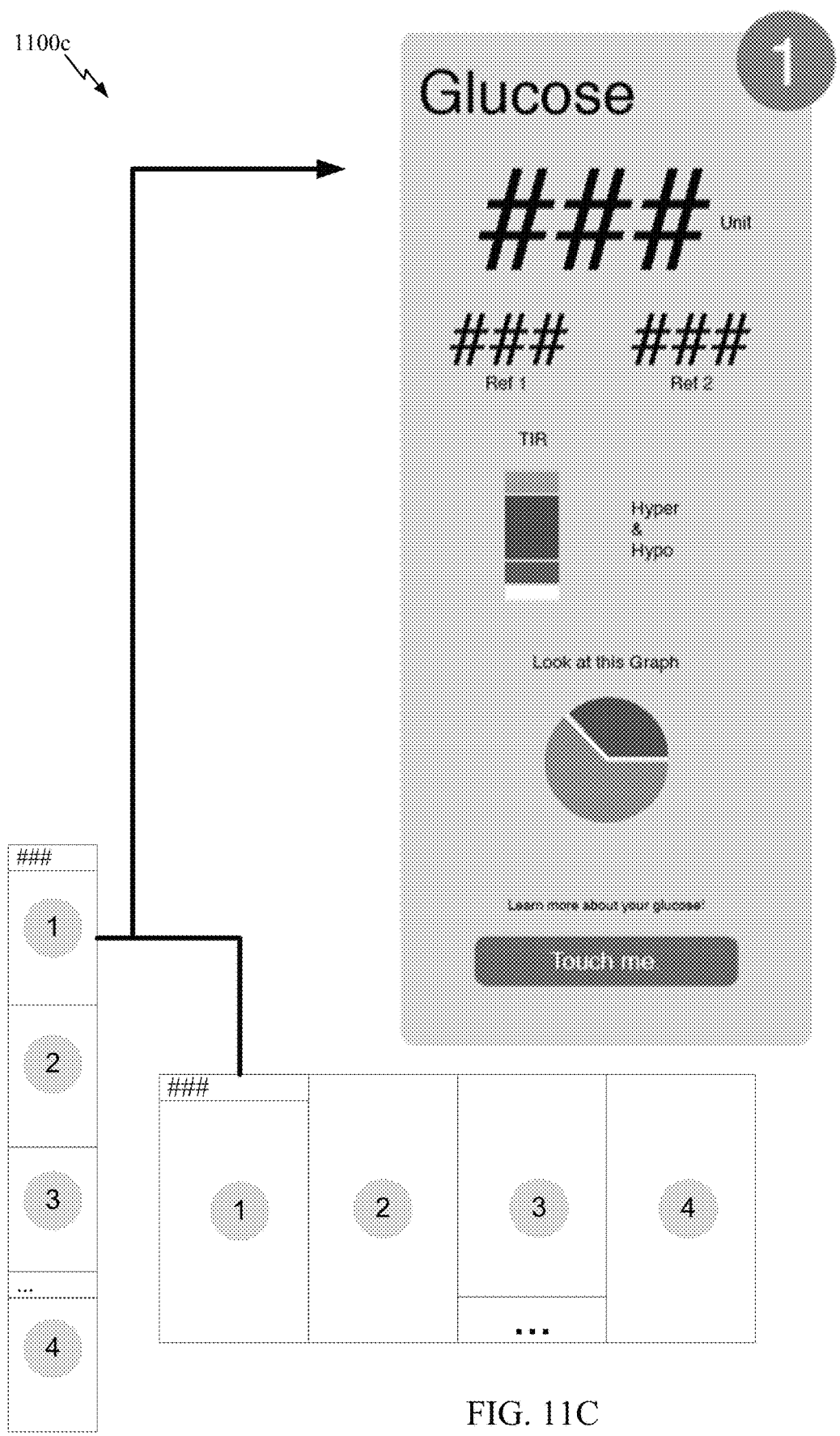
FIGS. 11C-11F illustrate enlarged views of features one through four shown in the vertical and horizontal wireframes of FIG. 11A and FIG. 11B, respectively, in accordance with some example aspects of the present disclosure.

As shown in FIGS. 11C and 12C, in a first feature 1100c, 1200c of wireframes 1100a, 1100b and user interface views 1200a, 1200b, information related to the user's glucose levels over a specified time period may be provided. The glucose information may include an average glucose (e.g., determined by Logic 420C of FIG. 4) for the current week in comparison to a previous week's average glucose and the month's average glucose, a time in range stacked bar graph broken down into blocks (stacked on top of each other) which each correlate to the user's time spent in a target glucose range, a very high glucose range, a high glucose range, a low glucose range, and a very low glucose range, a summary of the number of hours a user has spent in hyper (e.g., hyperglycemia, when the user's blood sugar is too high) and hypo (e.g., hypoglycemia, when the user's blood sugar is too low) during a specified period (e.g., a week), a day-by-day bar graph of the user's average glucose levels in comparison to a weekly average, and a button re-directing the user at the user interface to be re-directed to a website housing detailed CGM reports.

Figure 11D:
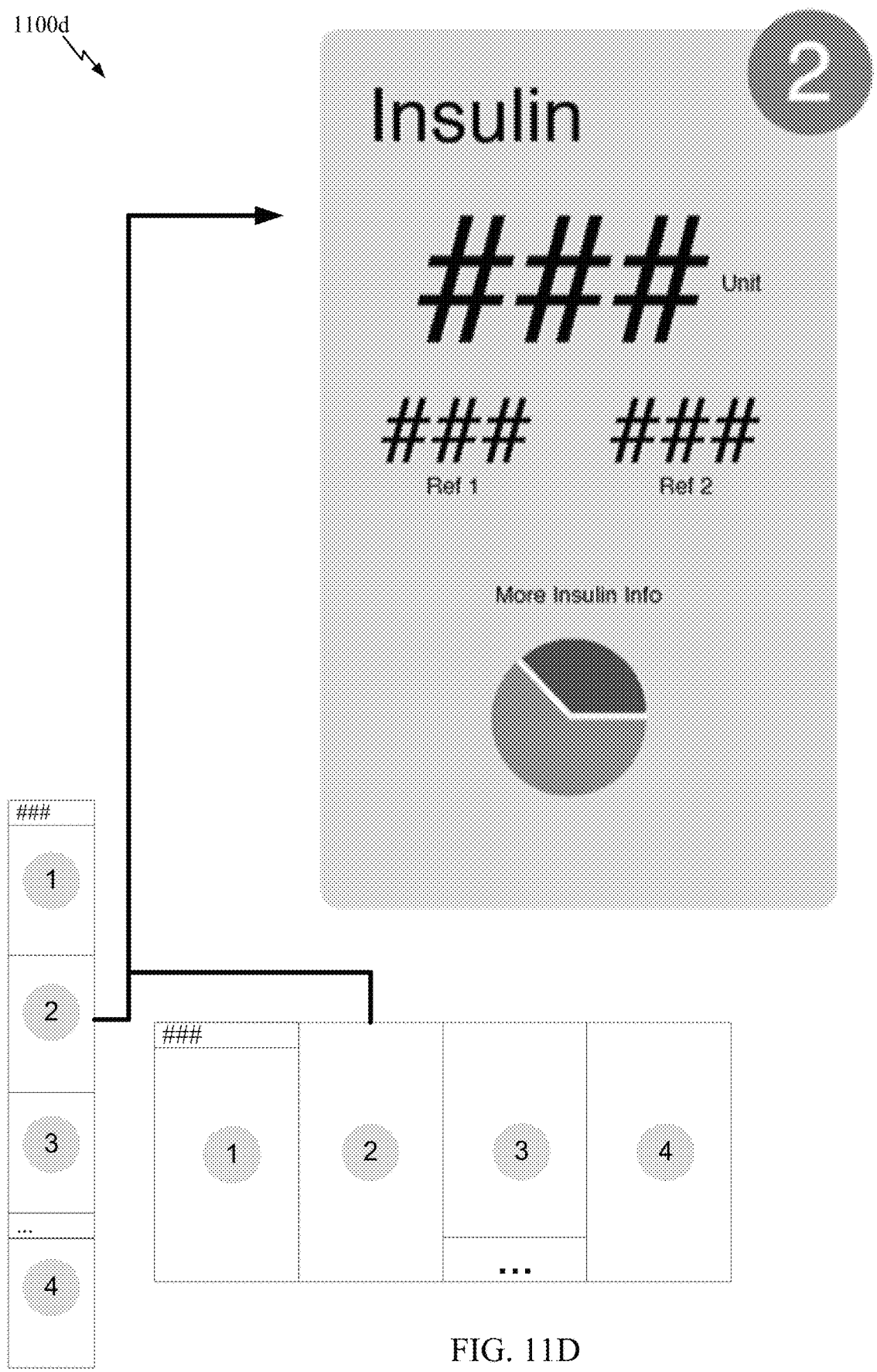
Figure 12D:
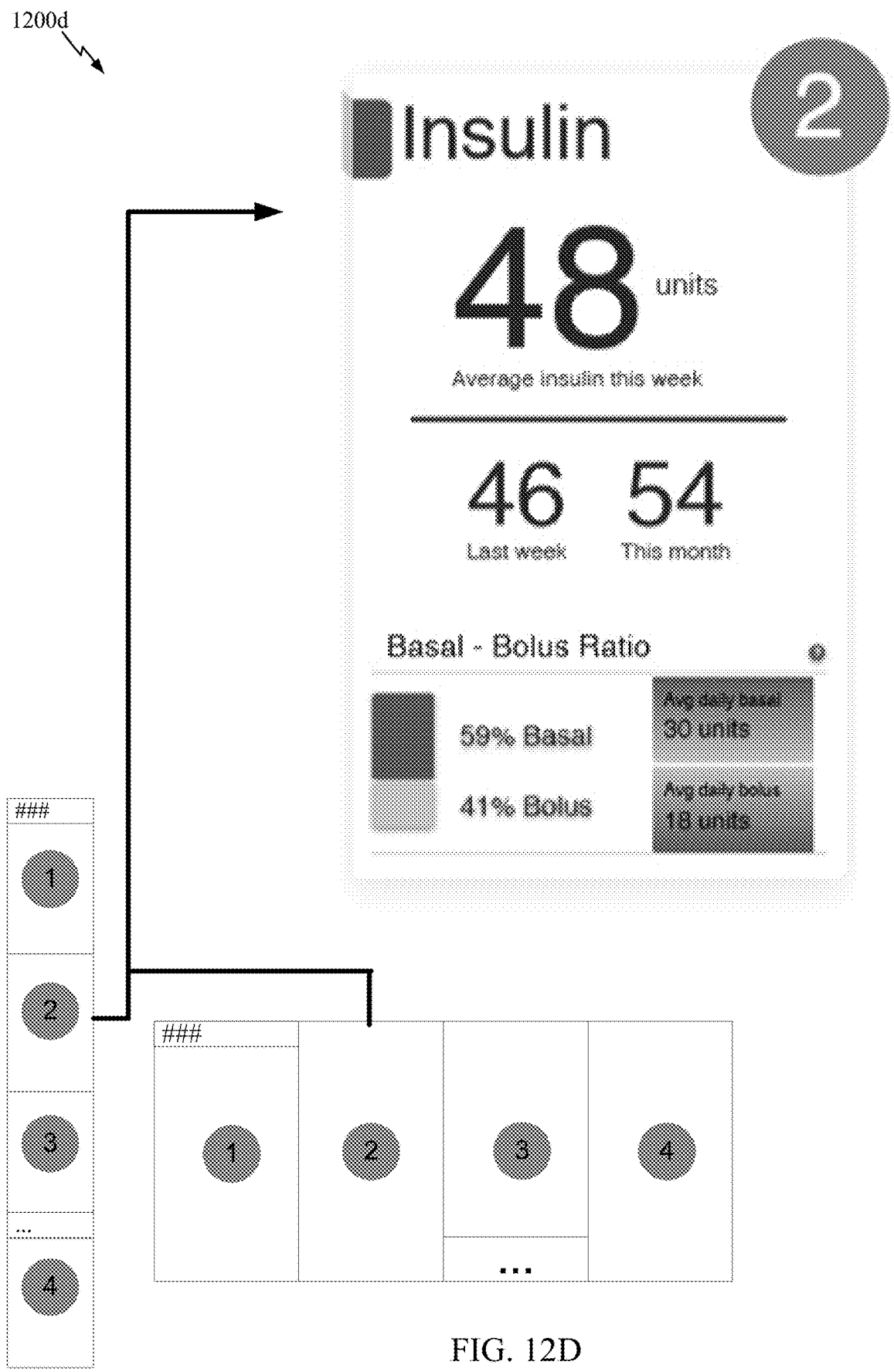

As shown in FIGS. 11D and 12D, in a second feature 1100d, 1200d of wireframes 1100a, 1100b and user interface views 1200a, 1200b, information related to the host's insulin levels over a specified time may be provided. The insulin information may include an average number of insulin units taken by the user. For example, the average number of insulin units for the current week may be compared to a previous week's average insulin units and the month's average insulin units. Further, a stacked bar graph illustrating the user's basal insulin intake to bolus insulin intake and a user's average daily basal and bolus units may be provided in the second feature. As used herein, basal is an hourly drip of insulin which replaces long lasting insulin, and bolus is an extra dose that is given for the food eaten and to correct the blood sugar where a user's blood sugar is high. The analyte processor 490 may determine average insulin amounts based on information input by the user, information automatically uploaded and collected, etc.

Figure 11E:
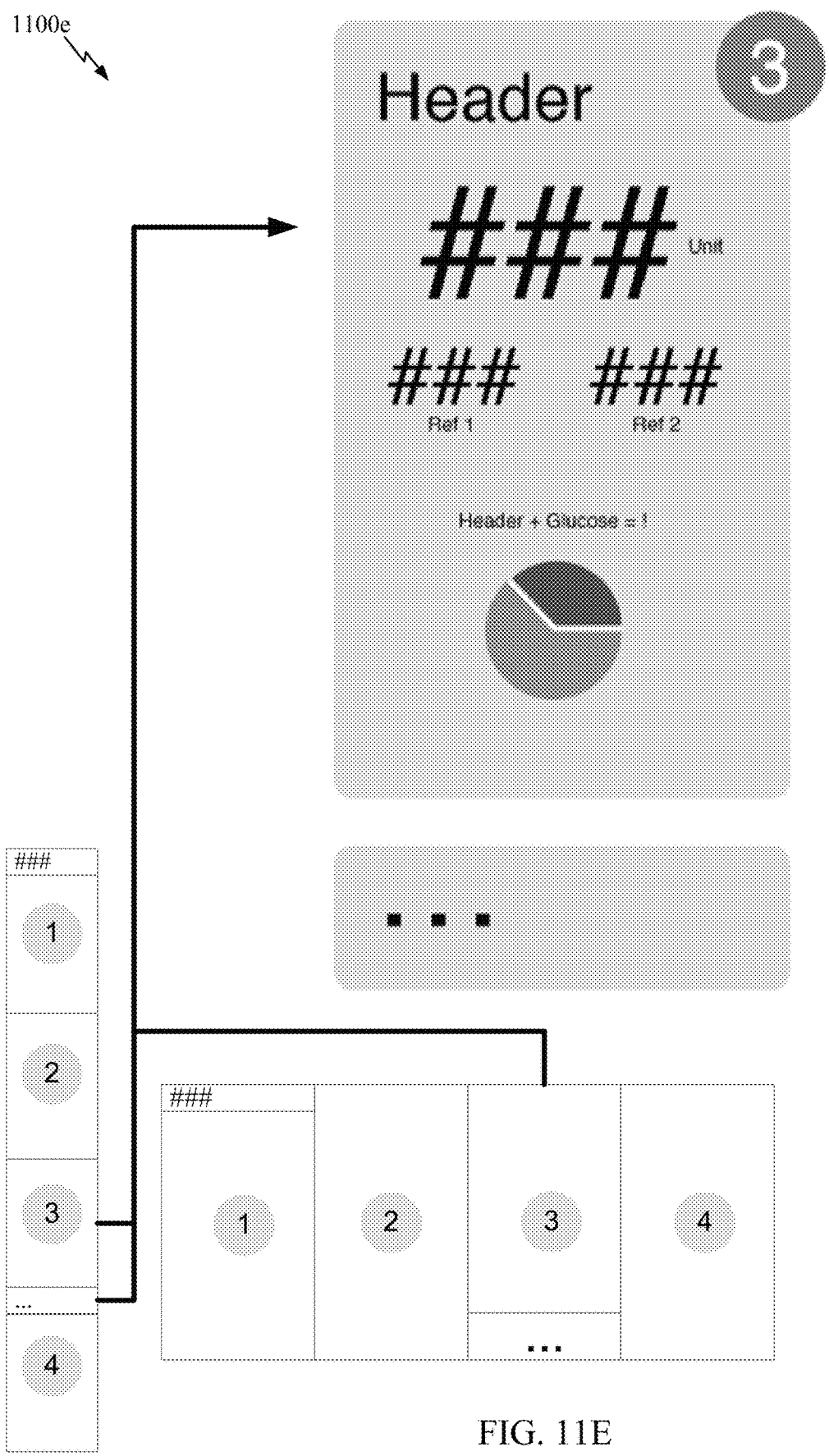
Figure 12E:
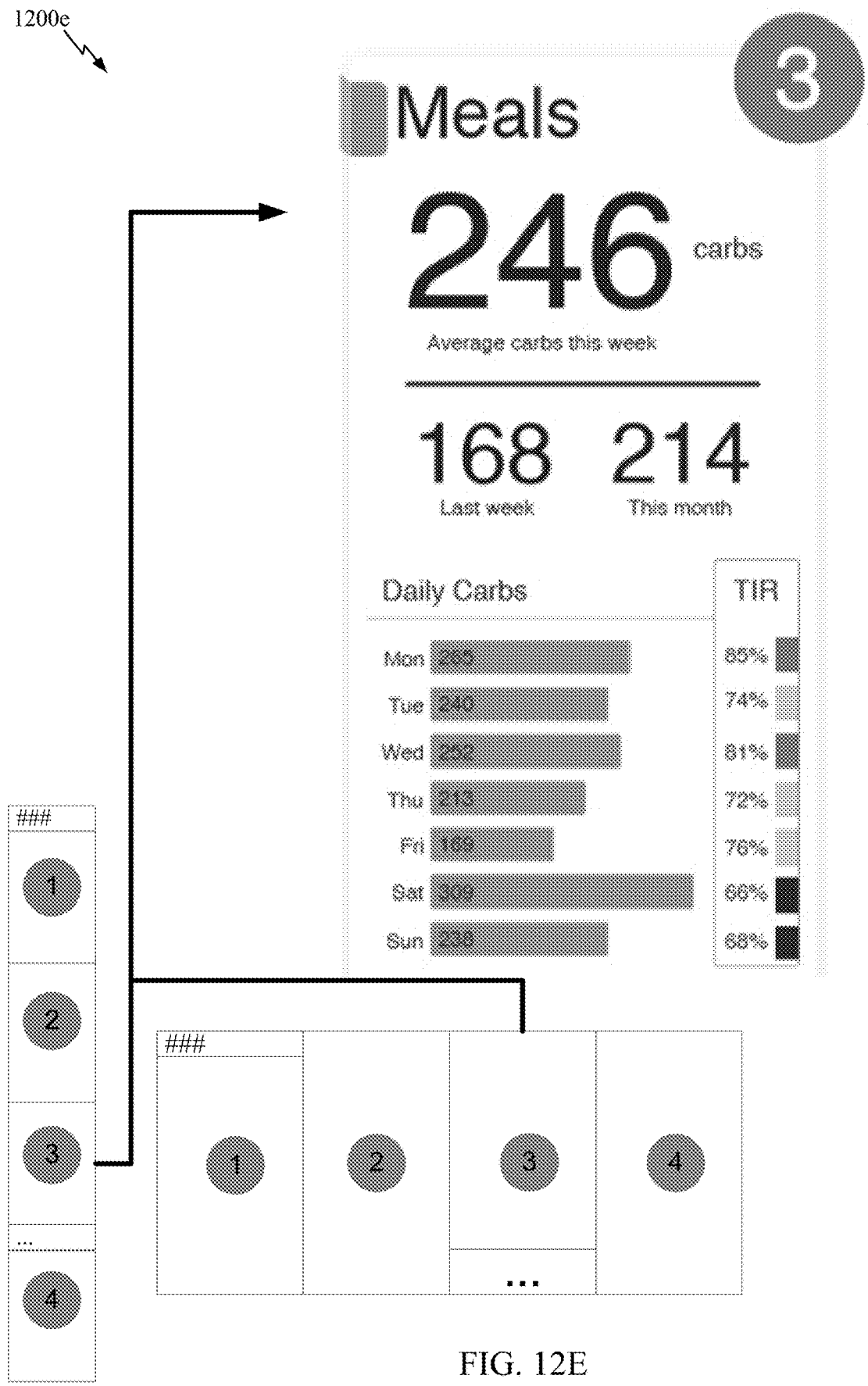

As shown in FIGS. 11E and 12E, in a third feature 1100e, 1200e of wireframes 1100a, 1100b and user interface views 1200a, 1200b, information related to the user's carb intake over a specified time may be provided. The carb intake information (i.e., calculated based on a user's input of events, including meals logged by the user) may include an average number of carbs (i.e., determined by logic 420C of FIG. 4) for the current week in comparison to a previous week's average number of carbs and the month's average number of carbs, a day-by-day bar graph of the user's average carb intake, and a day-by-day breakdown of the user's percentage of time in a target glucose range. Percentage of time in the target glucose range may be provided in the third feature to assist the user in identifying a correlation, if any, between carb intake and its effect on the user's glucose level.

Figure 12F:
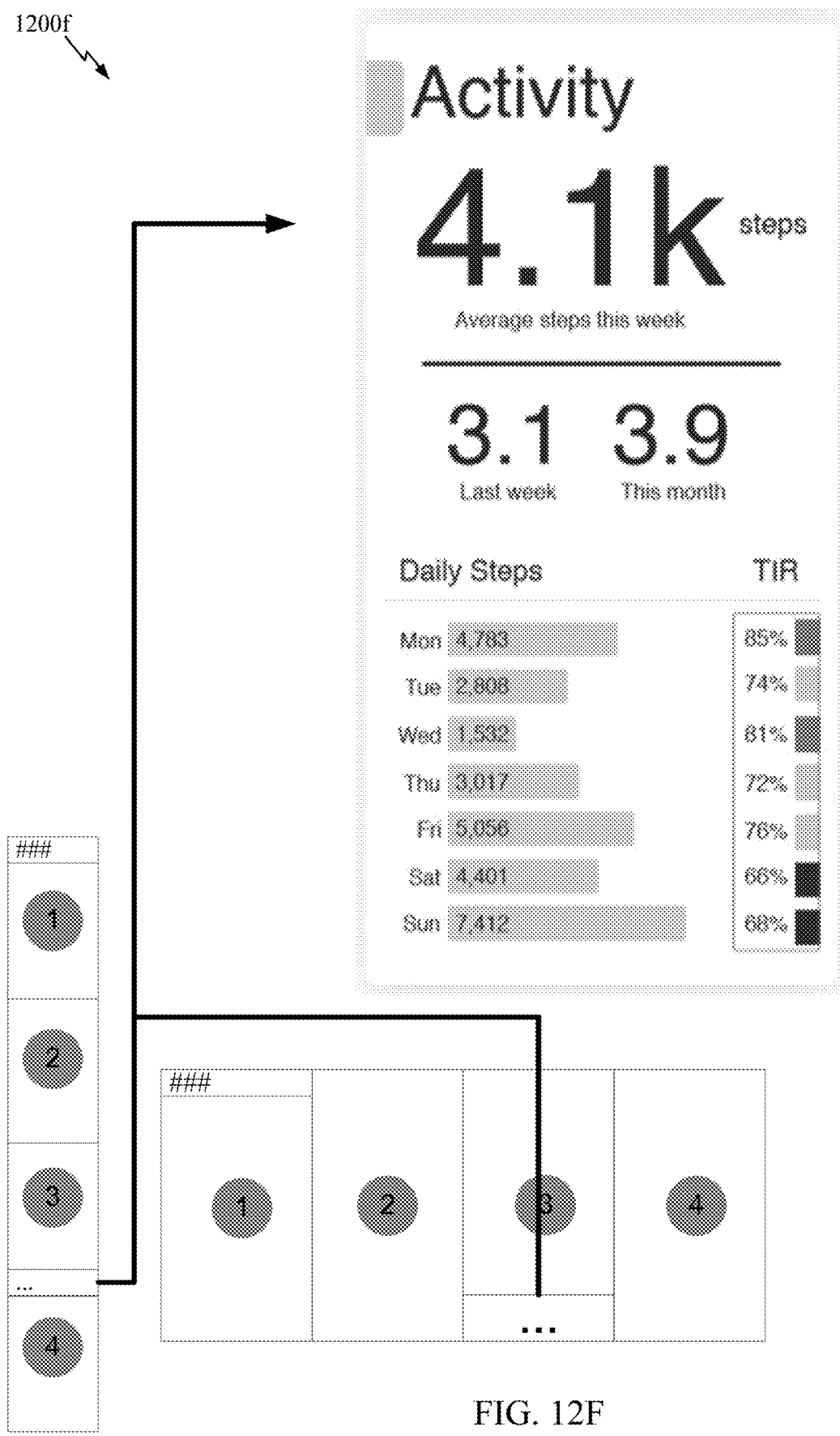

In some examples, the third feature of wireframes 1100a, 1100b and user interface views 1200a, 1200b may also include information related to the user's activity over a specified time (e.g., additional third feature 1200f shown in FIG. 12F). The activity information (i.e., calculated based on a user's input or tracker of events, including steps taken by the user) may include an average number of steps (i.e., determined by logic 420C of FIG. 4) for the current week in comparison to a previous week's average number of steps and the month's average number of steps, a day-by-day bar graph of the host's average steps taken, and a day-by-day breakdown of the host's percentage of time in a target glucose range. Percentage of time in the target glucose range may be provided in the third aspect to assist the user in identifying correlation, if any, between steps taken and its effect on the user's glucose level.

Figure 11F:
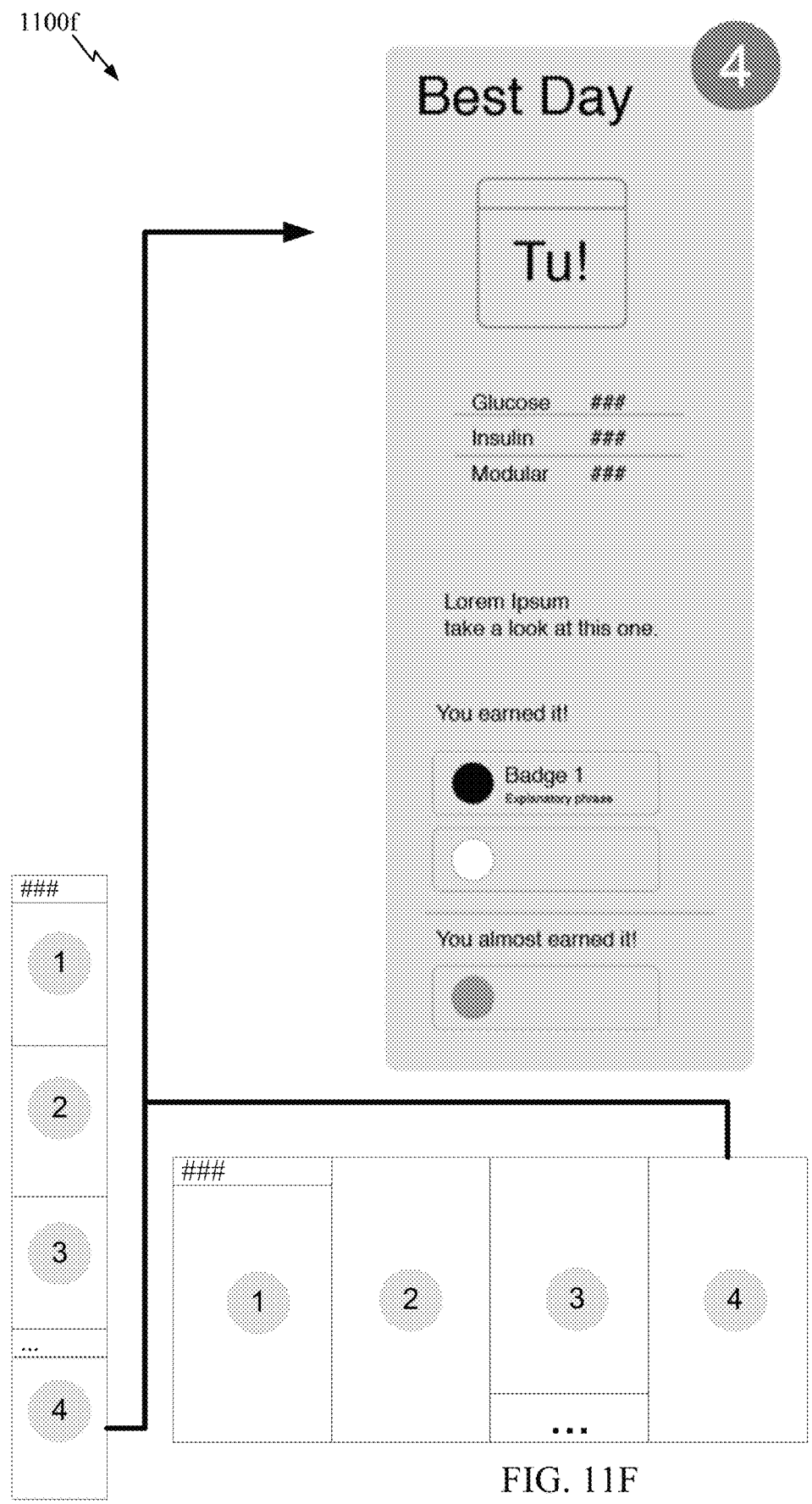
Figure 12G:
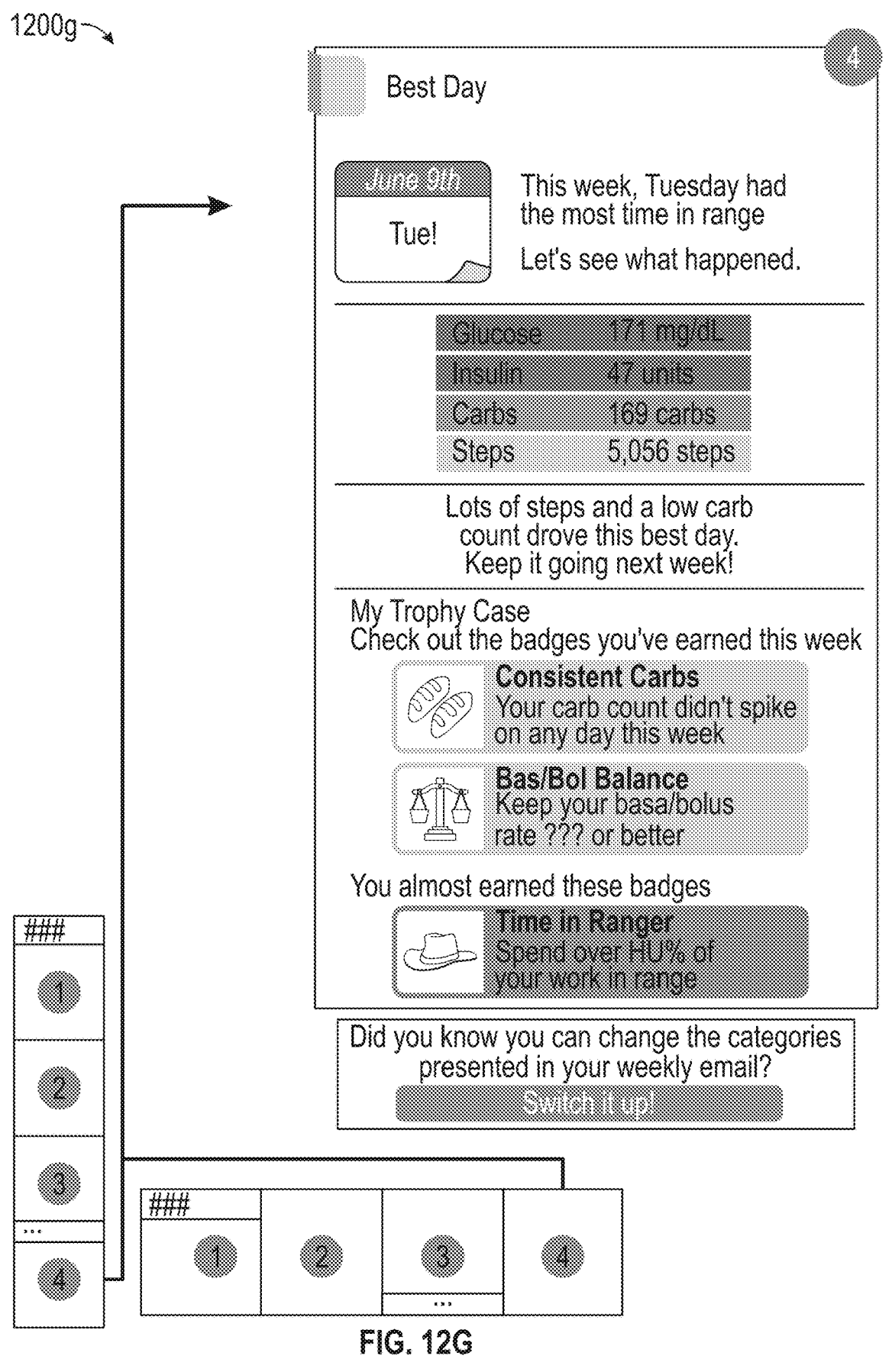

As shown in FIGS. 11F and 12G, in a fourth feature 1100f, 1200g of wireframes 1100a, 1100b and user interface views 1200a, 1200b, information related to the user's "best day" over a specified time may be provided. Logic 420C may determine a user's "best day" based on the day the user spent the most time in a target glucose range. In some examples, the user's glucose, insulin, carbs, and steps may be given to better understand the factors that contributed to and resulted in the user's "best day". A summary of contributing factors may also be given to motivate the user to experience more days similar to the user's "best day". A user may also receive trophies (also referred to herein as badges) to reward the user for their "best day" behavior. In some examples, the trophy may include a "Consistent Carbs Trophy" used to reward the user for having a day without any carb spikes. In some examples, the trophy may include a "Bas/Bol Balancer Trophy" used to reward the user for keeping their basal/bolus ratio at a target ratio (e.g., 60/40), or better. In some examples, the trophy may include a "Time in Ranger Trophy" used to reward the user for spending over 80% of their week in a target glucose range. In some examples, a trophy the user almost earned may be identified.

In some examples, features one through four of wireframes 1100a, 1100b and user interface views 1200a, 1200b may be presented chronologically; from top to bottom, as shown in the vertical layouts of FIGS. 11A and 12A, or from left to right as shown in the horizontal layouts in FIGS. 11B and 12B. In some example, features one through four may be presented in any random order.

Figure 13C:
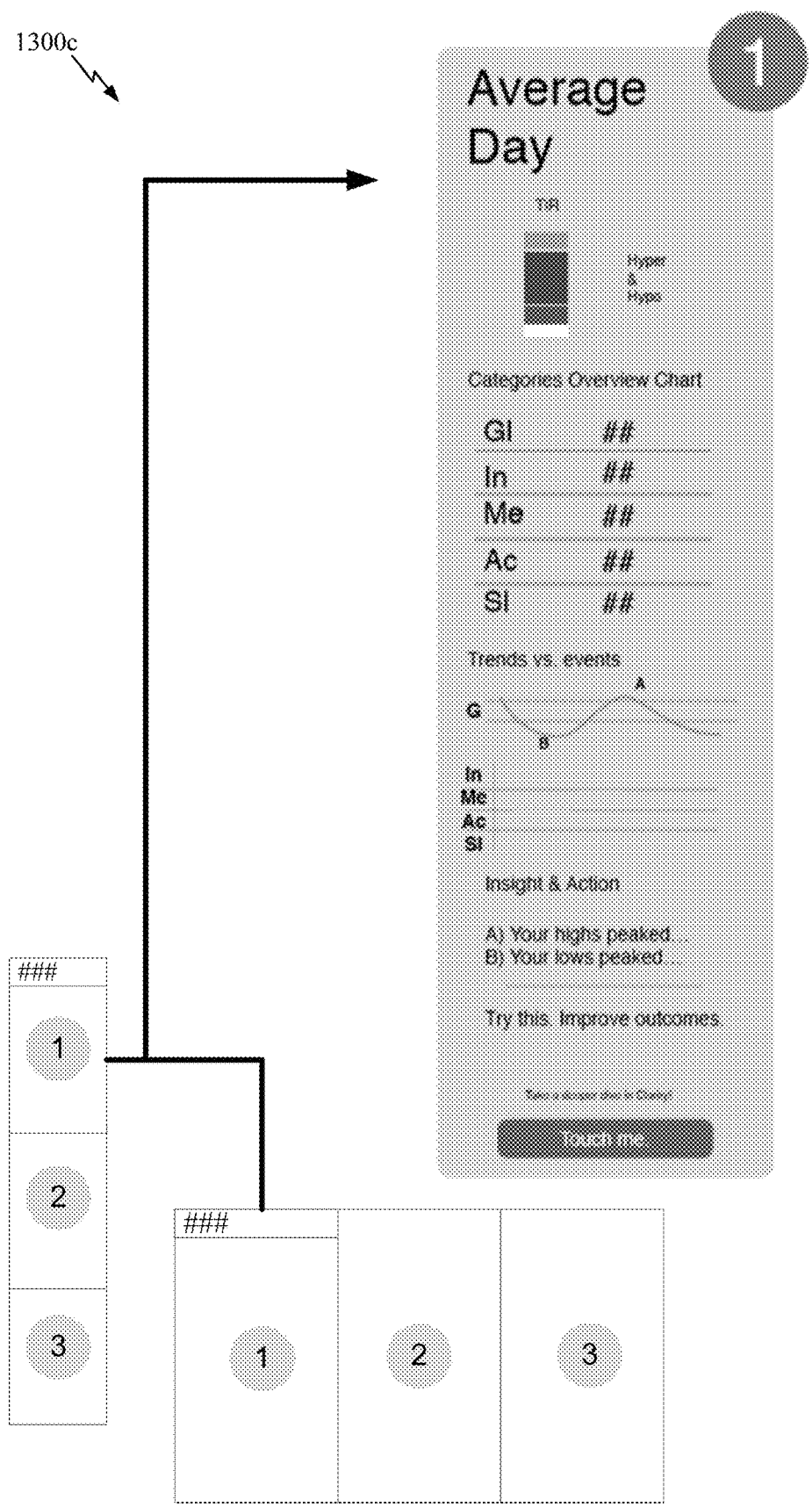
FIGS. 13C-13E illustrate enlarged views of features one through three shown in the vertical and horizontal wireframes of FIG. 13A and FIG. 13B, respectively, in accordance with some example aspects of the present disclosure.
Figure 13D:
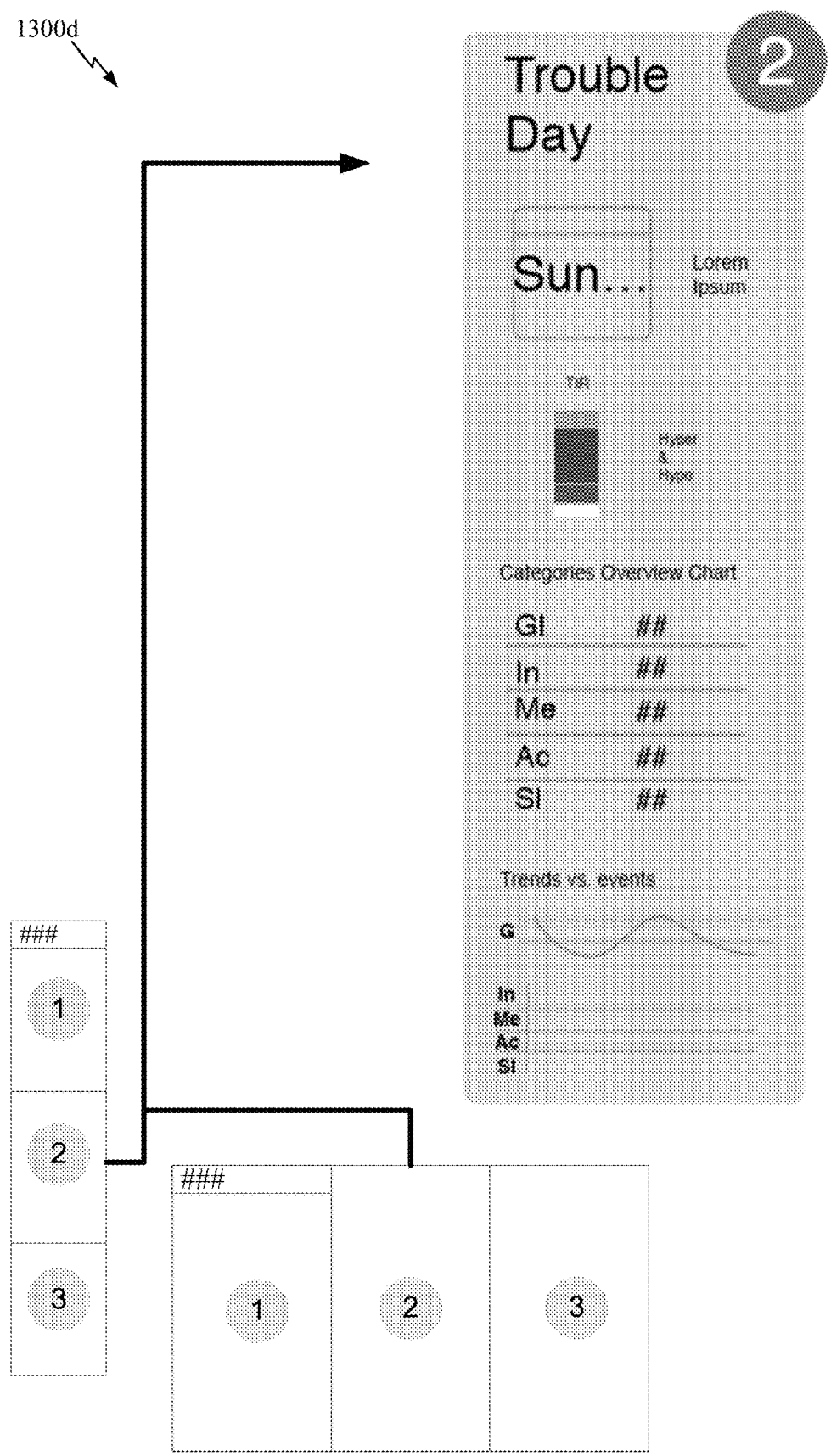
Figure 13E:
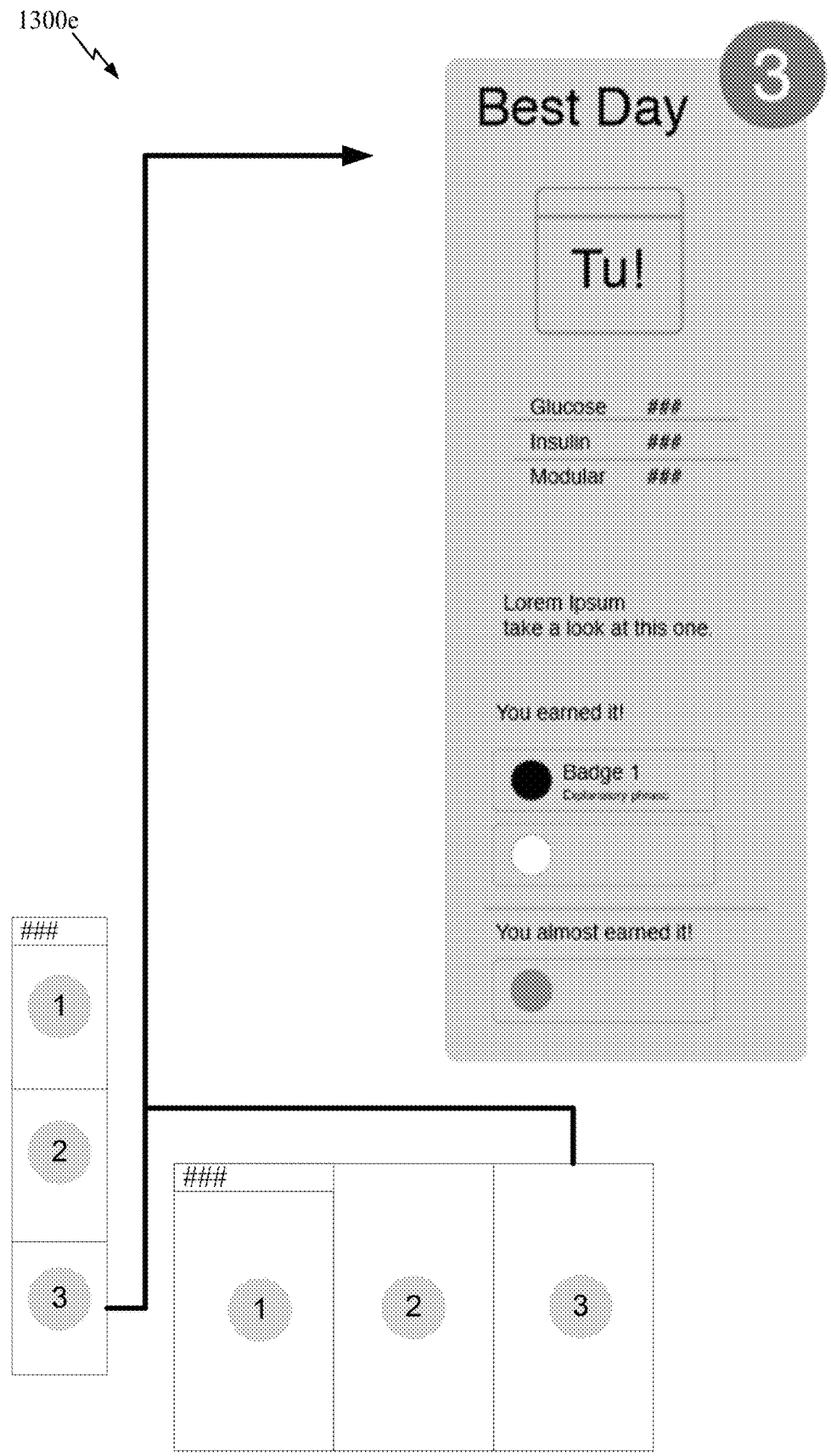

FIG. 13A illustrates an example wireframe 1300a of another example user interface view in a vertical horizontal layout, and FIG. 13B illustrates an example wireframe 1300b of the user interface view in a horizontal layout, in accordance with some example aspects of the present disclosure. FIGS. 13C-13E illustrate enlarged views of features one through three shown in the vertical and horizontal wireframes, 1300a and 1300b, respectively, and are described in more detail further below.

Figure 14A:
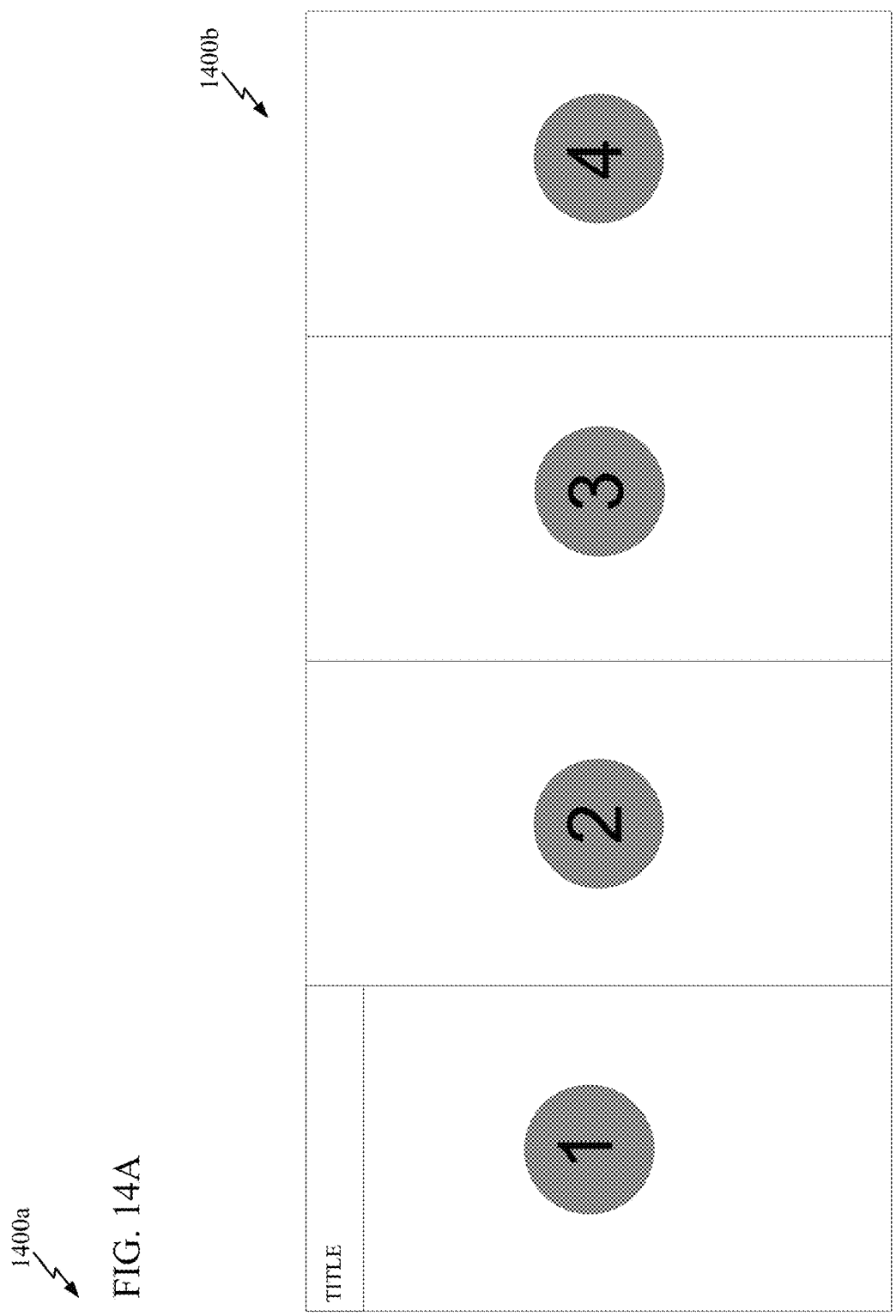
FIG. 14A illustrates an example user interface view associated with sensor data representative of glucose concentration level(s) in a host in a vertical layout which corresponds to the wireframe of FIG. 13A, in accordance with some example aspects of the present disclosure.
Figure 14B:
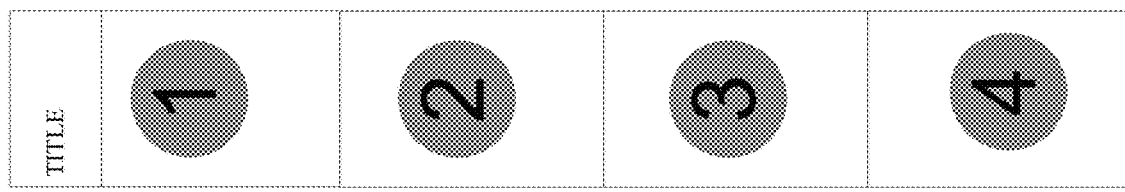
FIG. 14B illustrates an example user interface view associated with sensor data representative of glucose concentration level(s) in a host in a horizontal layout which corresponds to the wireframe of FIG. 13B, in accordance with some example aspects of the present disclosure.

FIG. 14A illustrates an example user interface view 1400a associated with sensor data representative of glucose concentration level(s) in a user in a vertical layout which corresponds to the wireframe 1300a, and FIG. 14B illustrates an example user interface view 1400b in a horizontal layout which corresponds to the wireframe 1300b, in accordance with some example aspects of the present disclosure. FIGS. 14C-14F illustrate enlarged views of features one through four shown in the vertical and horizontal user interface views, 1400a and 1400b, respectively, and are described in more detail further below.

Wireframe and user interface view, 1300a and 1400a, show vertical orientations of a wireframe and a user interface view, respectively, while wireframe and user interface view, 1300b and 1400b, show horizontal orientations of a wireframe and user interface view, respectively. Although both horizontal and vertical orientations are shown, only one orientation may be displayed to the user. In some aspects, the orientation of the user interface view may be automatically selected and displayed based on a type of a user device.

As shown in the example user interface views of FIGS. 14A and 14B, and corresponding wireframes of FIGS. 13A and 13B, a weekly report may be day-type based, which refers to a report that compares an "average day" to a "trouble day" and to a "best day". A user's "best day" may be determined (e.g., determined by logic 420C) based on the day the user spent the most time in a target glucose range. Alternatively, a user's "trouble day" may be determined based on the day the user spent the least amount of time in a target glucose range.

Figure 14C:
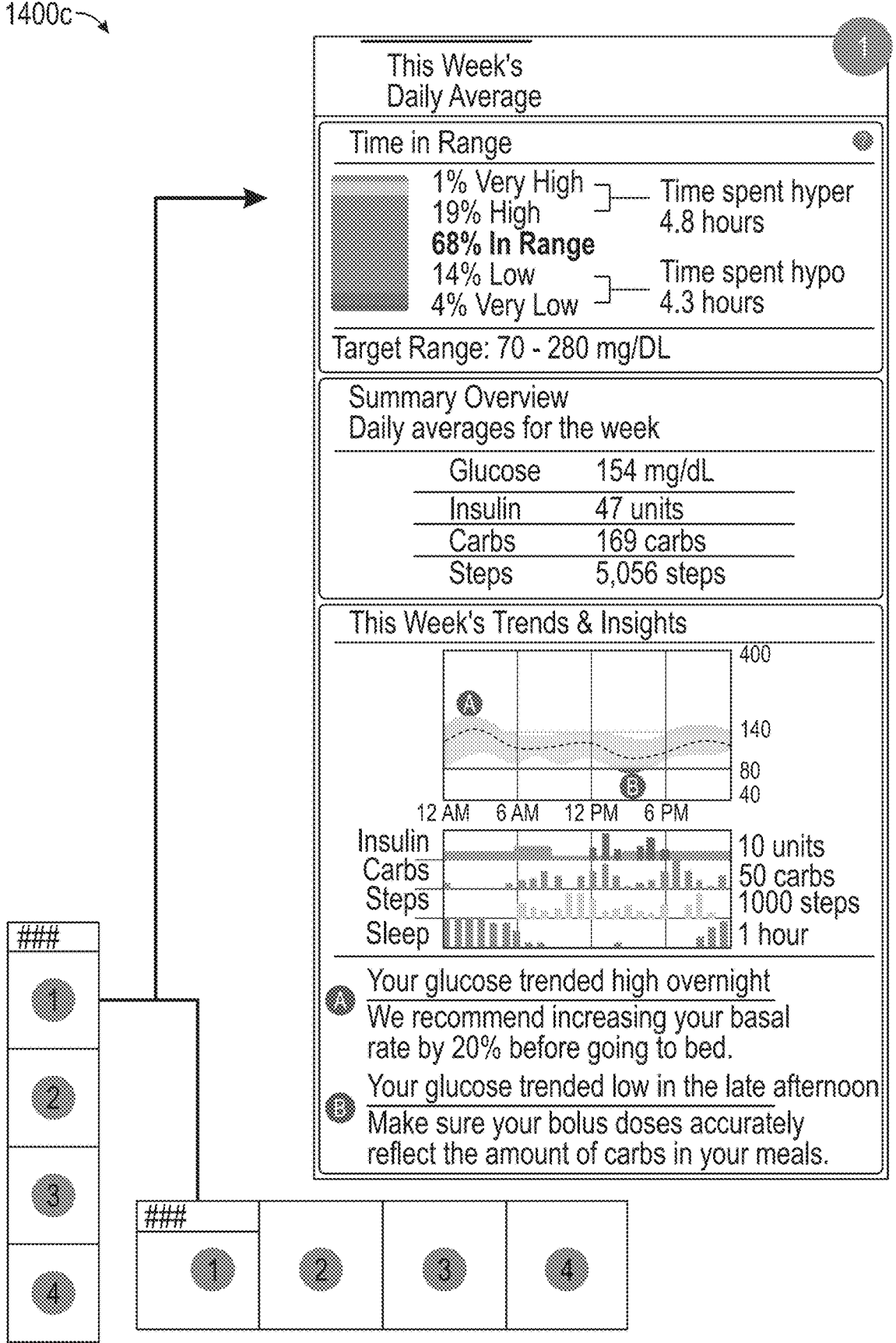
FIGS. 14C-14F illustrate enlarged views of features one through four shown in the vertical and horizontal user interface views of FIG. 14A and FIG. 14B, respectively, in accordance with some example aspects of the present disclosure.

As shown in FIGS. 13C and 14C, in a first feature 1300c, 1400c of wireframes 1300a, 1300b and user interface views 1400a, 1400b, a time in range stacked bar graph may be provided that represents a percentage of time the user was in a target glucose range, a very high or high glucose range, and a very low or low glucose range over a specified period (e.g., any continuous seven day period). In some examples, the target glucose range may be defined as a different range for daytime (e.g., 6:00 AM-10:00 PM) and nighttime (e.g., 10:00 PM-6:00 AM) hours. The user's percentage of time in range may also be compared to the previous week's percentage of time in range. In some examples, the stacked bar graph may be presented using different colors to differentiate the percentages of time the host was in a target glucose range, a very high or high glucose range, and a very low or low glucose range over a specified period. In some examples, the stacked bar graph may be presented using different size blocks (stacked in the stacked bar graph) for each of the ranges. The varying sizes may correlate to the amount of time the user spent in each range. For example, the largest block size in the stacked bar graph may represent the glucose range the user spent the most amount of time in over a specified period of time, while the smallest block size in the stacked bar graph may represent the glucose range the user spent the least amount of time in over a specified period of time.

Additionally, the first feature of the user interface view may provide a summary overview of the user's average glucose, average insulin units, average carb intake, and average steps logged for a specified period (e.g., any continuous seven day period). The first feature may also provide a trend and insight graph. The trend graph may include a compilation of a user's time in range presented in a scatter plot with a line of best fit. The line of best fit expresses the relationship between the data points and identifies a user's time in range trend over a twelve hour period (e.g., 12:00 AM-12:00 AM in the example shown) for a specified period (e.g., any continuous seven day period). Additionally, target glucose ranges, for both daytime and nighttime hours, may be provided in the graph. The target glucose ranges may be defined as a different ranges for daytime and nighttime hours. For example, the graph may identify a daytime target glucose range using a figure in the shape of a sun on the side of the trend graph and may identify a nighttime target glucose range using a figure in the shape of a moon on the side of the trend graph (sun and moon figures not shown). The trend graph may also provide different color bar graphs to make the distinction between a user's time in a high or very high glucose range, a user's time in a low or very low glucose range, and a user's time in glucose range over a twelve hour period for a specified period. The trend graph may also be a bar graph broken down into categories of average insulin units, average carb intake, and average steps logged over a particular period of time (e.g., twelve hours) for a specified period (e.g., any continuous seven day period). Insights may include summaries of high and low periods and recommendations for mitigating these unwanted spikes.

Figure 14D:
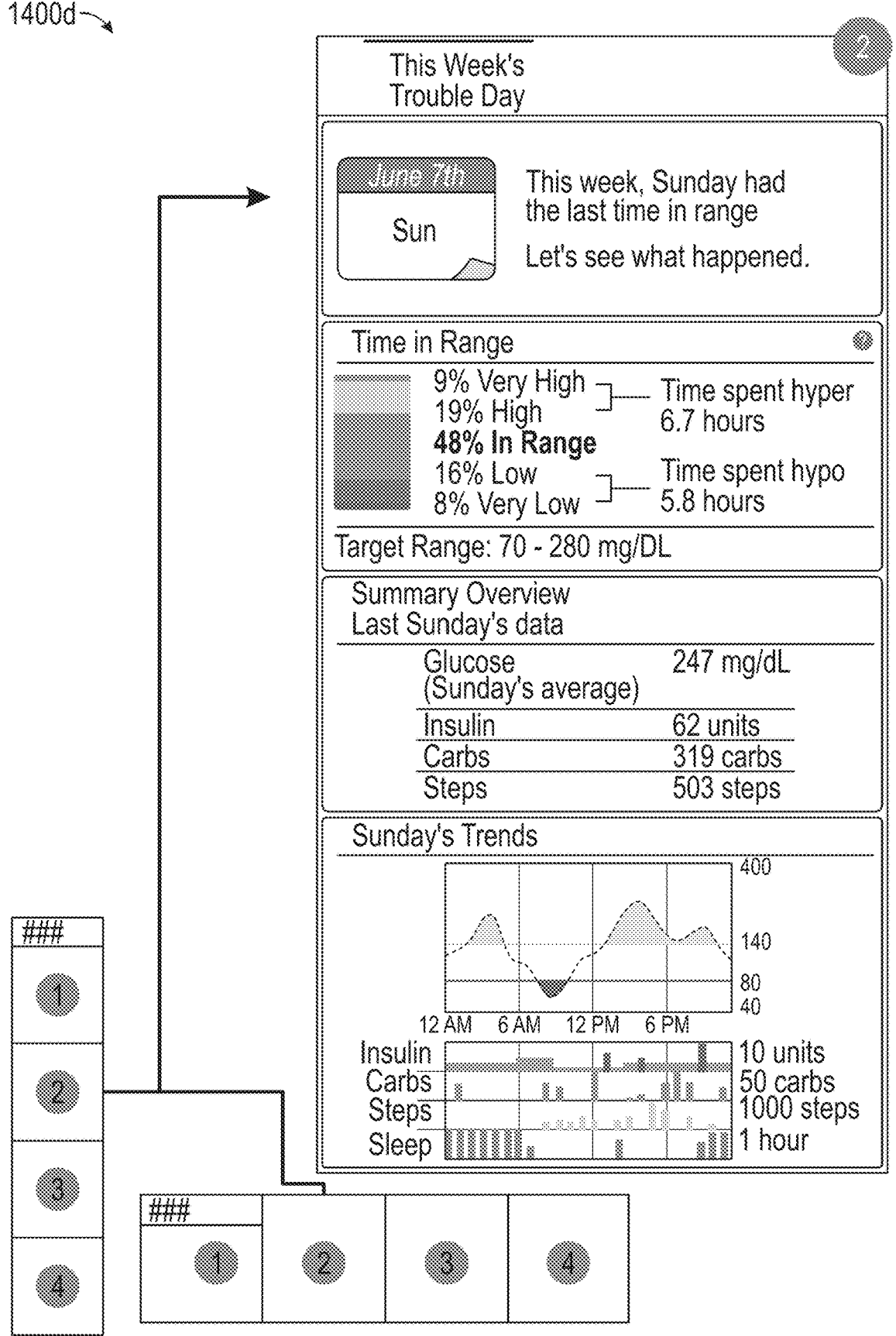

As shown in FIGS. 13D and 14D, in a second feature 1300d, 1400d of wireframes 1300a, 1300b and user interface views 1300a, 1300b, information related to the user's "trouble day" over a specified time may be provided. In some examples, the user's glucose, insulin, carbs, and steps may be given to better understand the contributing factors that resulted in the user's "trouble day". Additionally, trend graphs for the user's "trouble day" may be provided. The trend graph may present a compilation of a user's glucose levels, insulin units, carb intake, steps logged, and hours of sleep over a particular period of time (e.g., 24-hour period, such as 12:00 AM to 12:00 AM). The trend graph may identify relationships the user may not have otherwise know. For example, as shown in the example Sunday trend graph, between about 6 AM and about 9 AM the user experienced a first drop in their glucose level, and between about 3 PM to about 6 PM the user experienced a second drop in their glucose level. During each of these time periods, the user logged multiple carbs. Although not the only factor contributing to the user's glucose levels, there may exist an inverse relationship between glucose level and carb intake presented in the trend graph, which the user may not have known previously. Accordingly, the user may take appropriate action to prevent future glucose daytime lows.

Figure 14E:
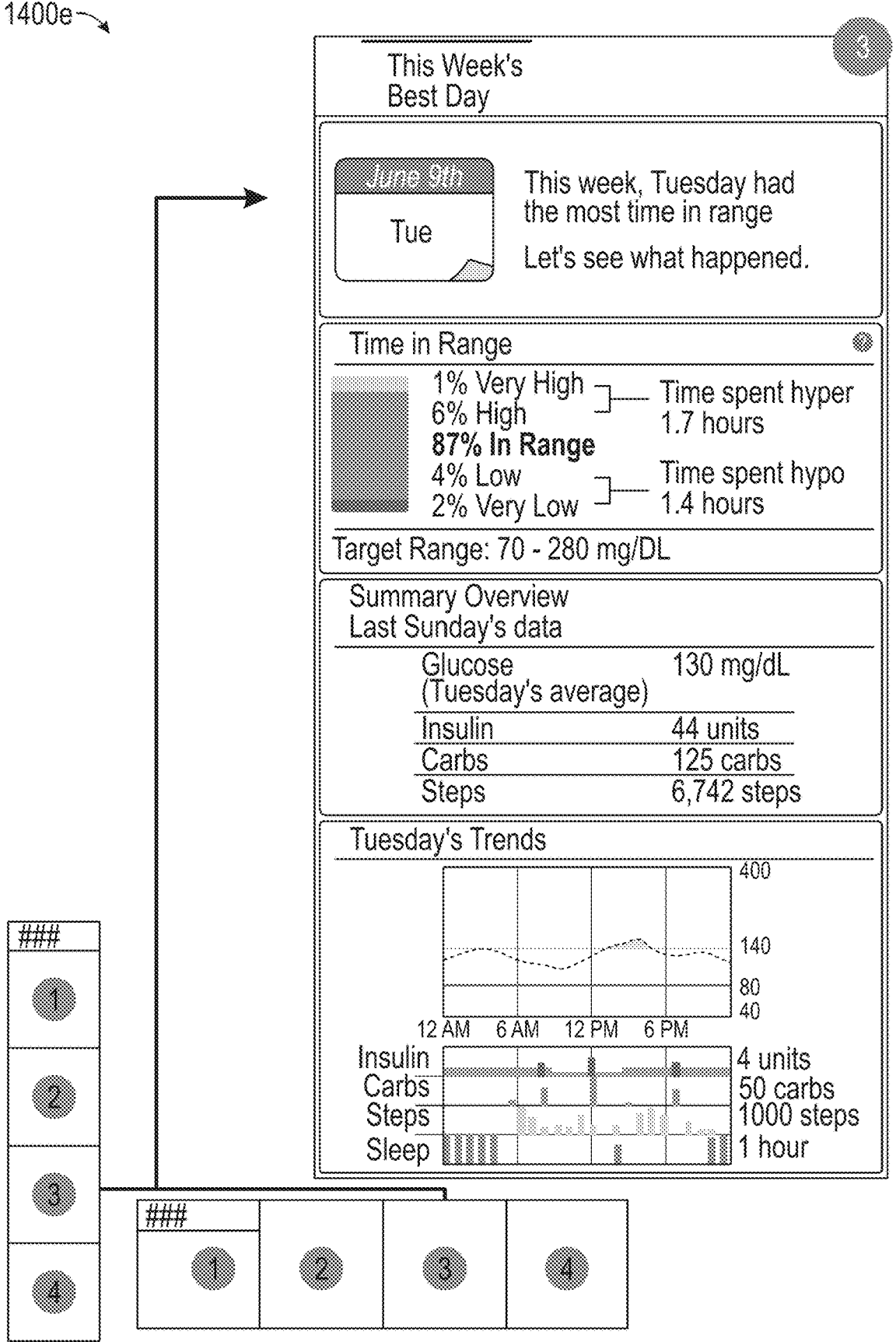

As shown in FIGS. 13E and 14E, in a third feature 1300e, 1400e of wireframes 1300a, 1300b and corresponding user interface views 1400a, 1400b similar information as the first feature may be provided; however, the data may be tailored to represent the user's "best day".

Figure 14F:
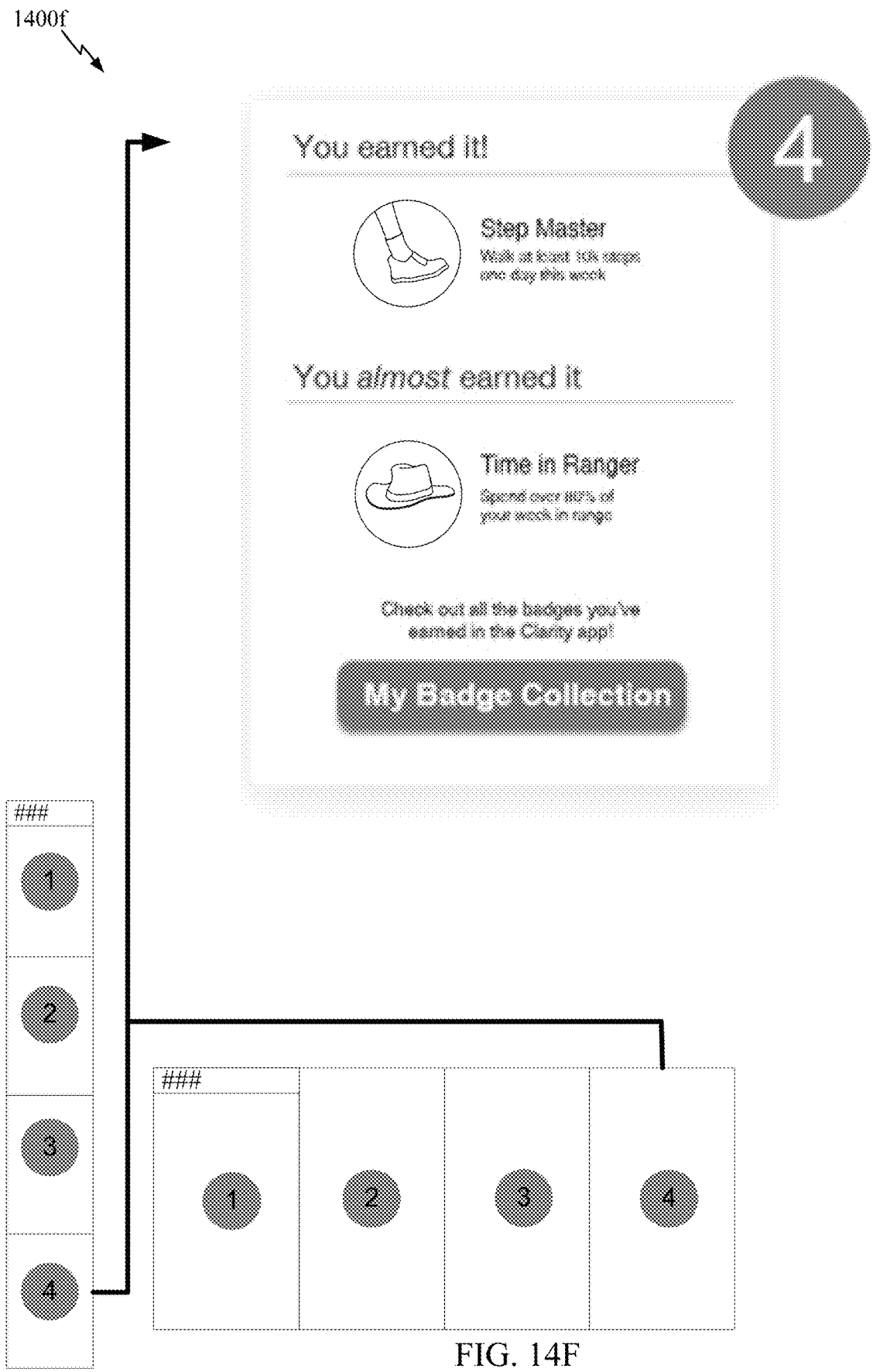

As shown in FIG. 14F, in a fourth feature 1400f of user interface views 1300a, 1300b, a user may receive trophies (also referred to herein as badges) to reward the user for their weekly behavior. In some examples, the trophy may include a "Step Master Trophy" used to reward the user for having a day during the week where the user walked at least 10,000 steps. In some examples, the trophy may include a "Time in Range Trophy" used to reward the user for spending over 80% of their week in a target glucose range. In some examples, a trophy the user almost earned may be identified. A button (e.g., "My Badge Collection" button) may also be provided for a user to launch a view of all trophies (also referred to herein as badges) earned.

In some examples, features one through three of wireframes 1300a, 1300b and features one through four of user interface views 1400a, 1400b may be presented chronologically; from top to bottom, as shown in the vertical layouts of FIGS. 13A and 14A, or from left to right, as shown in the horizontal layouts in FIGS. 13B and 14B.

While the foregoing is directed to visualization of a user's analyte data (and in some cases, non-analyte data, such as carb intake or steps taken) in specific formats for presentation, other formats may be customized and/or designed to best meet the needs of each individual user.

Example Analyte Data Processing and Visualization of Analyte Data on Widgets

Aspects of the present disclosure provide techniques for providing one or more user interface views for display on one or more widgets. More specifically, aspects of the present disclosure provide techniques for visualization of analyte data (and/or non-analyte data) on widgets. In some aspects, with continuous glucose monitoring, information associated with a user's blood glucose data can be processed, presented to the user, and updated in real-time or periodically via widgets. While the analyte for measurement and visualization on widgets by the devices and methods described herein is glucose, other biological parameters and/or analytes may be considered, as well.

A hallmark of modern graphical user interfaces is that they allow a large number of items to be displayed on a screen at the same time. Widgets are a user's portal to a variety of information and quick functionality. Widgets may communicate with a remote server to provide information to the user (e.g., a weather report), or widgets may provide commonly needed functionality (for example, a calculator), or widgets may act as an information repository (e.g., a notepad or calendar). Some widgets may provide a combination of these functionalities. Some widgets may interact with remote sources of information, such as servers, to provide information. For example, a weather feature may retrieve live weather data from a remote server. Widgets may be interactive, so that a user may perform common input operations (such as clicking a mouse or typing on a keyboard) to utilize the functionality of a widget. Additionally, widgets may act as a link to a program, such as, an application (app) running on a user's device. For example, by engaging with a widget (e.g., clicking on a widget), a user may be re-directed to an app thereby allowing the user to enjoy all features, services, and/or information provided by the app.

Widgets may be "pinned" to a user interface in various spots and sizes, allowing for many different layouts. Widgets may be located in a view that is accessible with a swipe (e.g., from left to right) on a user device's home screen or may be accessible on the user device's home screen (without a need to swipe). In some example aspects, widgets may not overlap one another; if the user attempts to move one widget to the position occupied by another widget, one of the widgets may automatically move out of the way to make room. In some example aspects, the position, configuration, and size of widgets may be saved when the user interface is dismissed, so that the same state may be restored the next time the dashboard is invoked.

Figure 15:
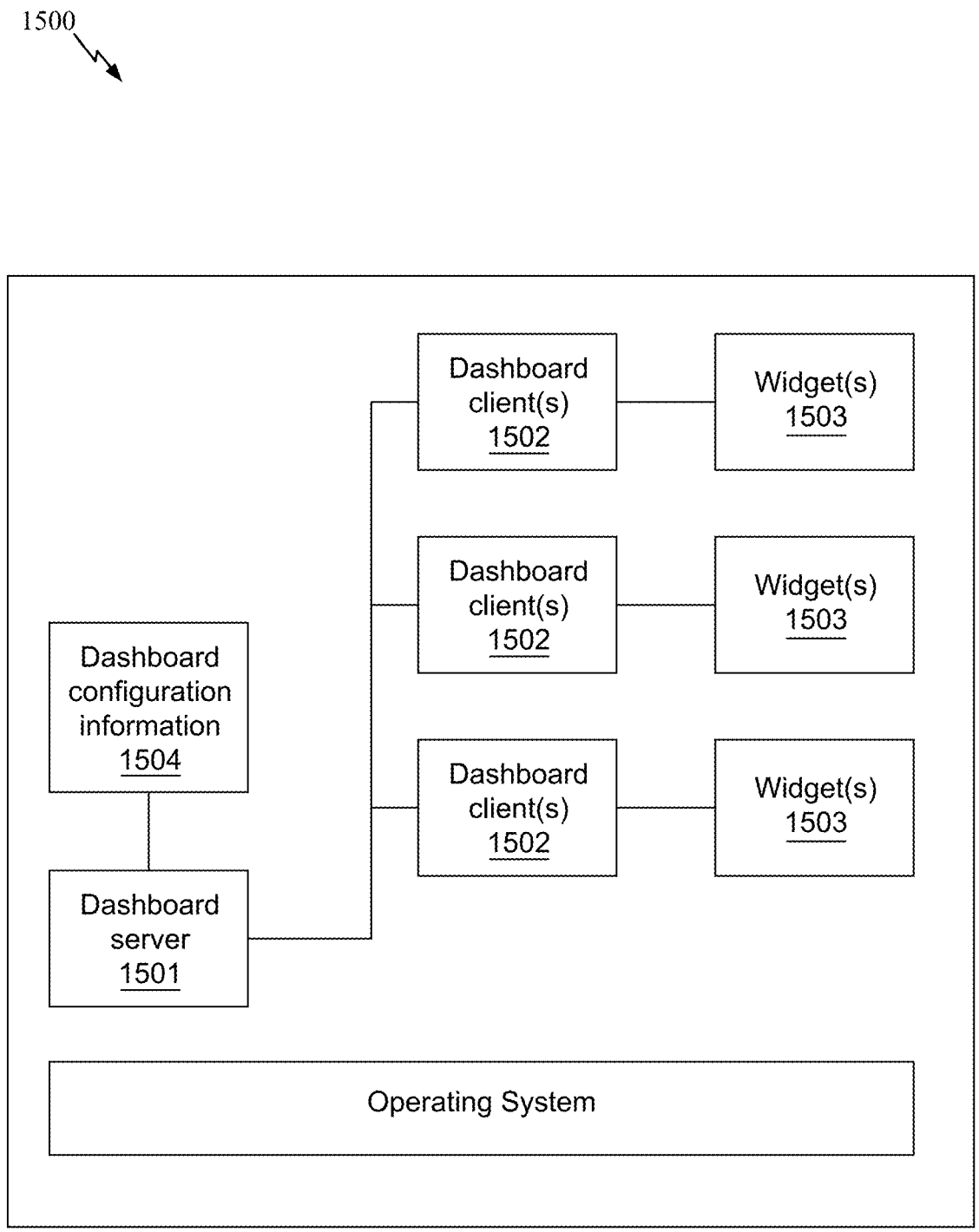
FIG. 15 is a block diagram conceptually illustrating a software architecture for implementing widget functionality, in accordance with some example aspects of the present disclosure.

FIG. 15 is a block diagram conceptually illustrating a software architecture 1500 for implementing widget functionality, in accordance with some example aspects of the present disclosure. As shown in FIG. 15, software architecture 1500 may include an operating system running a dashboard server 1501, dashboard client(s) 1502, and widget(s) 1503. Dashboard configuration information 1504 may be used by server 1501 and/or clients 1502 to specify the configuration options (e.g., access levels, etc.) for displaying widgets 1503. Clients 1502 may display widgets 1503 by rendering web pages into a view, the size of each view may be defined as metadata associated with the corresponding widget 1503. Server 1501 may provide data for rendering a user interface layer that may be overlaid on the desktop, or home screen, of the user interface. Widgets 1503 may be rendered into the separate layer, and then that separate user interface layer may be drawn on top of the normal desktop or home screen, so as to partially or completely obscure the desktop or home screen while the dashboard is active. In some aspects, widgets associated with a user's analyte data may be provided.

According to certain aspects, a widget may be provided by a user device (e.g., by an application running on the user device). In this, information displayed on the widget may be provided by a user device (e.g., rather than provided by a server). For example, some widgets may operate without a network connection. In some cases, information may be provided by another user device having a connection with the user device, such as a wearable.

Figure 16:
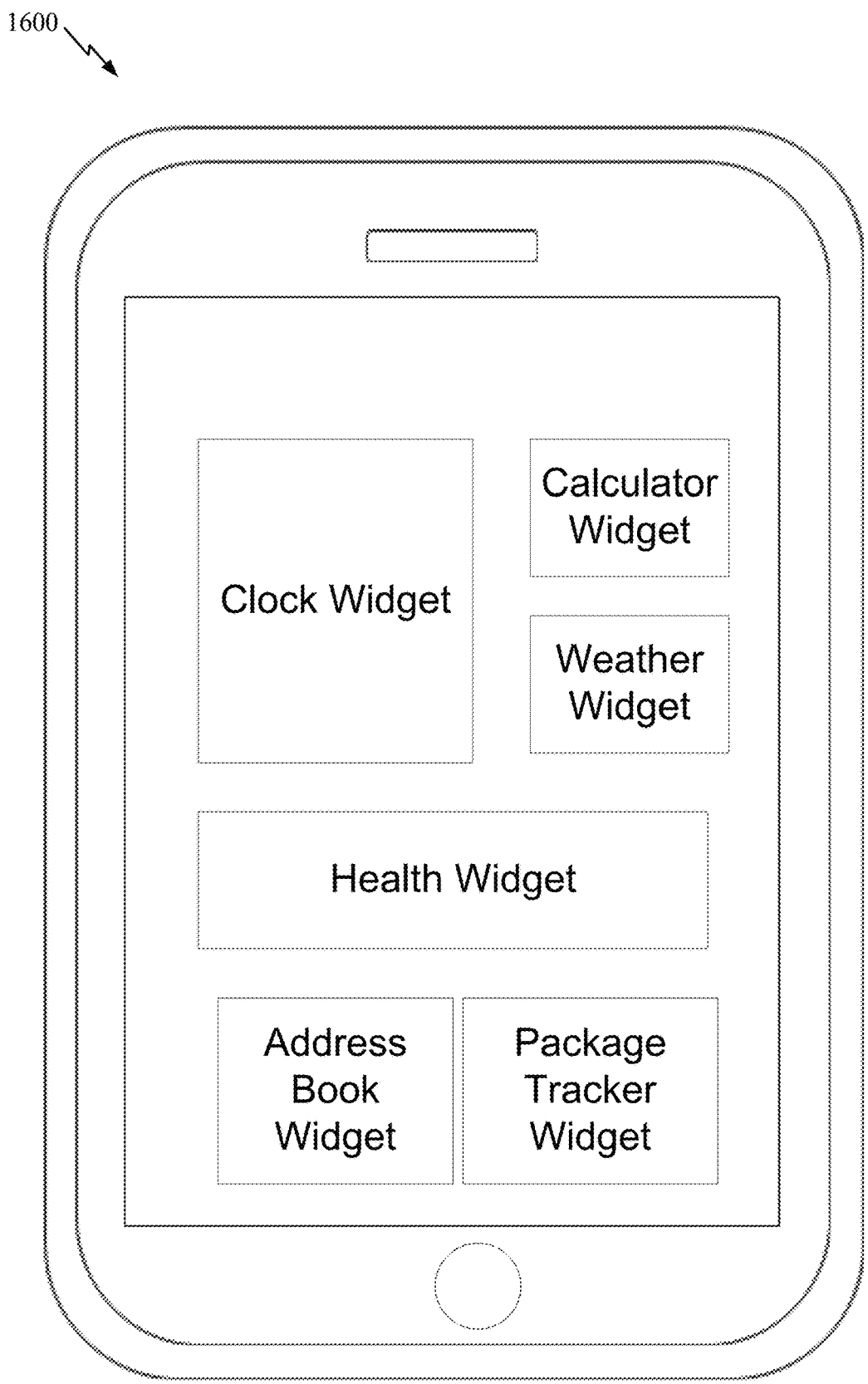
FIG. 16 illustrates an example dashboard including a number of user interface elements, also referred to herein as "widgets", in accordance with some example aspects of the present disclosure.

FIG. 16 illustrates an example dashboard 1600 (also referred to as "unified interest layers") including a number of user interface elements, also referred to herein as "widgets", in accordance with some example aspects of the present disclosure. These user interface elements, or widgets, generally include software accessories for performing useful, commonly needed functions. Examples of widgets may include, without limitation, a calendar, a calculator, an address book, a package tracker, a weather feature, a health tracker, and the like.

Users may interact with and/or configure widgets as desired. For example, users may move widgets around the screen and/or resize widgets, if applicable. Some widgets may be resizable, and some may be of a fixed size; the widget author may specify whether a widget may be resized. Some widgets may automatically resize themselves based on the amount or nature of the data being displayed.

Figure 17:
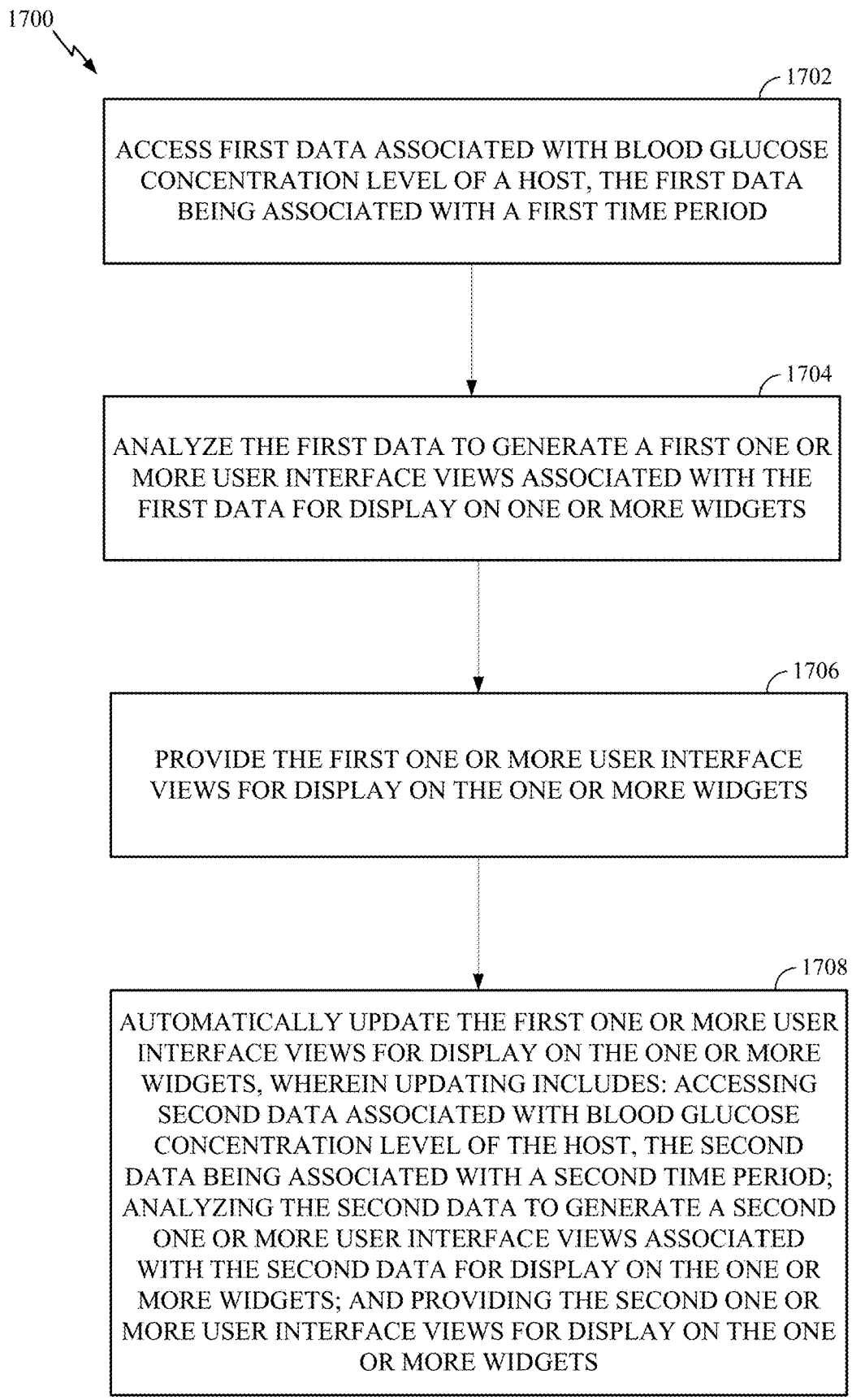
FIG. 17 is a flow diagram illustrating example operations for generating a user interface view associated with sensor data representative of glucose concentration level(s) in a host, in accordance with some example aspects of the present disclosure.

FIG. 17 is a flow diagram illustrating example operations 1700 for generating a user interface view associated with sensor data representative of a glucose concentration level in a user, in accordance with some example aspects of the present disclosure.

Operations 1700 begin, at 1702, by accessing first data associated with blood glucose concentration level(s) of a user during a first time period. For example, analyte processor 490 in FIG. 4 may access data stored in repository 475 and/or receive data from one or more sources.

At 1704, operations 1700 include analyzing the first data to generate a first one or more user interface views associated with the first data for display on one or more widgets. For example, one or more components of analyte processor 490 in FIG. 4 may process analyte data and/or other information associated with a user to generate information to be provided to the user in one or more widgets.

At 1706, operations 1700 include providing the first one or more user interface views for display on the one or more widgets. For example, analyte processor 490 may provide the one or more widgets for display at the UIs 410, the computer 20, and/or other user interfaces.

At 1708, operations 1700 include automatically updating the first one or more user interface views for display on the one or more widgets. For example, the automatically updating includes accessing second data associated with blood glucose concentration levels of the user during a second time period, analyzing the second data to generate a second one or more user interface views associated with the second data for display on the one or more widgets, and providing the second one or more user interface views for display on the one or more widgets.

FIGS. 18A-18C provide a table 1800A-1800C categorizing example analyte data widgets, in accordance with some example aspects of the present disclosure. As shown in FIGS. 18A-18C, widgets may be categorized as either a summary type widget, a motivation type widget, an event type widget, or another type widget, in accordance with some example aspects of the present disclosure.

A summary widget may be a widget that provides a short, clear description of the main facts and/or ideas about the user's collected data over a specified period of time (e.g., eight hours, three days, seven days, fourteen days, thirty days, or another defined time period). For example, a summary widget may provide a user's average glucose from measured sensor data over a period of seven days. A motivation type widget may be a widget that provides a comparison of data and/or a message used to incentivize a user to take action (e.g., maintain glucose stability, make a lifestyle change, etc.). For example, a motivation type widget may provide the user with an indication of their "best day" for the past seven days with a summary of factors which contributed to their "best day". Such a widget may be used to motivate the user to achieve similar results for other days (e.g., incentivize the user to keep their average glucose for the next few days at the same average glucose level as their "best day"). An event type widget may be a widget which tracks a user's health based on events the user has logged. For example, a logged event may include a logged meal consumed (e.g., input of calories, carbs, etc.) or a logged period of time when the user engaged in some form of exercise (e.g., input of exercise type, calories burned, etc.). Accordingly, the event type widget may indicate a user's glucose level at the start of an event, one hour after the event, and/or two hours after the event. Other types of widgets may encompass widgets which do not fit into the other three categories. For example, another type widget may be a widget which displays a trend graph of a user's average glucose level for a 24 hour period over the past 14 days.

Figure 19:
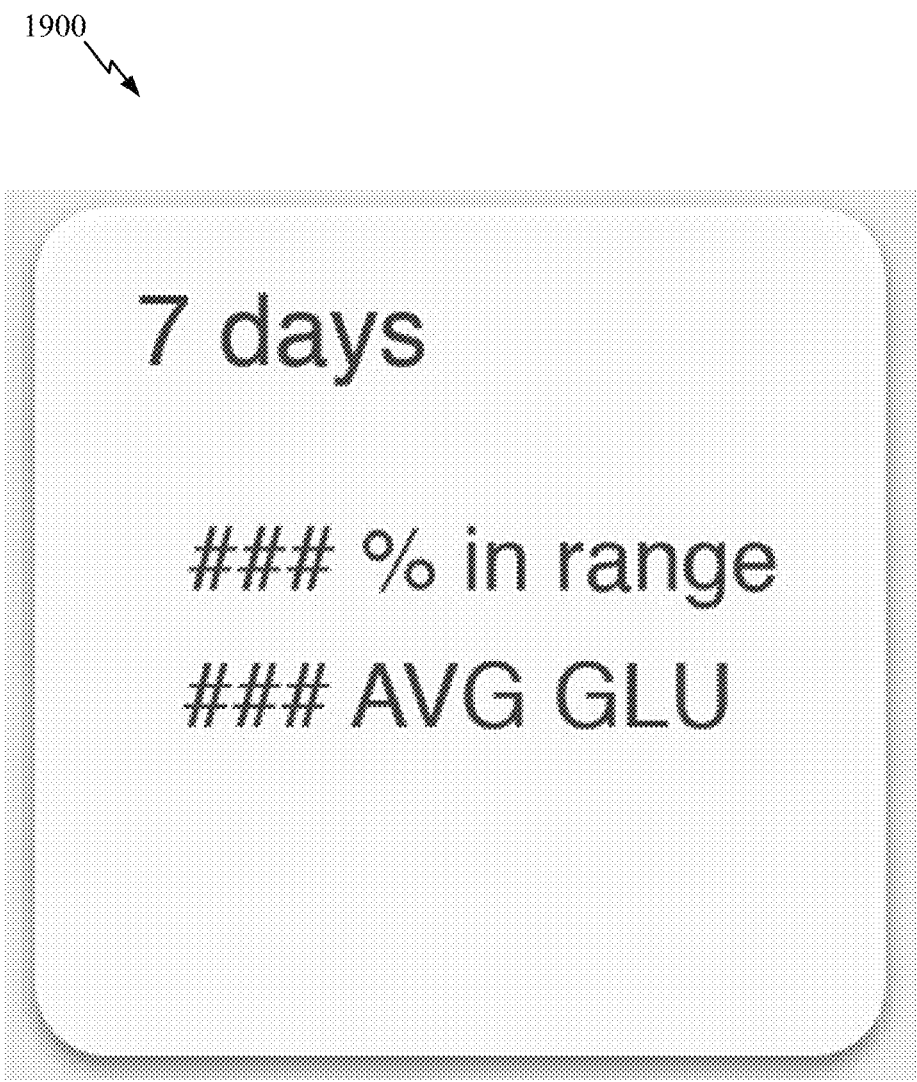
FIG. 19 illustrates a wireframe of an example summary widget, in accordance with some example aspects of the present disclosure.

FIG. 19 illustrates an example summary widget 1900, in accordance with some example aspects of the present disclosure. As shown in FIG. 19, the summary widget 1900 may provide a summary of a user's percentage of time spent in a target glucose range and the user's average glucose over a seven day period.

Figure 20:
FIG. 20 illustrates a wireframe of another example summary widget, in accordance with some example aspects of the present disclosure.

FIG. 20 illustrates another example summary widget 2000, in accordance with some example aspects of the present disclosure. As shown in FIG. 20, the summary widget 2000 may provide a summary of a user's average glucose, the user's standard deviation, and the user's glucose management indicator (GMI) percentage over a fourteen day period.

Figure 21:
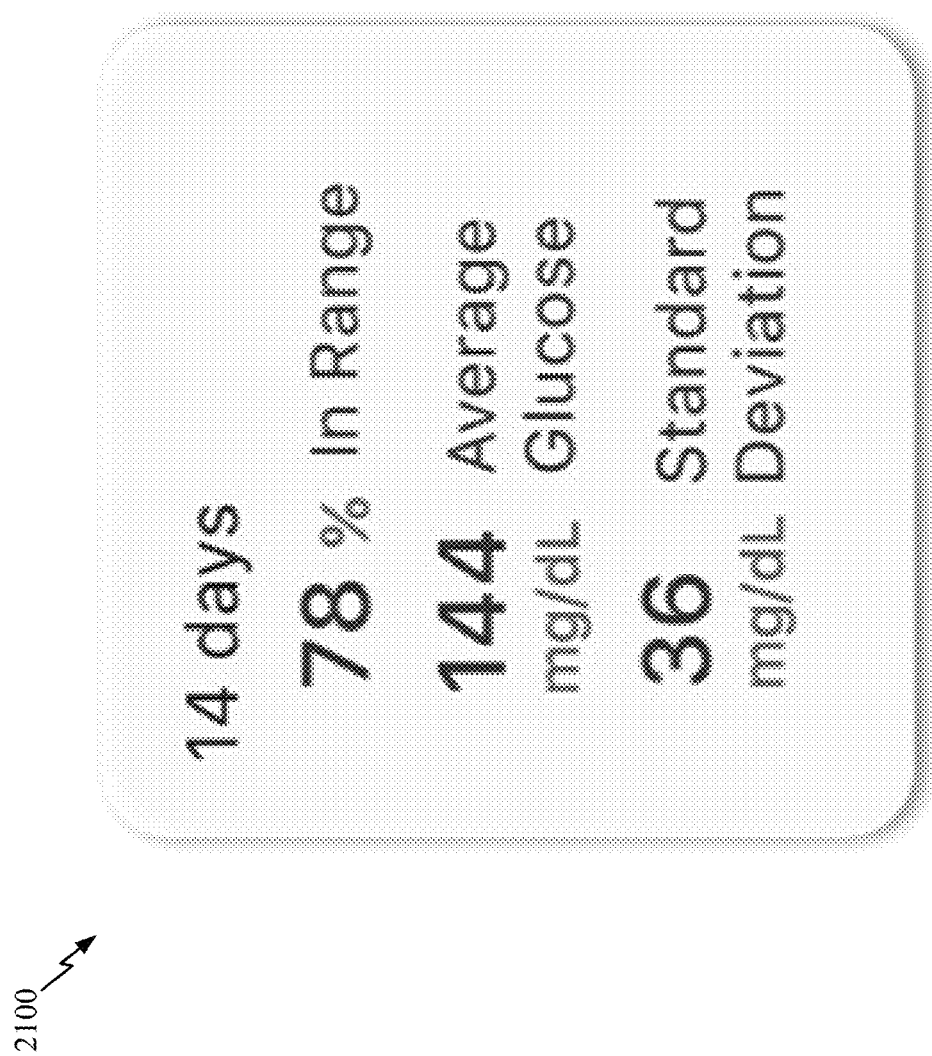
FIG. 21 illustrates another example summary widget, in accordance with some example aspects of the present disclosure.

FIG. 21 illustrates another example summary widget 2100, in accordance with some example aspects of the present disclosure. As shown in FIG. 21, the summary widget 2100 may provide a summary of a host's percentage of time spent in a target glucose range, the host's average glucose, and the host's standard deviation over a defined time period, such as a fourteen day period.

Figure 22:
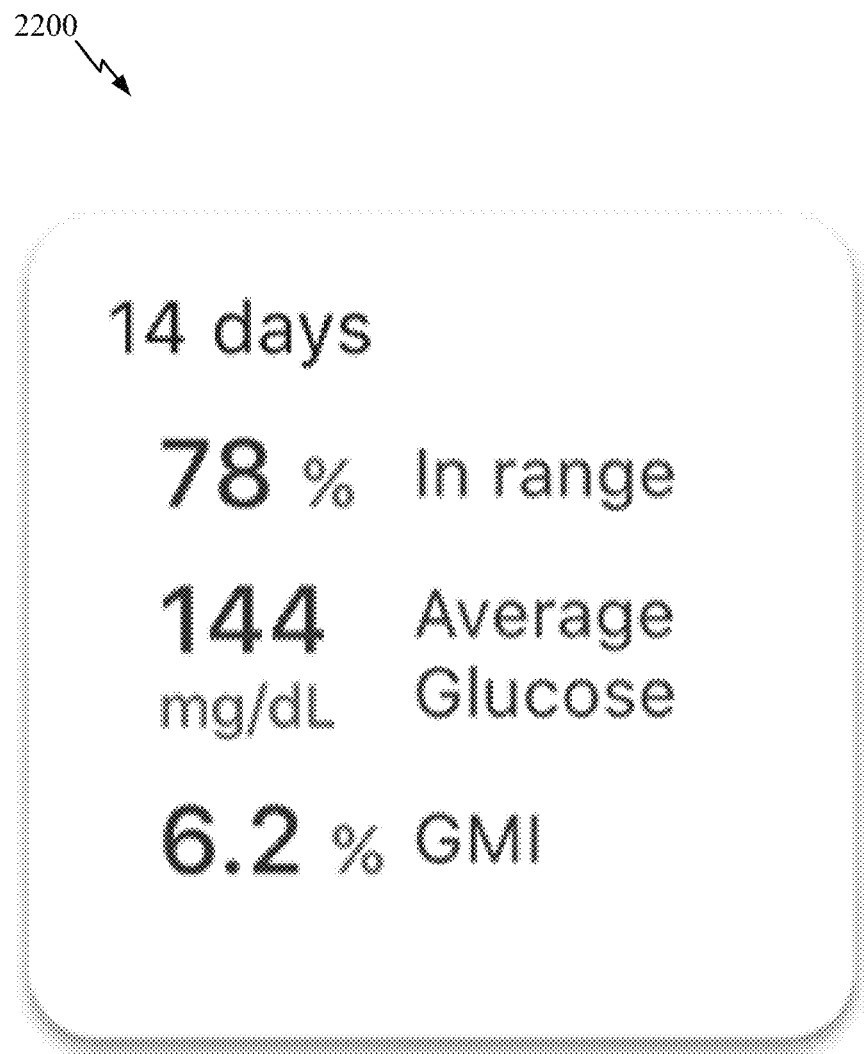
FIG. 22 illustrates another example summary widget, in accordance with some example aspects of the present disclosure.

FIG. 22 illustrates another example summary widget 2200, in accordance with some example aspects of the present disclosure. As shown in FIG. 22, the summary widget 2200 may provide a summary of a host's percentage of time spent in a target glucose range, the host's average glucose, and the host's GMI percentage over a defined time period, such as a fourteen day period.

Figure 23:
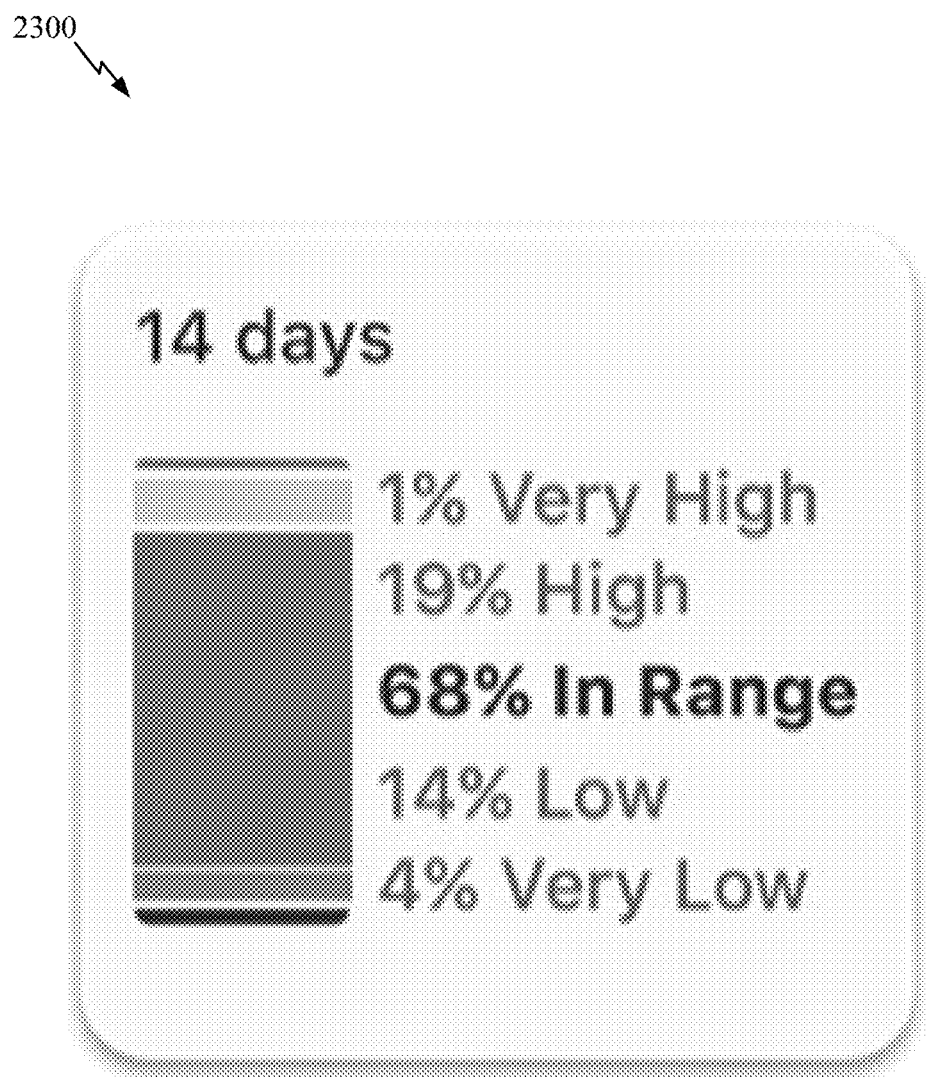
FIG. 23 illustrates another example summary type widget, in accordance with some example aspects of the present disclosure.

FIG. 23 illustrates another example summary widget 2300, in accordance with some example aspects of the present disclosure. As shown in FIG. 23, the summary widget 2300 may provide a summary of a user's percentage of time spent in a target glucose range, very high and high glucose ranges, and very low and low glucose ranges over a defined time period, such as a fourteen day period. As shown, the summary widget 2300 may provide both numerical values and a stacked bar graph representing the percentages. The stacked bar graph may be associated with color coding representing severity of the ranges.

Figure 24:
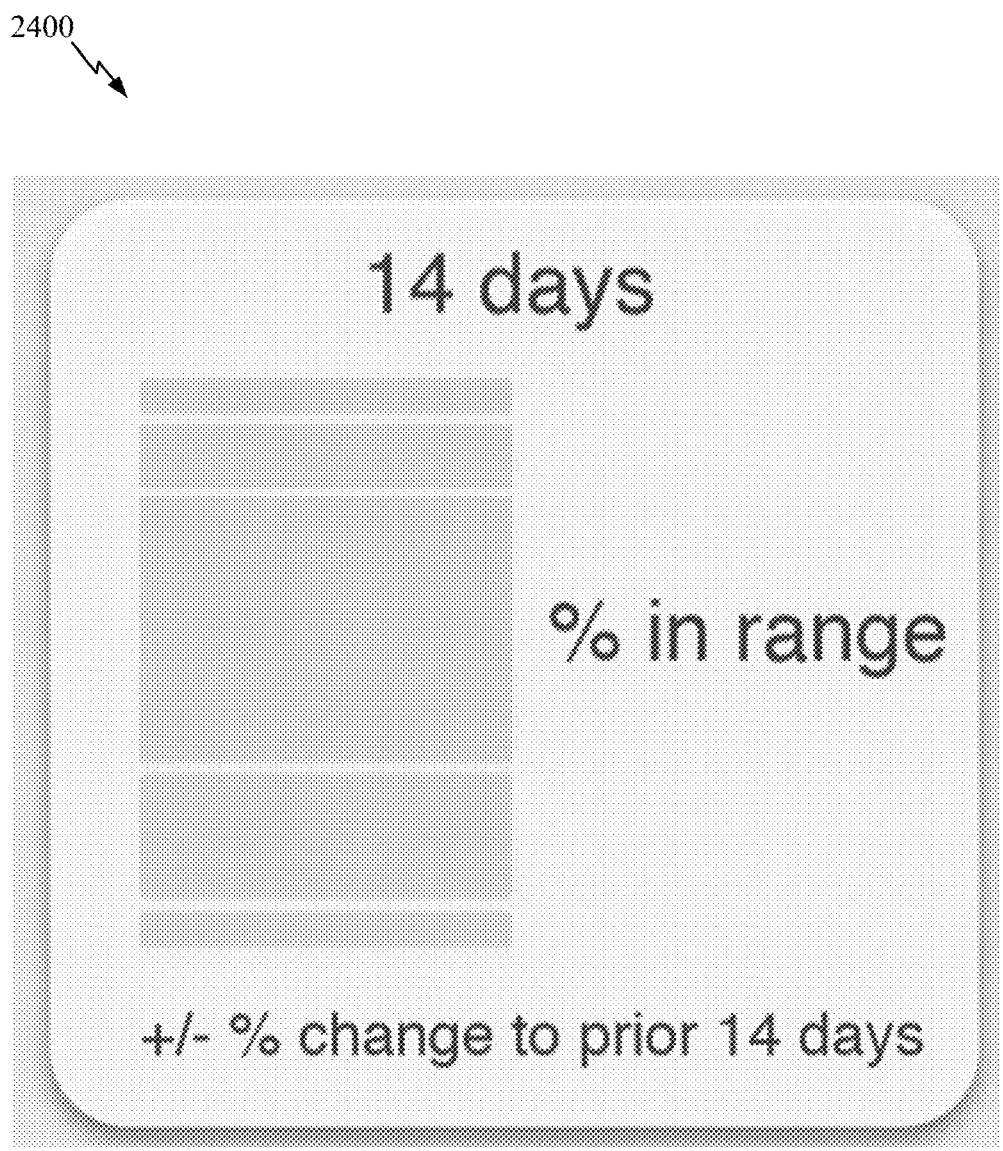
FIG. 24 illustrates another example summary type widget, in accordance with some example aspects of the present disclosure.

FIG. 24 illustrates another example summary widget 2400, in accordance with some example aspects of the present disclosure. As shown in FIG. 24, the summary widget 2400 may provide the information of the summary widget 2300 in FIG. 23, a summary of a user's percentage of time spent in a target glucose range, very high and high glucose ranges, and very low and low glucose ranges over a defined time period, such as a fourteen day period, and further provide an indication of the positive or negative percentage of change compared to a prior similar defined time period, such as a prior fourteen day period.

Figure 25A:
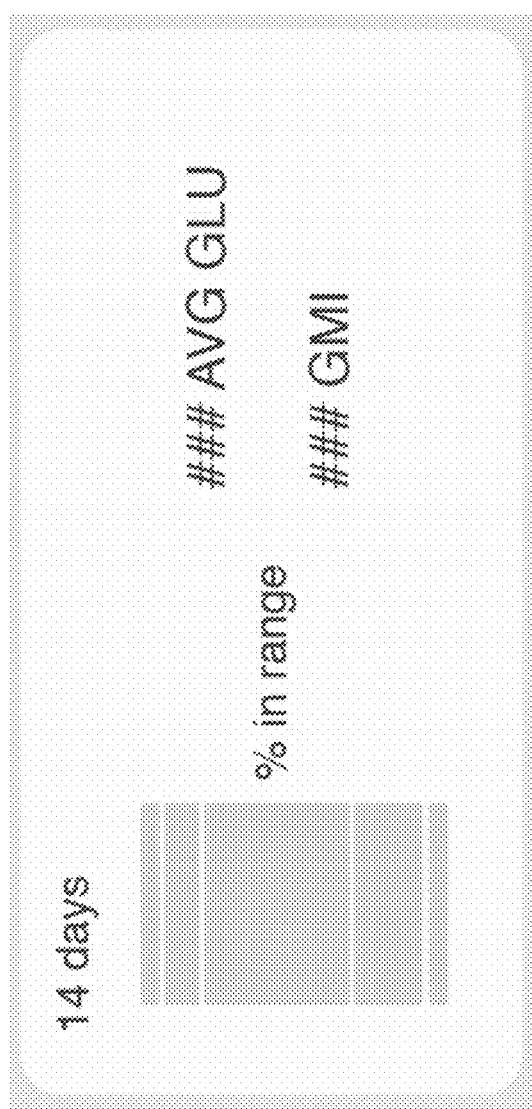
FIGS. 25A and 25B illustrates another example summary type widget, and its corresponding wireframe, respectively, in accordance with some example aspects of the present disclosure.
Figure 25B:
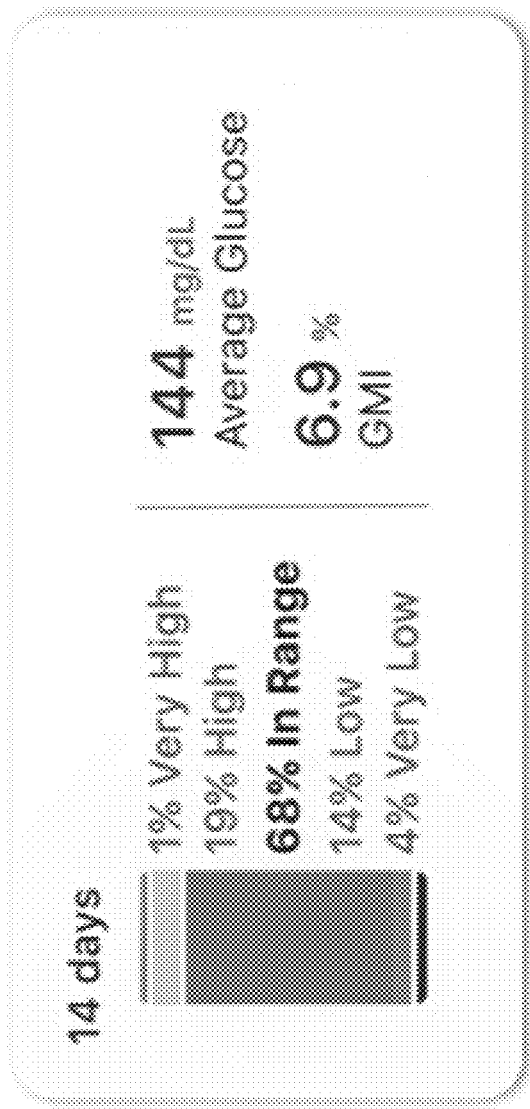

FIGS. 25A and 25B illustrate another example summary type widget 2500*b*, and its corresponding wireframe 2500*a*, in accordance with some example aspects of the present disclosure. As shown in FIGS. 25A and 25B, the summary type widget 2500*b* may provide the information in the summary widget 2300 in FIG. 23, a summary of a user's percentage of time spent in a target glucose range, very high and high glucose ranges, and very low and low glucose ranges over a defined time period, such as a fourteen day period, and further provide the host's average glucose, and the host's GMI percentage over a same or different defined time period.

Figure 26B:
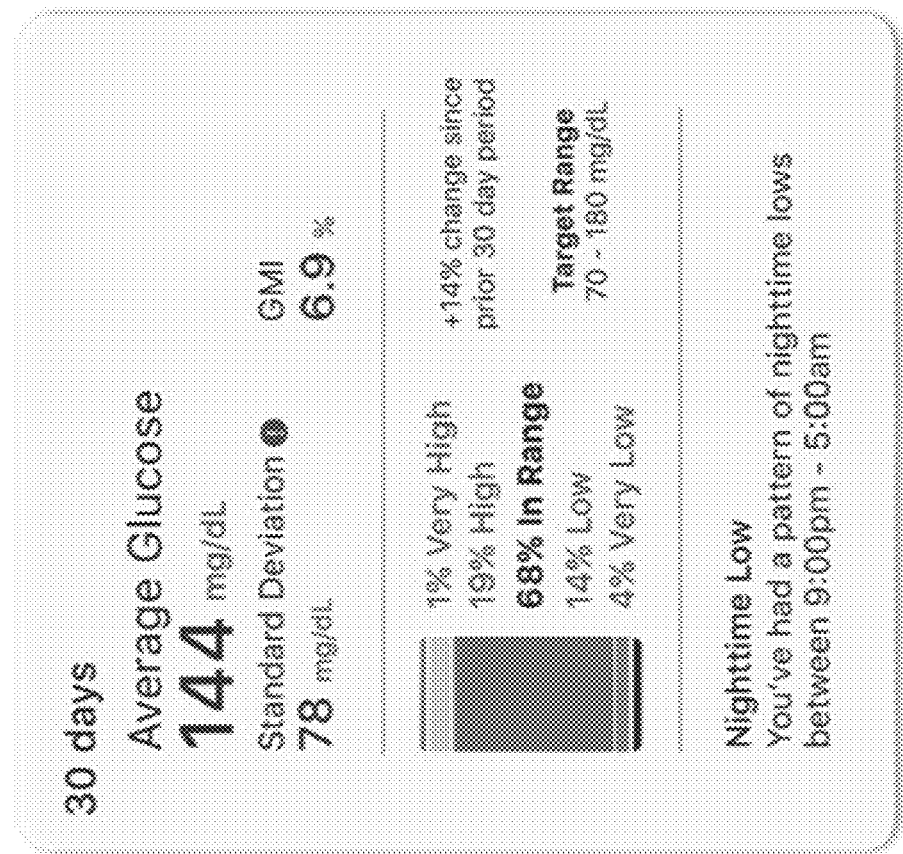
FIGS. 26A and 26B illustrate another example summary type widget, and its corresponding wireframe, respectively, in accordance with some example aspects of the present disclosure.
Figure 26A:
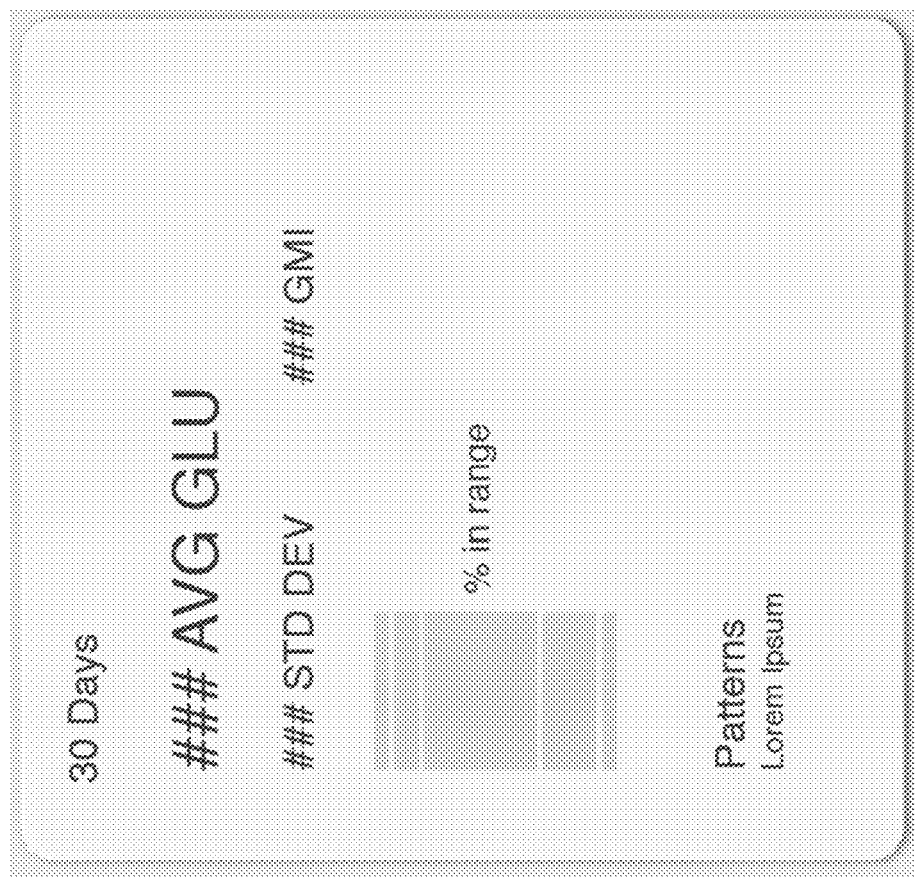

FIGS. 26A and 26B illustrate another example summary type widget 2600*b*, and its corresponding wireframe 2600*a*, in accordance with some example aspects of the present disclosure. As shown in FIGS. 26A and 26B, the summary widget 2600*b* may provide the information of the summary widget 2500*b* in FIGS. 25A and 25B, a summary of a user's percentage of time spent in a target glucose range, very high and high glucose ranges, and very low and low glucose ranges over a defined time period, such as a thirty day period, plus an indication of the positive or negative percentage of change compared to a prior similar defined time period, such as a prior thirty day period, the user's average glucose, the user's GMI percentage, and may further provide an indication of a pattern (e.g., user's daytime high or nighttime low glucose patterns) over the defined time period. As shown, the indication may be provided as a narrative text.

Figure 27:
FIG. 27 illustrates a wireframe of another example summary type widget, in accordance with some example aspects of the present disclosure.

FIG. 27 illustrates another example summary widget 2700, in accordance with some example aspects of the present disclosure. As shown in FIG. 27, the summary widget 2700 may provide a summary of a user's percentage of time spent in a target glucose range comparing percentages for the current week, last week, this month, and year to date (YTD).

Figure 28:
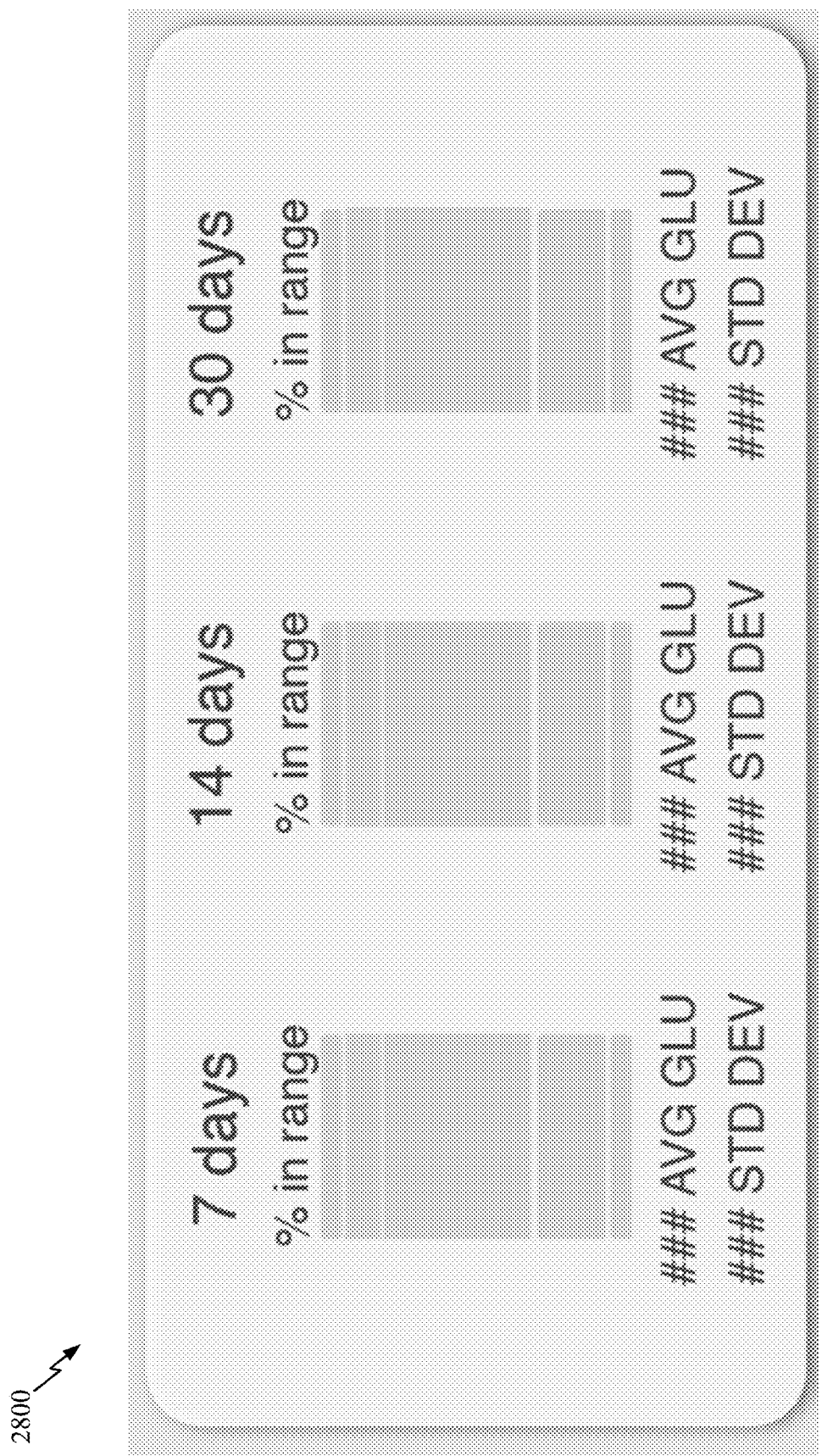
FIG. 28 illustrates a wireframe of another example summary type widget, in accordance with some example aspects of the present disclosure.

FIG. 28 illustrates another example summary widget 2800, in accordance with some example aspects of the present disclosure. As shown in FIG. 28, the summary widget 2800 may provide a summary of a user's percentage of time spent in a target glucose range comparing the last seven days, the last fourteen days, and the last thirty days plus an indication of the user's average glucose and standard deviation over the last seven days, the last fourteen days, and the last thirty days. As shown, the percentage of time in range may be provided as a stacked bar graph.

Figure 29:
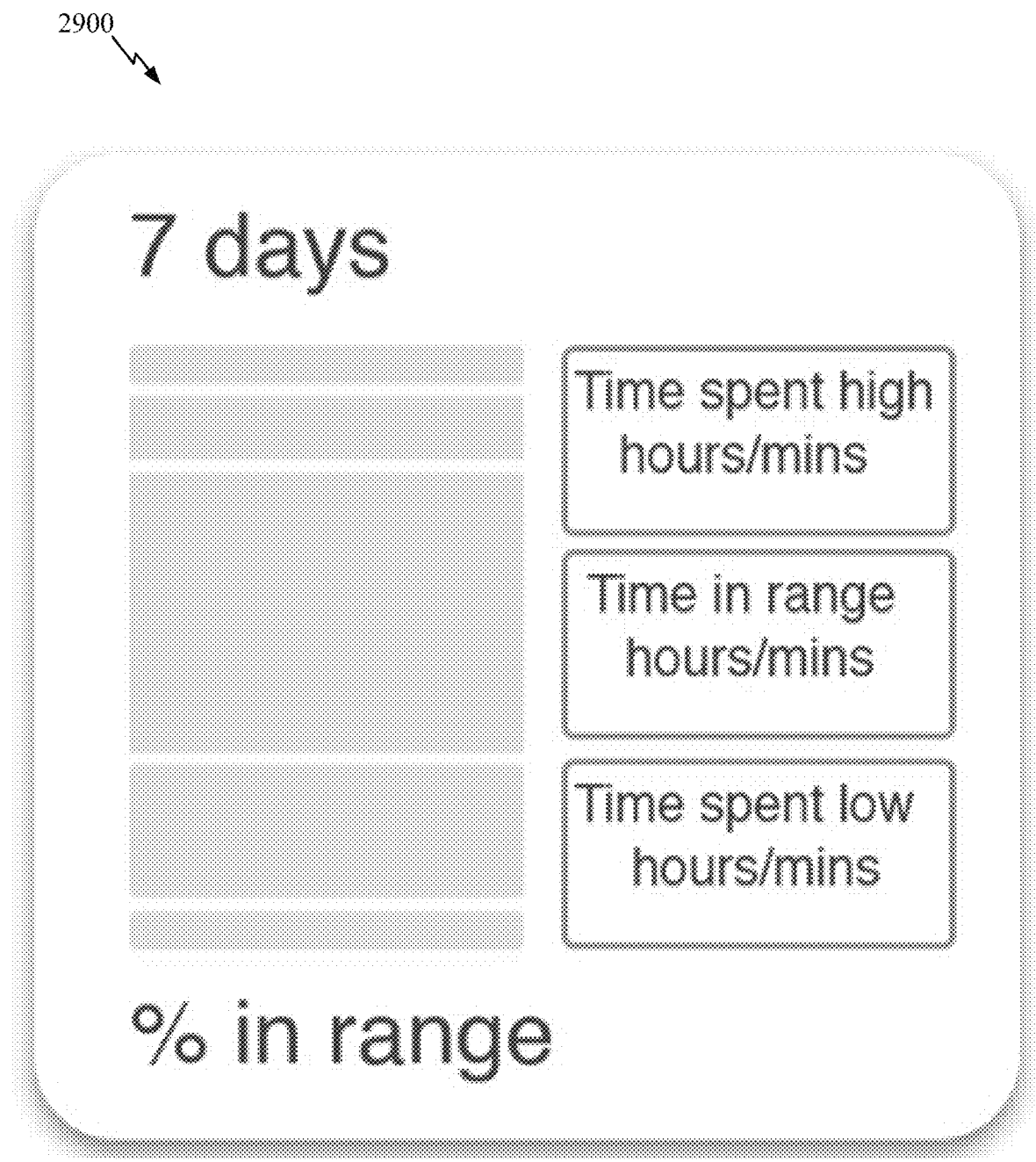
FIG. 29 illustrates a wireframe of another example summary type widget, in accordance with some example aspects of the present disclosure.

FIG. 29 illustrates another example summary widget 2900, in accordance with some example aspects of the present disclosure. As shown in FIG. 29, a summary widget 2900 may provide a summary of a user's percentage of time spent in a target glucose range, very high and high glucose ranges, and very low and low glucose ranges and an indication of the hours/minutes the user spent in each of these ranges over a defined time period, such as a seven day period. As shown, the percentage of time spent in range may be represented by a stacked bar graph and the stacked bar graph may be associated with values for the number of hours spent in various ranges associated with the stacked bar graph.

Figure 30:
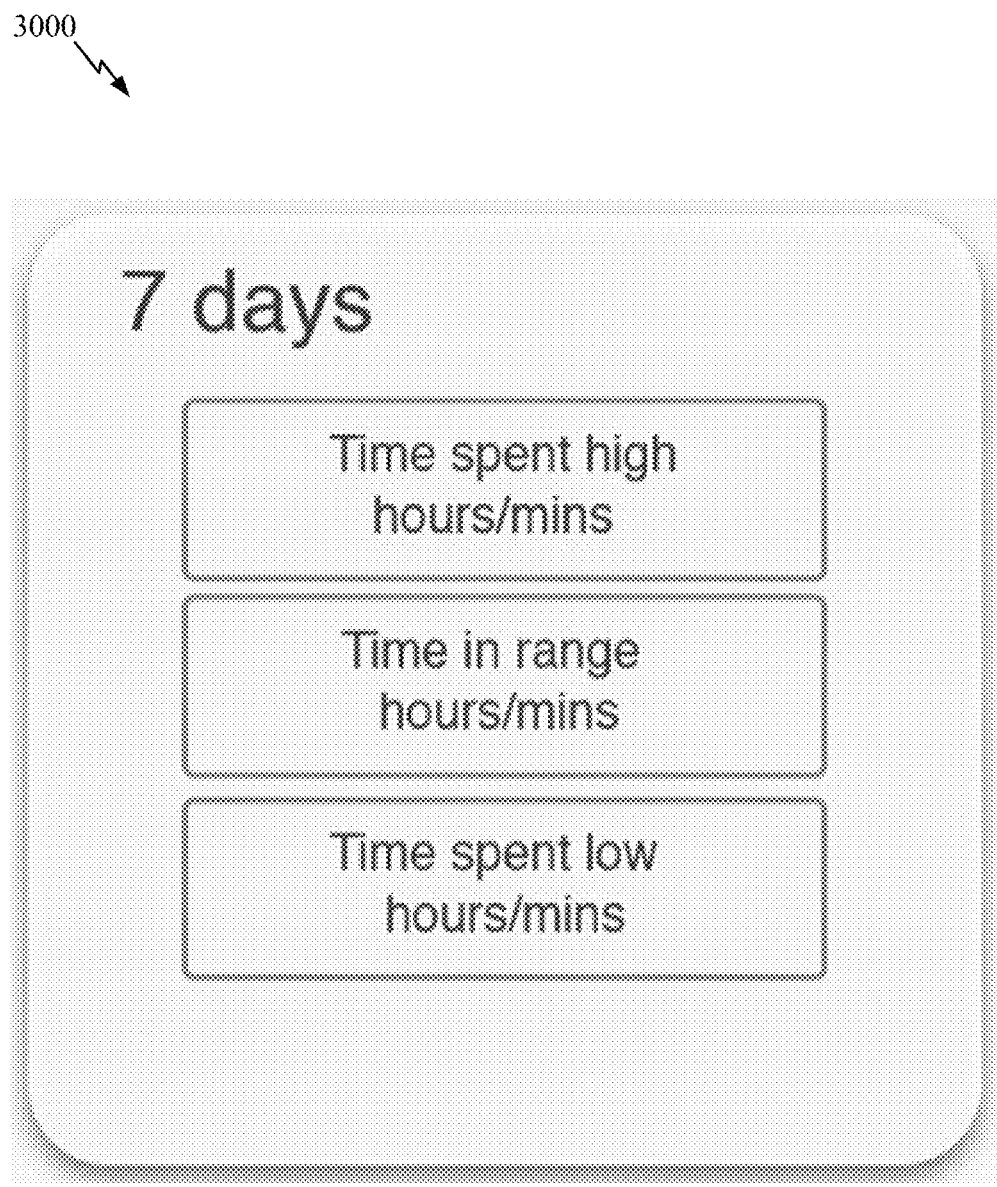
FIG. 30 illustrates a wireframe of another example summary type widget, in accordance with some example aspects of the present disclosure.

FIG. 30 illustrates another example summary widget 3000, in accordance with some example aspects of the present disclosure. As shown in FIG. 30, the summary widget 3000 may provide a summary of the hours/minutes a user spent in a target glucose range, a high glucose range, and a low glucose range over a defined time period, such as a seven day period.

Figure 31:
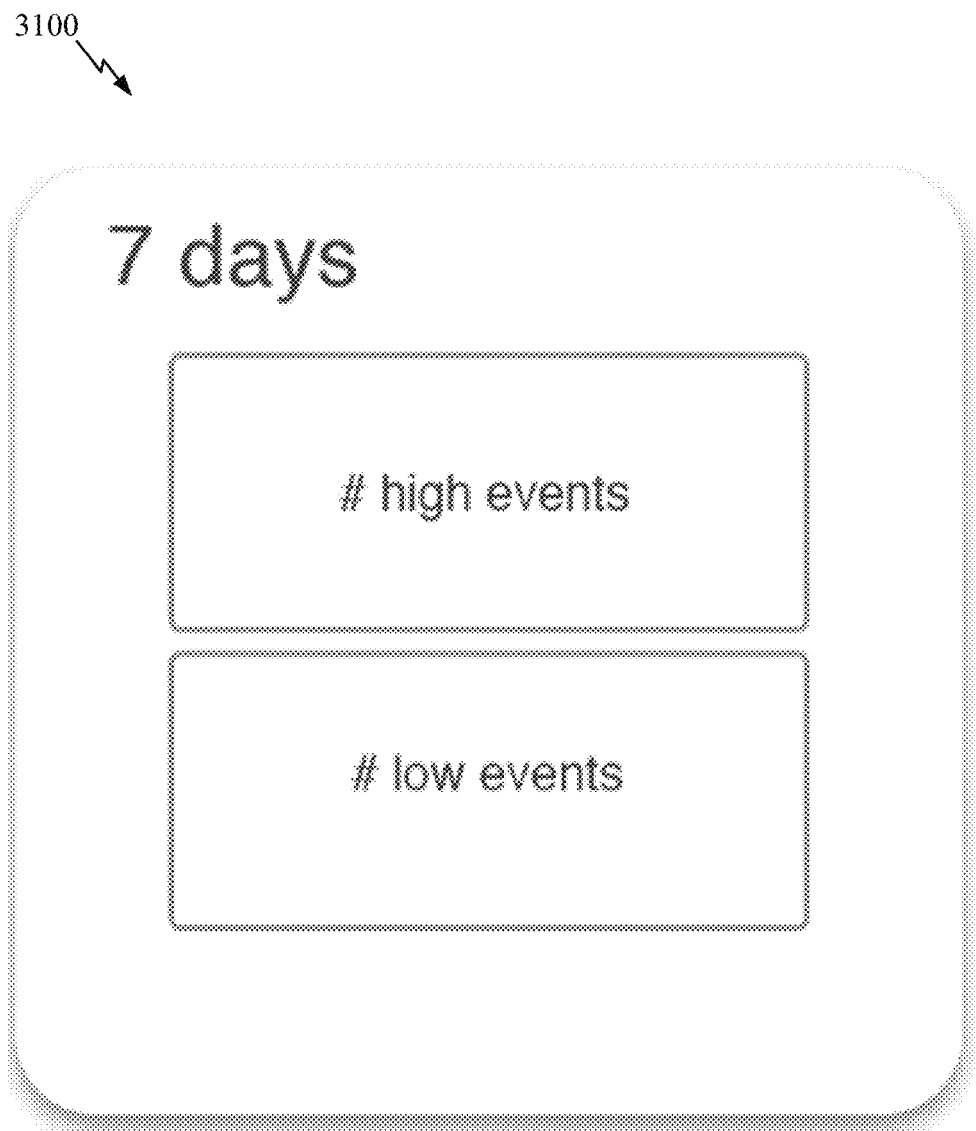
FIG. 31 illustrates a wireframe of another example summary type widget, in accordance with some example aspects of the present disclosure.

FIG. 31 illustrates another example summary widget 3100, in accordance with some example aspects of the present disclosure. As shown in FIG. 31, the summary widget 3100 may provide a summary of a number of high and low events a host participated in over a defined time period, such as a seven day period.

Figure 32:
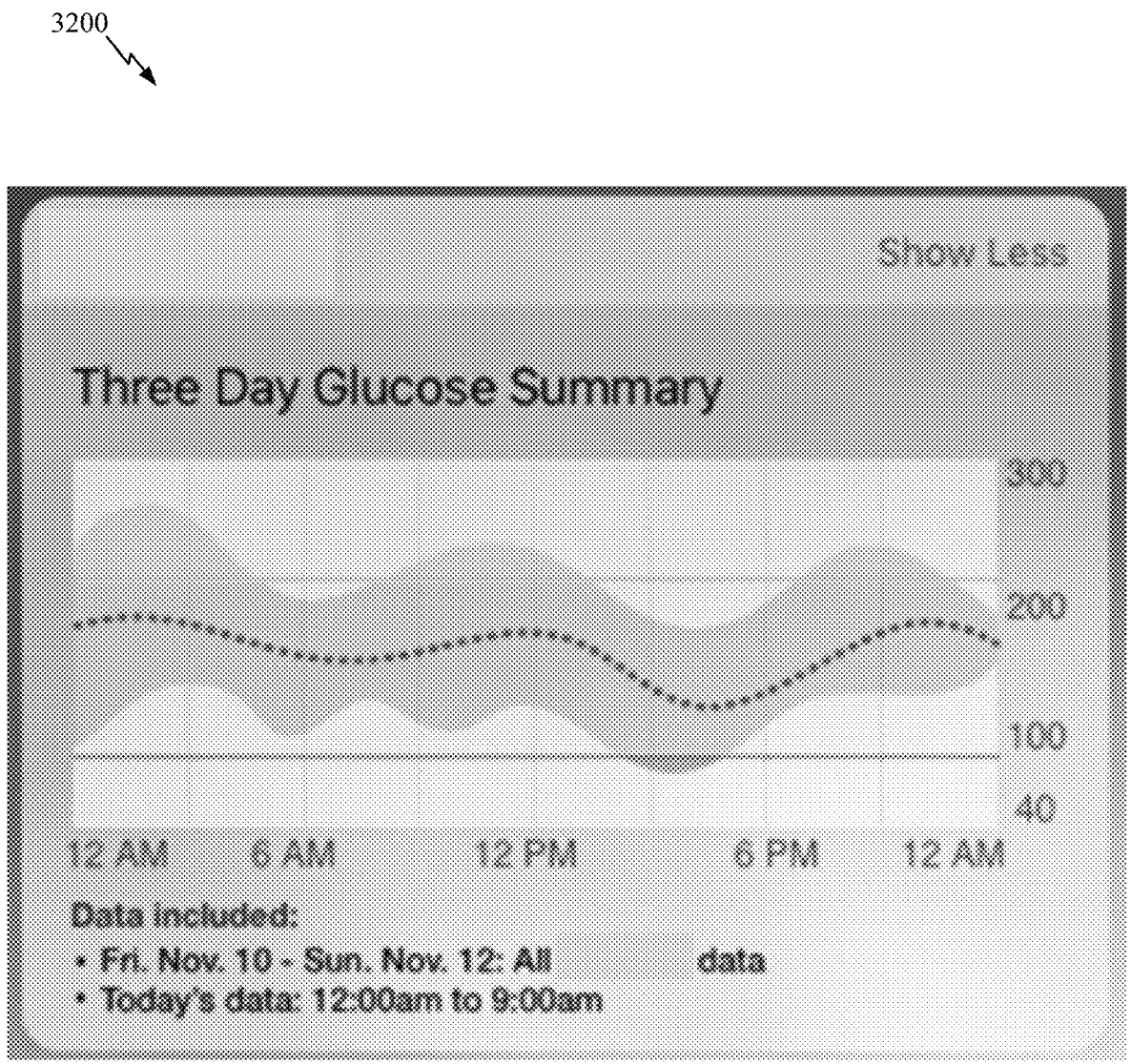
FIG. 32 illustrates another example summary type widget, in accordance with some example aspects of the present disclosure.

FIG. 32 illustrates another example summary widget 3200, in accordance with some example aspects of the present disclosure. As shown in FIG. 32, the summary widget 3200 may provide a summary of a user's time in range, which may presented in a graph with a line of best fit indicating the user's time in range trend over a defined time period, such as a twelve hour period (e.g., 12:00 AM-12:00 AM), for a particular duration, such as three days. An indication of the data included in the summary graph may also be included in the summary widget 3200.

Figures 33A, 33B:
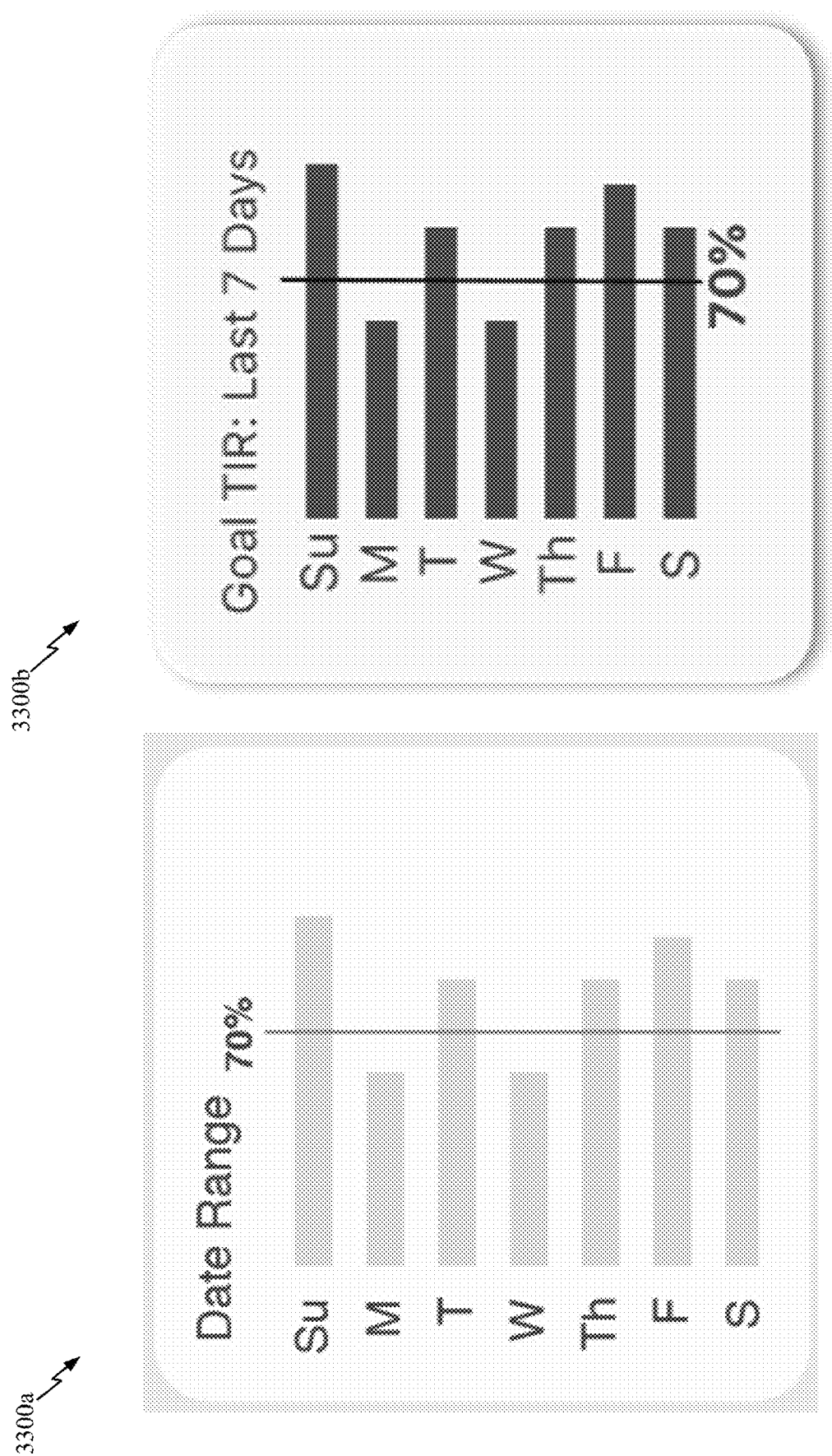
FIGS. 33A and 33B illustrate an example motivation type widget, and its corresponding wireframe, respectively, in accordance with some example aspects of the present disclosure.

FIGS. 33A and 33B illustrate an example motivation type widget 3300b, and its corresponding wireframe 3300a, in accordance with some example aspects of the present disclosure. As shown in FIGS. 33A and 33B, the motivation type widget 3300b may provide a horizontal bar graph illustrating a user's percentage of time spent in a target glucose range per day for a particular duration, such as a seven day period, compared to a goal percentage of time to be spent in the target glucose range per day.

Figure 33C:
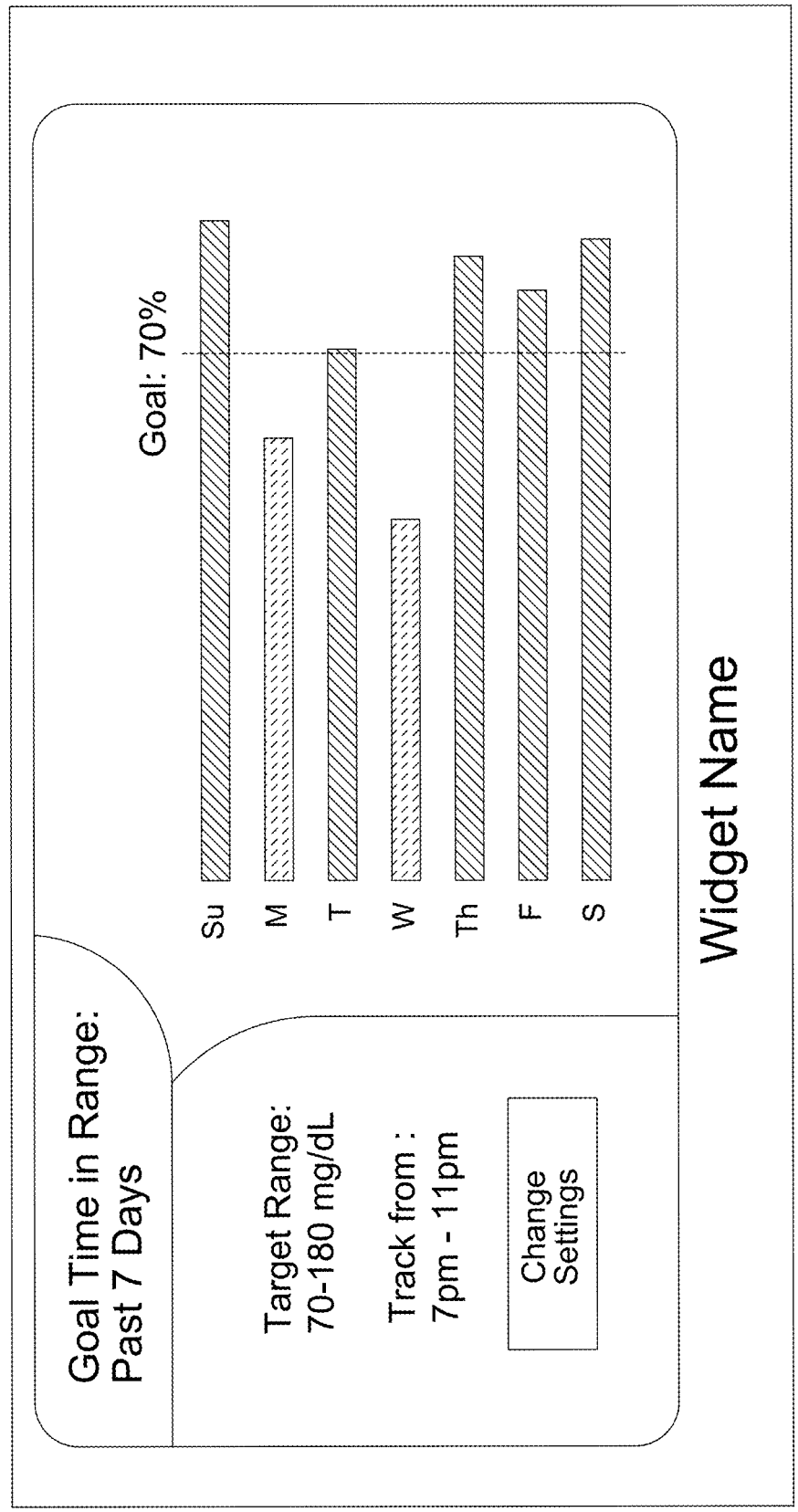
FIGS. 33C-33E illustrate the example motivation type widget illustrated in FIG. 33B with additional features, in accordance with some example aspects of the present disclosure.
Figure 33E:
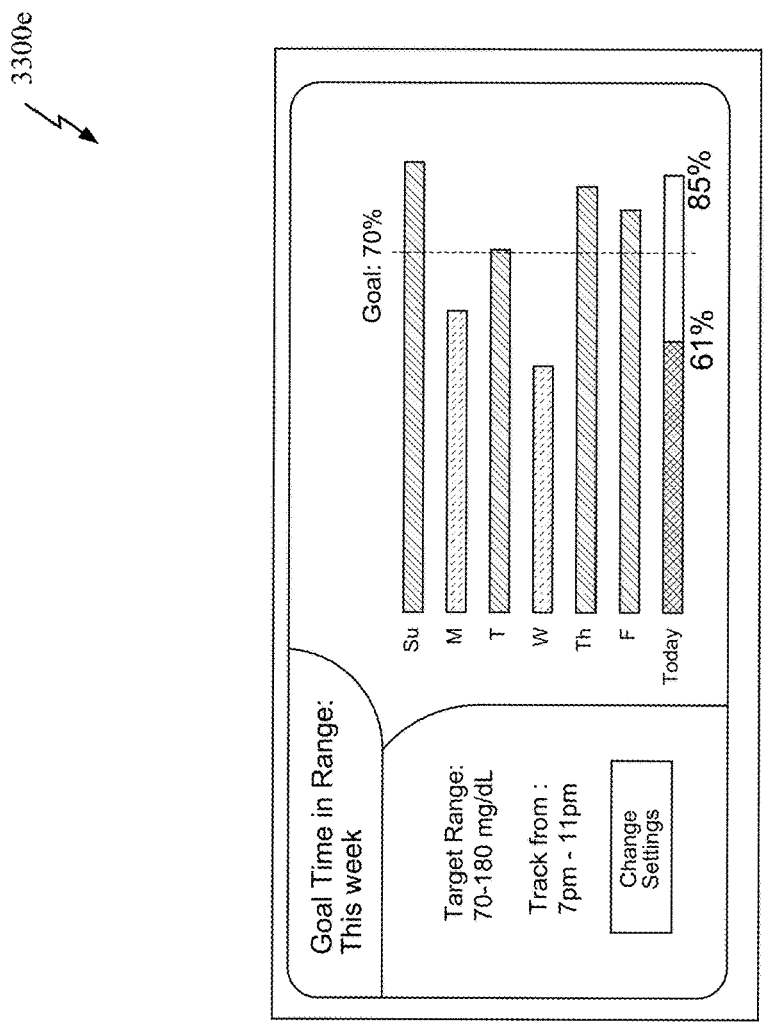
Figure 33D:
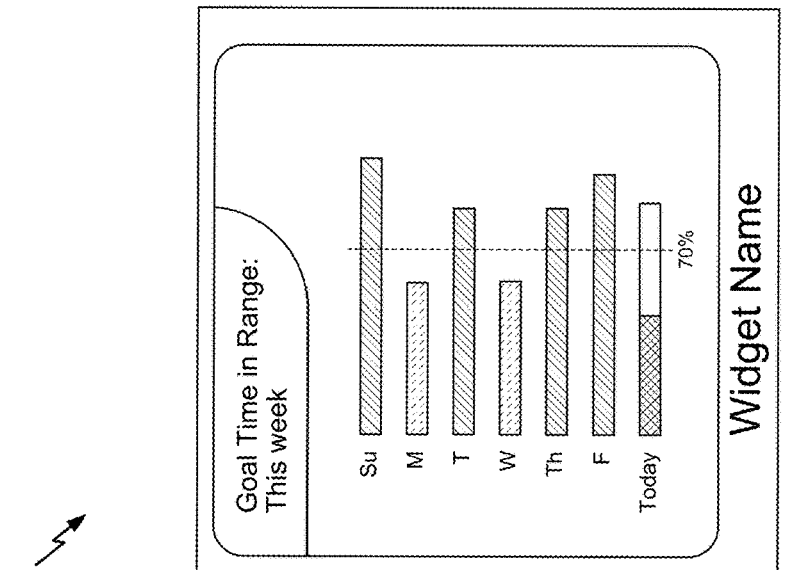

FIGS. 33C-33E illustrate the example motivation type widget 3300C-3300E which is similar to the motivation type widget 3300B illustrated in FIG. 33B but has additional features, in accordance with some example aspects of the present disclosure. For example, as shown in FIG. 33C, additional features in the example motivation type widget 3300C may include an indication of a time period when information illustrated in the widget was collected. In FIG. 33C, the motivation type widget is showing a horizontal bar graph for data collected for the user between 7 pm and 11 pm. The "track from" time period may be changed to reflect different bar graphs for the user for different data sets from different time periods.

As another example, as shown in FIG. 33D, additional features in the example motivation type widget 3300D may include a progress bar. The progress bar may indicate to the user what percentage of the current day the user has spent in a target glucose range. The progress bar may be provided to motivate a user to meet their personalized goal time in range for the current day. For example, the progress bar may indicate to a user in the morning that their glucose levels have been within their target glucose range for 61% of the day. Where the user has previously set a goal to stay within this target glucose range for 70% of the day (e.g., shown as the vertical dashed line), the progress bar may provide information to allow a user to know where they are at with respect to their goal, and in some cases, motivate the user to reach this goal.

In some aspects, as shown in FIG. 33E, additional features in the example motivation type widget 3300E may include both additional features illustrated in FIG. 33C and FIG. 33D (e.g., an indication of a time period when information illustrated in the widget was collected and a progress bar).

Figure 34:
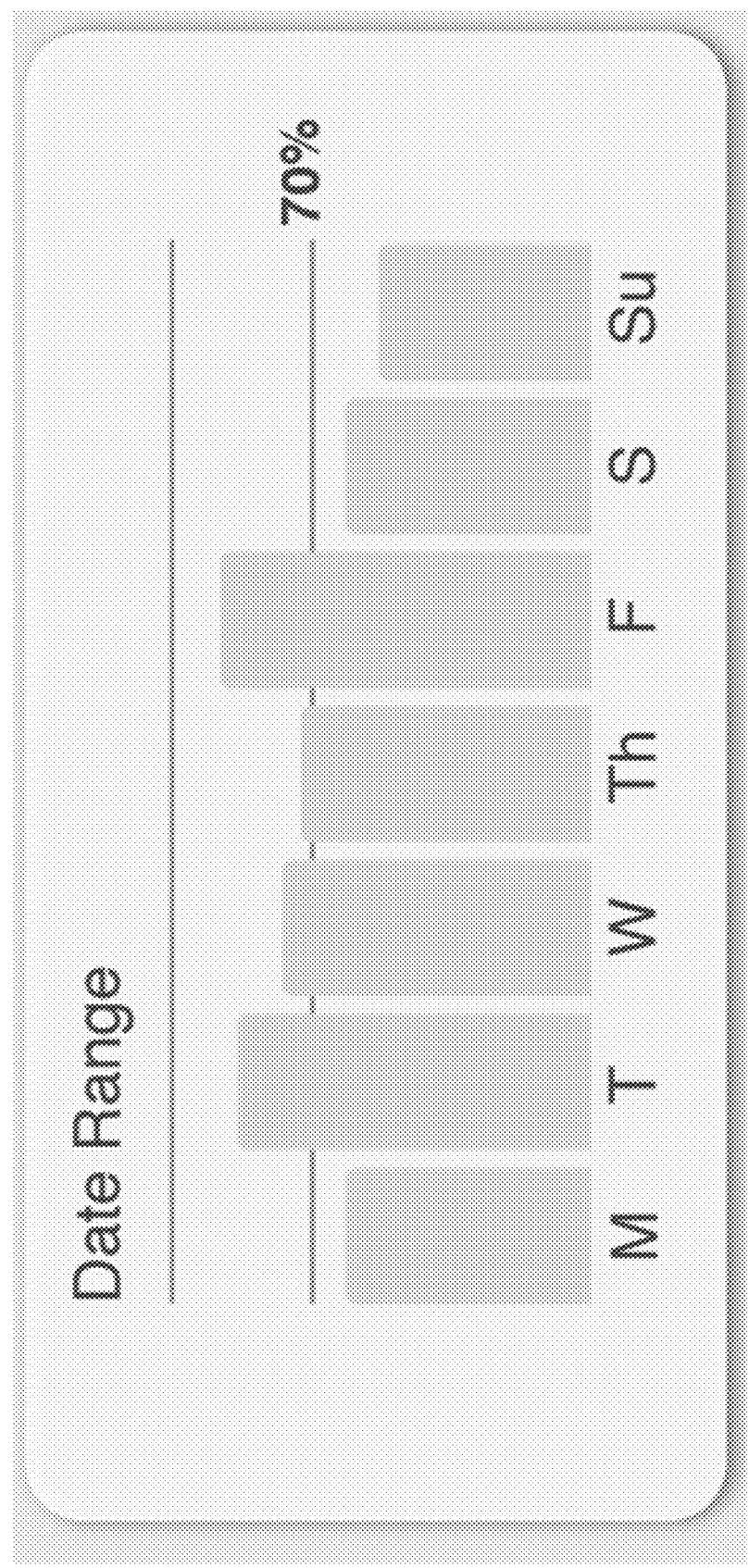
FIG. 34 illustrates another example motivation type widget, in accordance with some example aspects of the present disclosure.

FIG. 34 illustrates another example motivation type widget 3400, in accordance with some example aspects of the present disclosure. As shown in FIG. 34, the motivation type widget 3400 may provide a vertical bar graph illustrating a user's percentage of time spent in a target glucose range per day for a particular duration, such as a seven day period, compared to a goal percentage of time (e.g., 70%) to be spent in the target glucose range per day.

Figures 35A, 35B:
FIGS. 35A and 35B illustrate another example motivation type widget, and its corresponding wireframe, respectively, in accordance with some example aspects of the present disclosure.

FIGS. 35A and 35B illustrate another example motivation type widget 3500b, and its corresponding wireframe 3500a, in accordance with some example aspects of the present disclosure. As shown in FIGS. 35A and 35B, the motivation type widget 3500b may provide a vertical graph bar illustrating a user's percentage of time spent in a target glucose range for today compared to a goal percentage of time to be spent in the target glucose range per day. Although not shown, the motivation type widget 3500b may, in some aspects, provide a vertical graph bar illustrating a user's percentage of time spent in a target glucose range for a current week compared to a goal percentage of time to be spent in the target glucose range per week.

Figure 36:
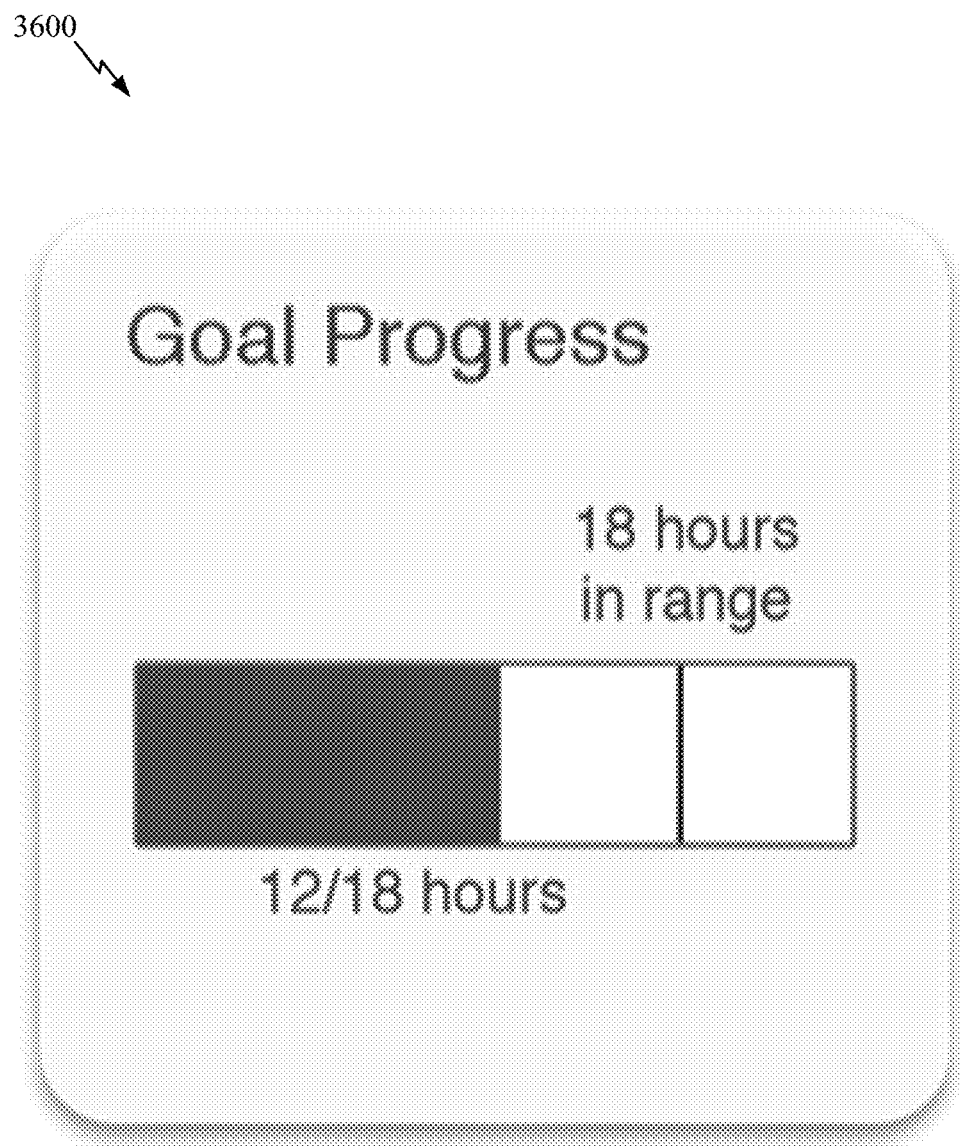
FIG. 36 illustrates another example motivation type widget, in accordance with some example aspects of the present disclosure.

FIG. 36 illustrates another example motivation type widget 3600, in accordance with some example aspects of the present disclosure. As shown in FIG. 36, the motivation type widget 360 may provide a horizontal bar graph illustrating a number of hours a user spent in a target glucose range today compared to a goal number of hours to be spent in the target glucose range per day. Although not shown, the motivation type widget 3600 may, in some aspects, provide a vertical graph bar illustrating a user's percentage of time spent in a target glucose range for a current week compared to a goal percentage of time to be spent in the target glucose range per week.

Figure 37:
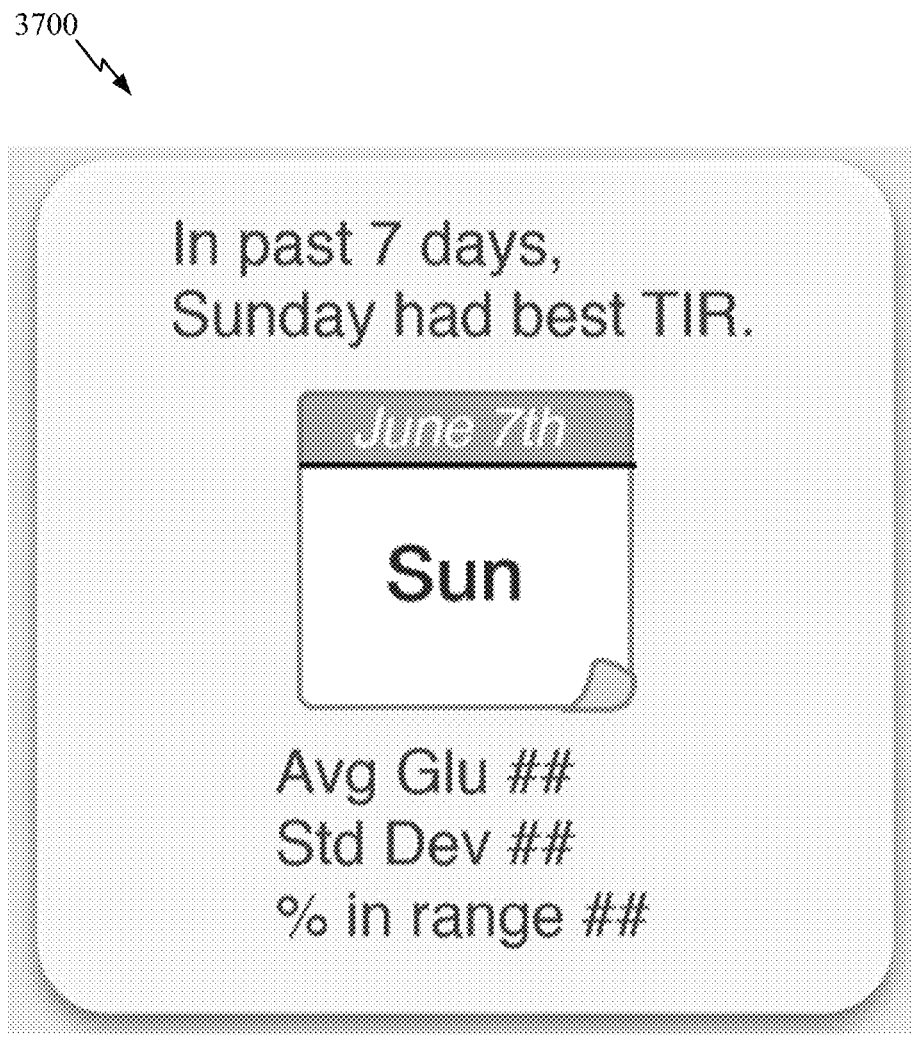
FIG. 37 illustrates a wireframe of another example motivation type widget, in accordance with some example aspects of the present disclosure.

FIG. 37 illustrates another example motivation type widget 3700, in accordance with some example aspects of the present disclosure. As shown in FIG. 37, the motivation type widget 3700 may provide an indication of a user's "best day" over a prior defined period of time, such as a prior seven day period. The motivation type widget 3700 may also include a summary of the user's average glucose, the user's percentage of time spent in a target glucose range, and the user's standard deviation for the indicated "best day".

Figure 38:
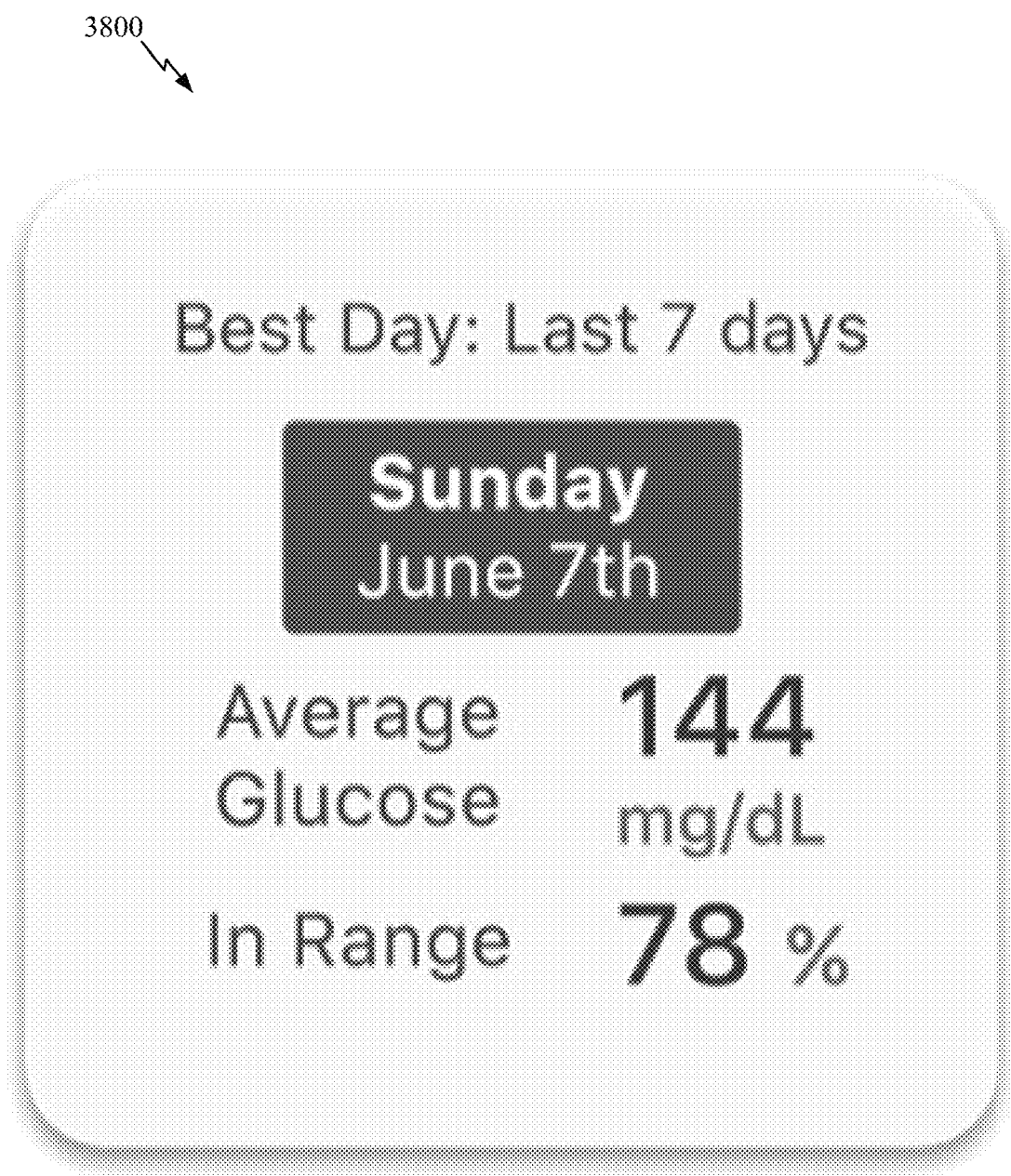
FIG. 38 illustrates another example motivation type widget, in accordance with some example aspects of the present disclosure.

FIG. 38 illustrates another example motivation type widget 3800, in accordance with some example aspects of the present disclosure. As shown in FIG. 38, the motivation type widget 3800 may provide an indication of a user's "best day" over a prior defined period of time, such as a prior seven day period. The widget may also include a summary of the user's average glucose and the user's percentage of time spent in a target glucose range for the indicated "best day".

Figure 39:
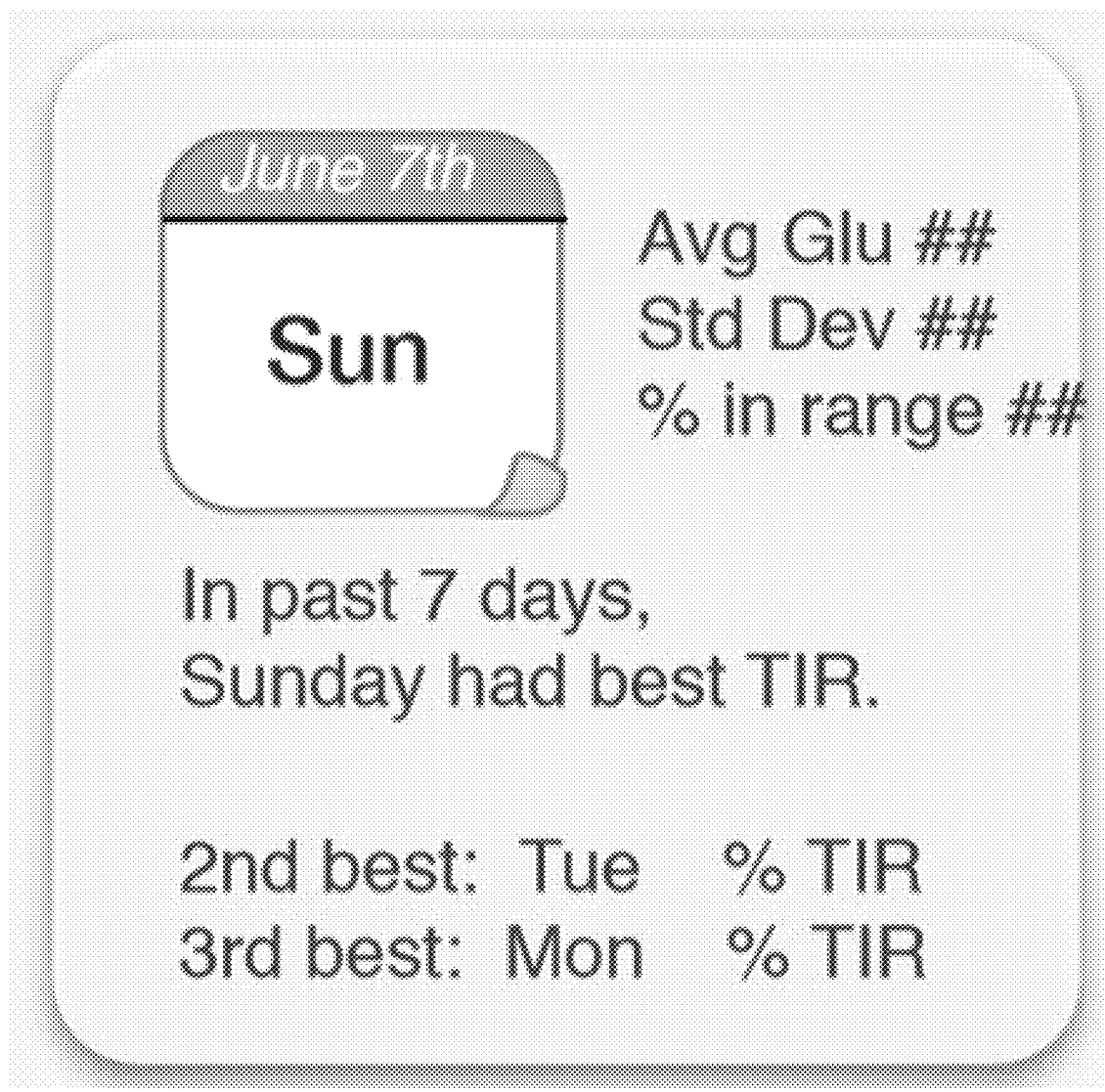
FIG. 39 illustrates another example motivation type widget, in accordance with some example aspects of the present disclosure.

FIG. 39 illustrates another example motivation type widget 3900, in accordance with some example aspects of the present disclosure. As shown in FIG. 39, the motivation type widget 3900 may provide an indication of a user's "best day" over a prior seven day period with a summary of the user's average glucose, the user's standard deviation, and the user's percentage of time spent in a target glucose range for the indicated "best day". The motivation type widget 3900 may also include an indication of the user's percentage of time spent in a target glucose range for the user's "second best day" and "third best day".

Figure 40:
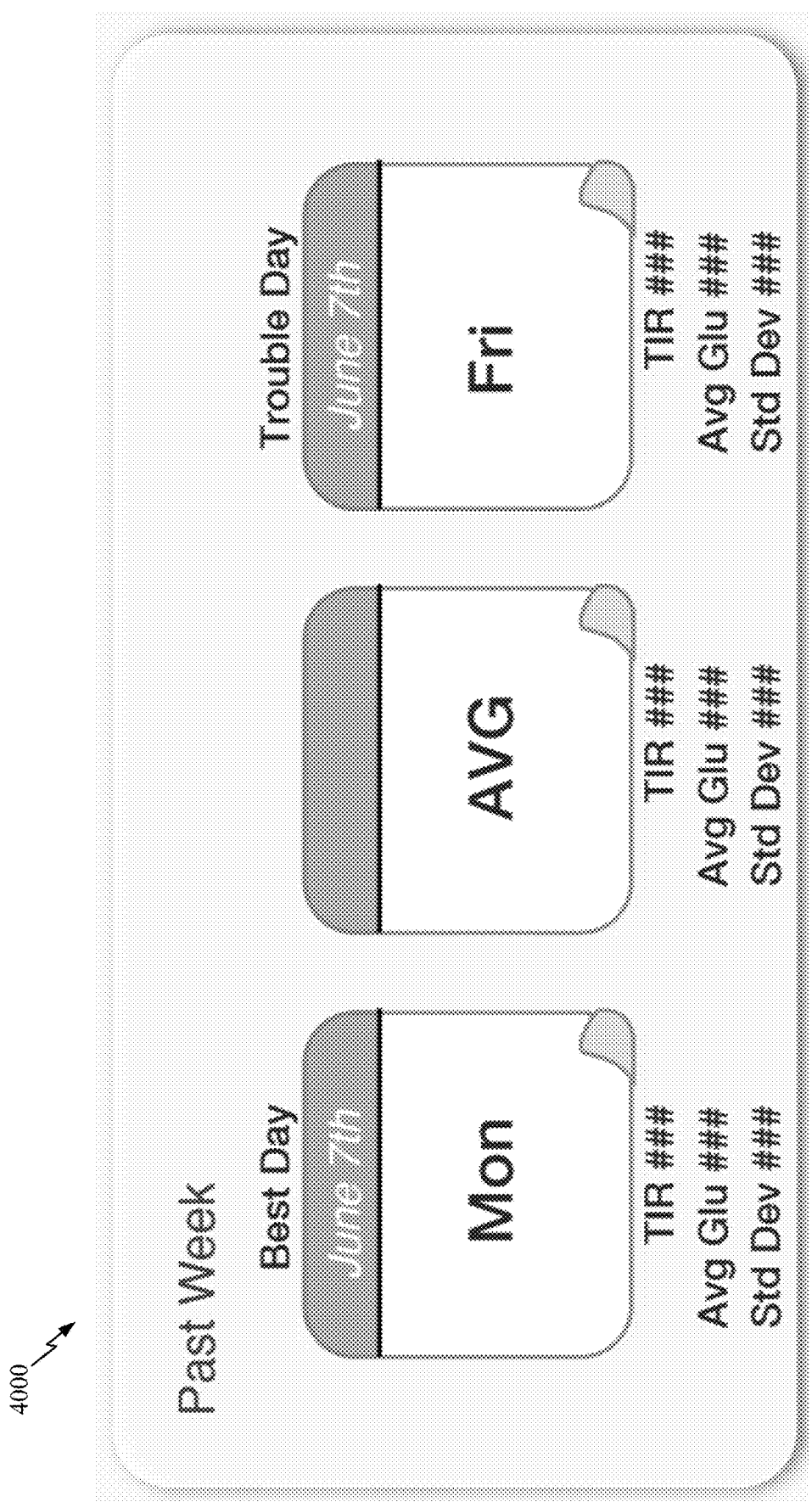
FIG. 40 illustrates another example motivation type widget, in accordance with some example aspects of the present disclosure.

FIG. 40 illustrates another example motivation type widget 4000, in accordance with some example aspects of the present disclosure. As shown in FIG. 40, the motivation type widget 4000 may provide a comparison of a user's "best day", "average day", and "trouble day" for a previous week. The motivation type widget 4000 may also include a summary of the user's average glucose, the user's standard deviation, and the user's percentage of time spent in a target glucose range for each of the indicated "best day", "average day", and "trouble day".

Figure 41:
FIG. 41 illustrates another example motivation type widget, in accordance with some example aspects of the present disclosure.

FIG. 41 illustrates another example motivation type widget 4100, in accordance with some example aspects of the present disclosure. As shown in FIG. 41, the motivation type widget 4100 may provide a comparison of a user's "best day", "average day", and "trouble day" for a prior defined period of time, such as a prior seven day period, with a summary of the user's average glucose and the user's percentage of time spent in a target glucose range for each of the indicated "best day", "average day", and "trouble day".

Figure 42:
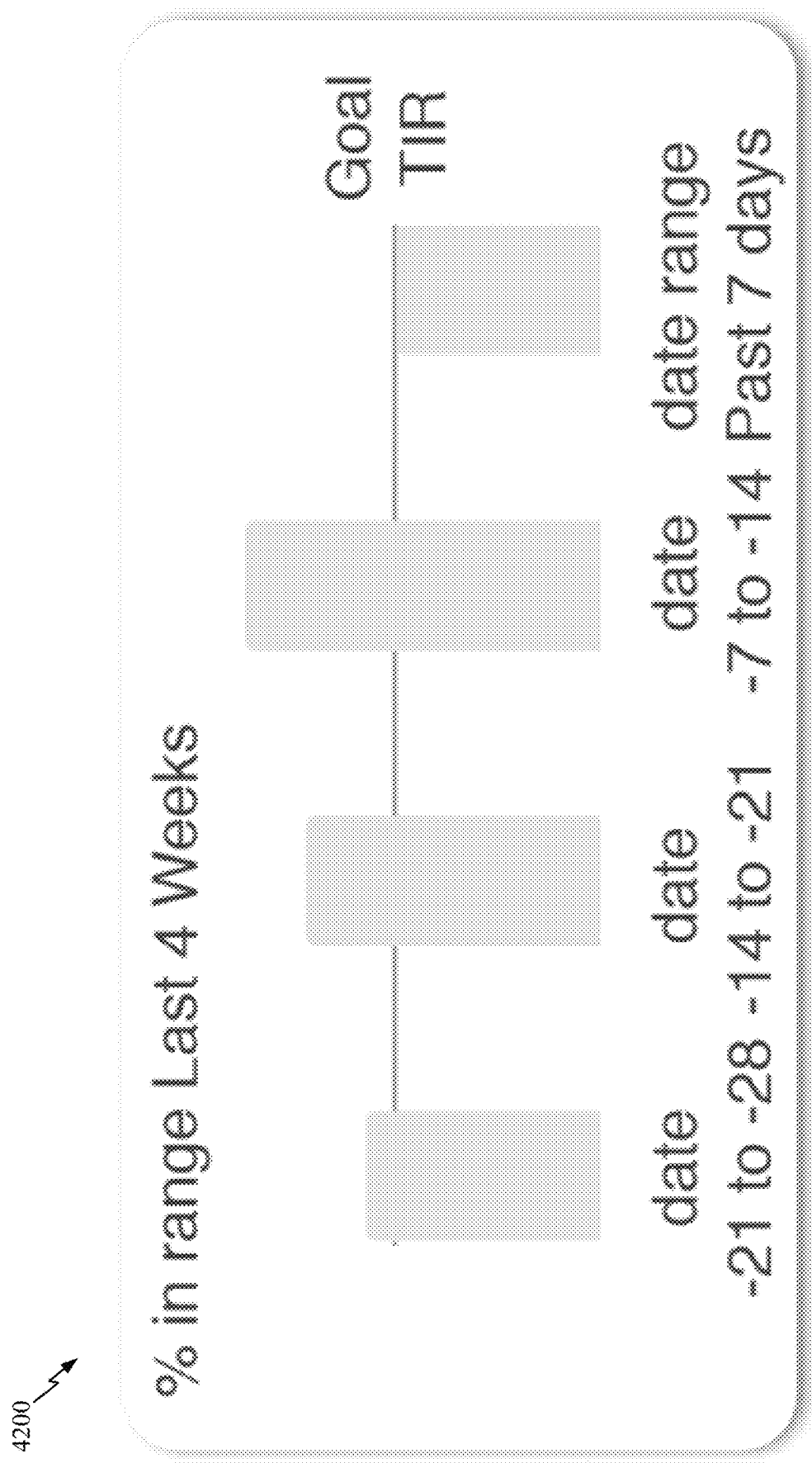
FIG. 42 illustrates another example motivation type widget, in accordance with some example aspects of the present disclosure.

FIG. 42 illustrates another example motivation type widget 4200, in accordance with some example aspects of the present disclosure. As shown in FIG. 42, the motivation type widget 4200 may provide a comparison of a user's percentage of time spent in a target glucose range for a prior defined period of time, such as a prior four week period. The motivation type widget 4200 may also include a comparison of the user's percentage of time spent in the target glucose range for the prior four week period to a goal percentage of time to be spent in the target glucose range per day.

Figure 43:
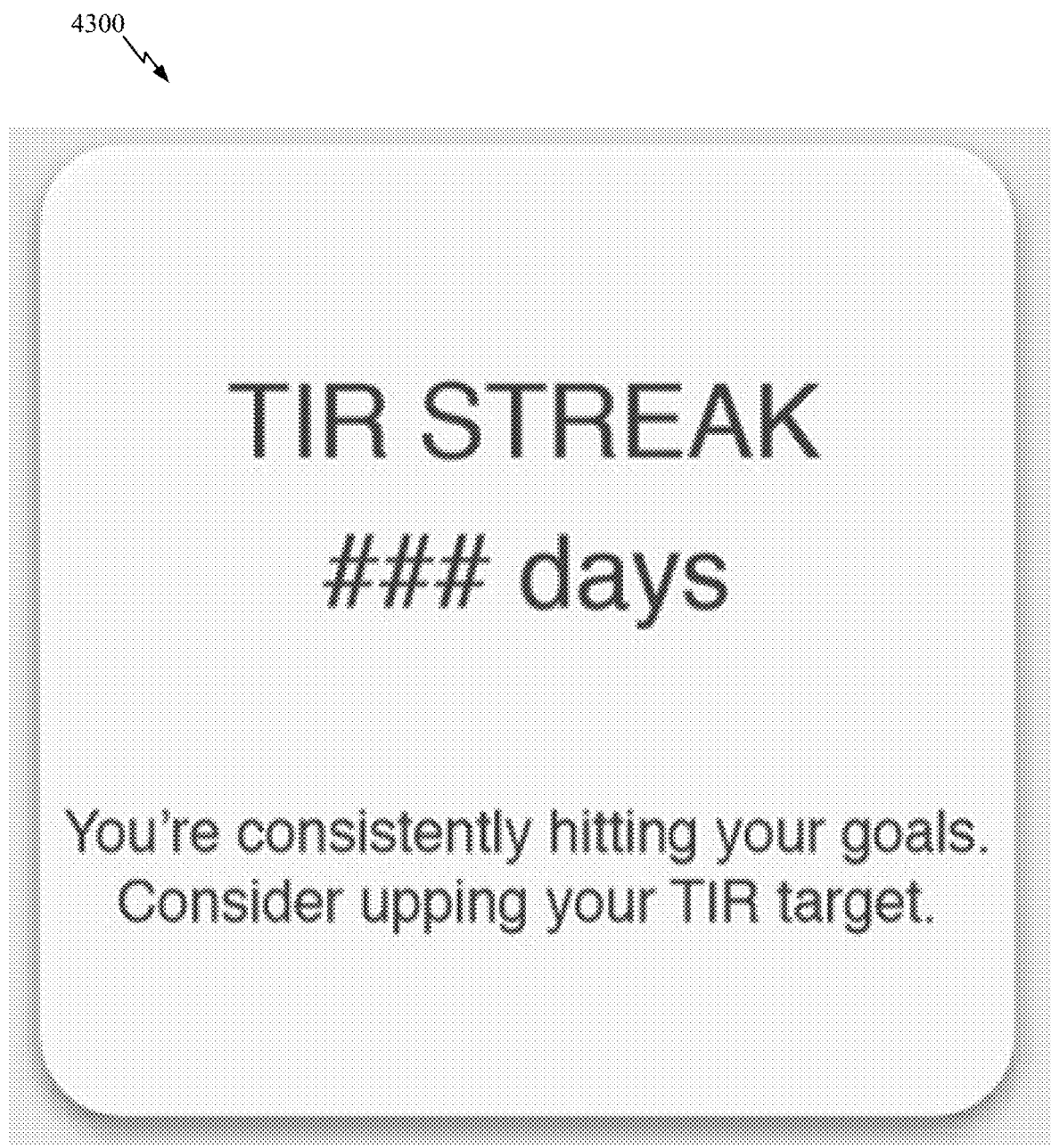
FIG. 43 illustrates a wireframe of another example motivation type widget, in accordance with some example aspects of the present disclosure.

FIG. 43 illustrates another example motivation type widget 4300, in accordance with some example aspects of the present disclosure. As shown in FIG. 43, the motivation type widget 4300 may provide a number of continuous days a user has spent in a target glucose range with a notification to lower or increase the target glucose range. The notification may include a text narrative.

Figure 44:
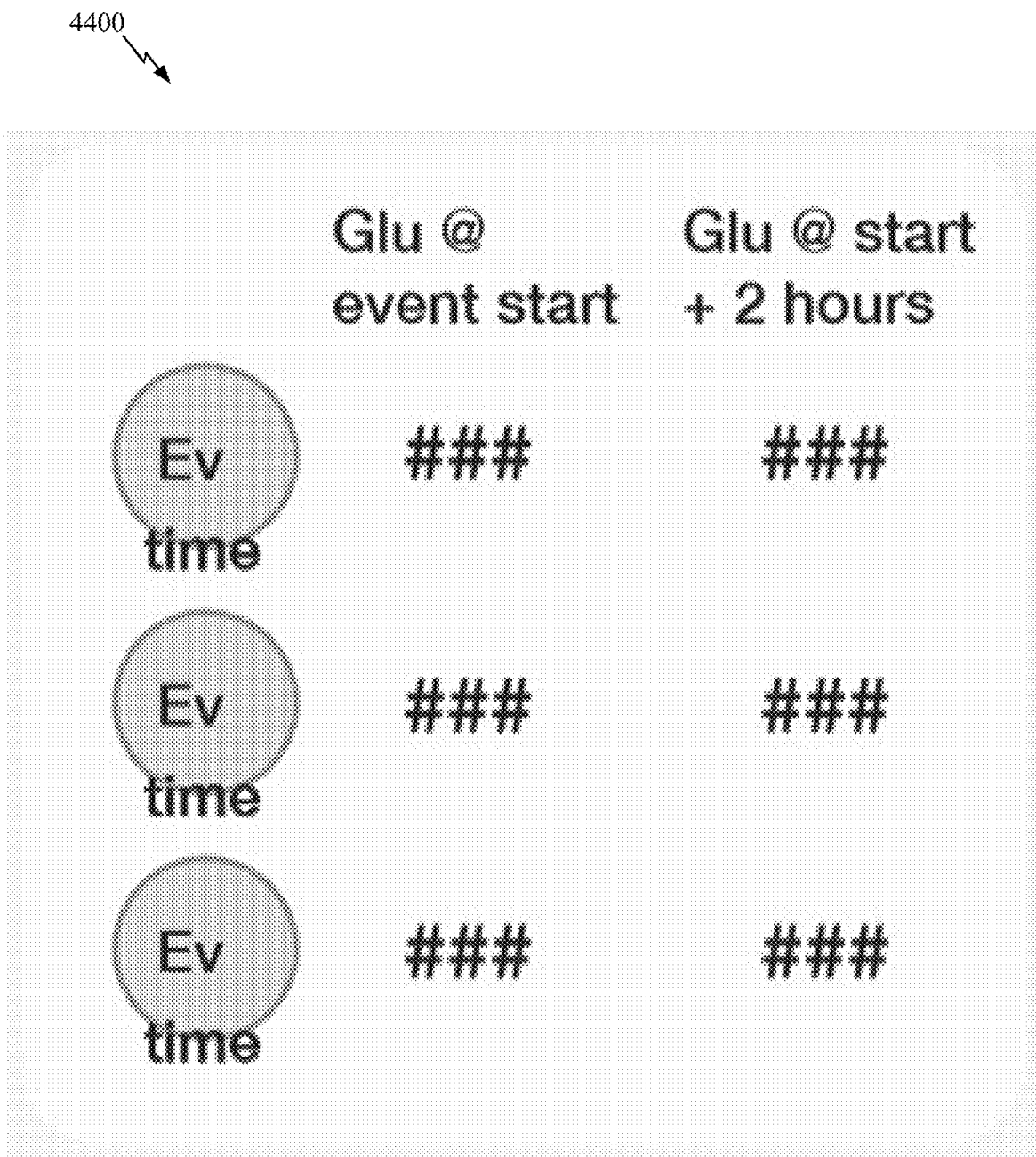
FIG. 44 illustrates a wireframe of an example event type widget, in accordance with some example aspects of the present disclosure.

FIG. 44 illustrates an example event type widget 4400, in accordance with some example aspects of the present disclosure. As shown in FIG. 44, the event type widget 4400 may provide a summary of a user's glucose level at a start of each logged event and the user's glucose level a define period of time, such as two hours, after the start of the logged event.

Figure 45:
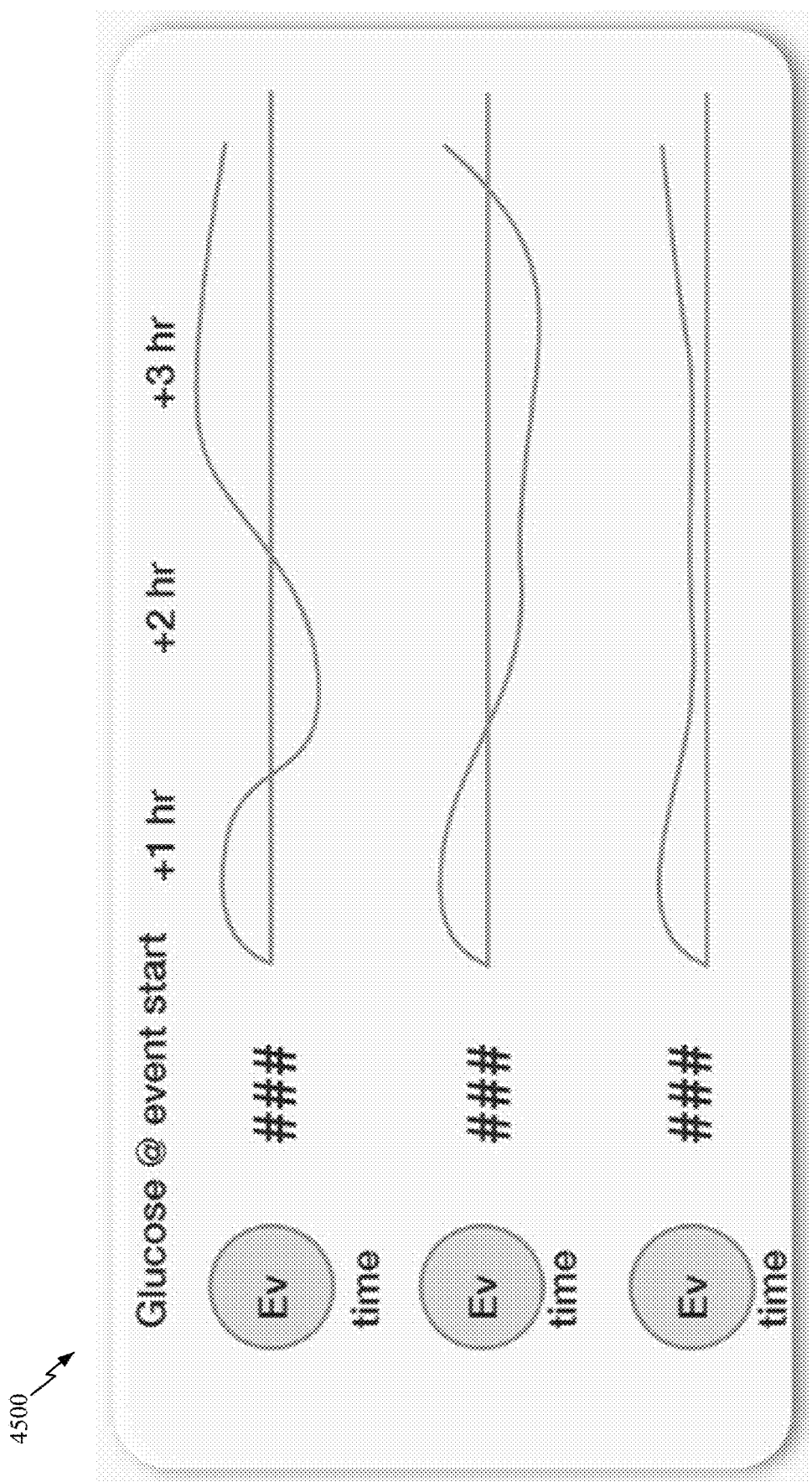
FIG. 45 illustrates a wireframe of another example event type widget, in accordance with some example aspects of the present disclosure.

FIG. 45 illustrates another example event type widget 4500, in accordance with some example aspects of the present disclosure. As shown in FIG. 45, the event type widget 4500 may provide an indication of a user's glucose level at a start of each logged event and a trend of fluctuations in the user's glucose level following each event logged (e.g., one hour after the logged event, two hours after the logged event, three hours after the logged event, etc.).

FIG. 46 illustrates another example event type widget 4600, in accordance with some example aspects of the present disclosure. As shown in FIG. 46, the event type widget 4600 may provide a summary of a user's glucose level per event per day at the start of each logged event, one hour after the start of the logged event, and two hours after the start of the logged event.

Figure 47B:
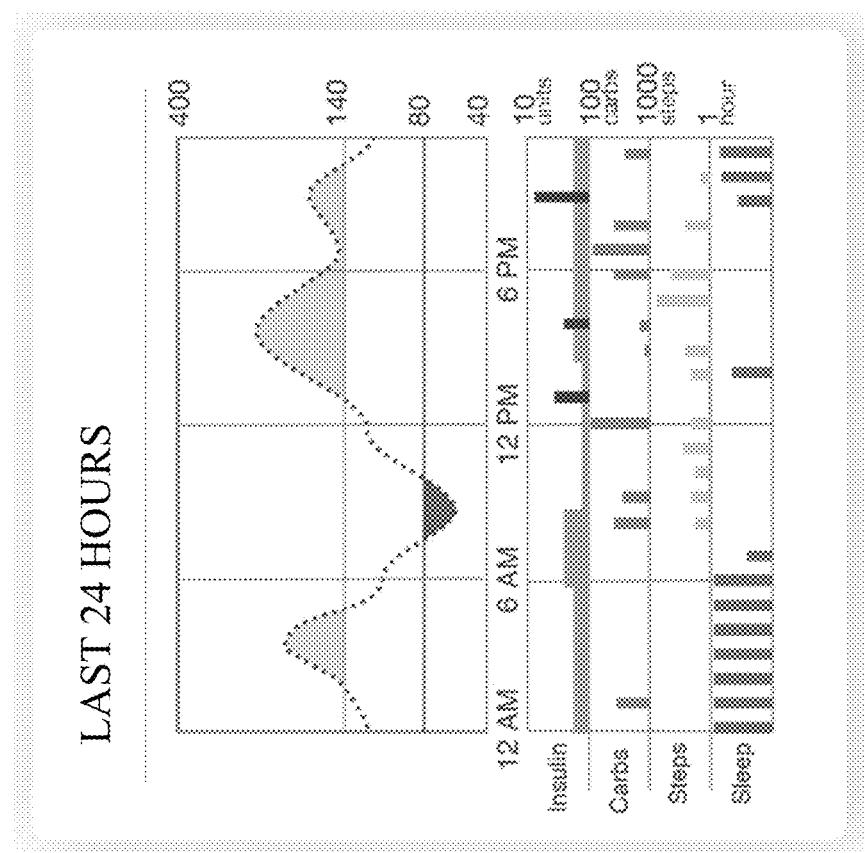
FIGS. 47A and 47B illustrate another example event type widget, and its corresponding wireframe, respectively, in accordance with some example aspects of the present disclosure.
Figure 47A:
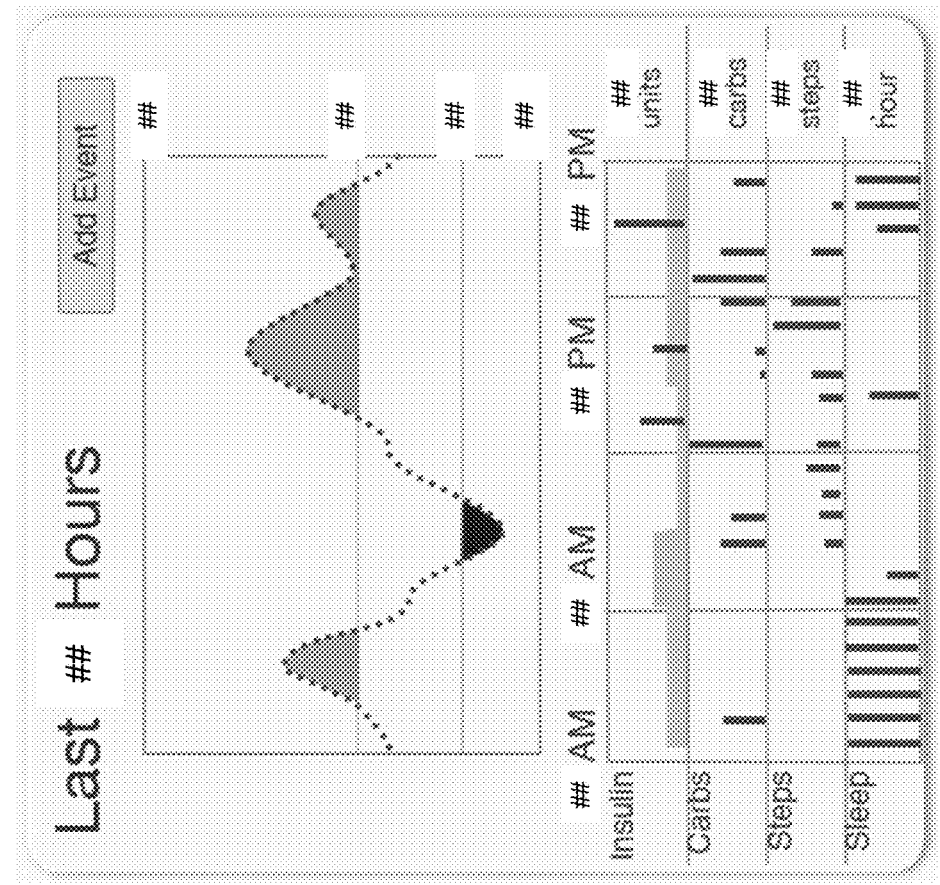

FIGS. 47A and 47B illustrate another example event type widget 4700b, and its corresponding wireframe 4700a, in accordance with some example aspects of the present disclosure. As shown in FIGS. 47A and 47B, the event type widget 4700b may provide trend graphs of a user's glucose levels, insulin units, carbs logged, steps logged, and sleep logged over a specified period (e.g., 24-hour period from 12:00 AM to 12:00 AM). As shown, the trend graphs may be represented as bar graphs in some aspects.

Figure 48:
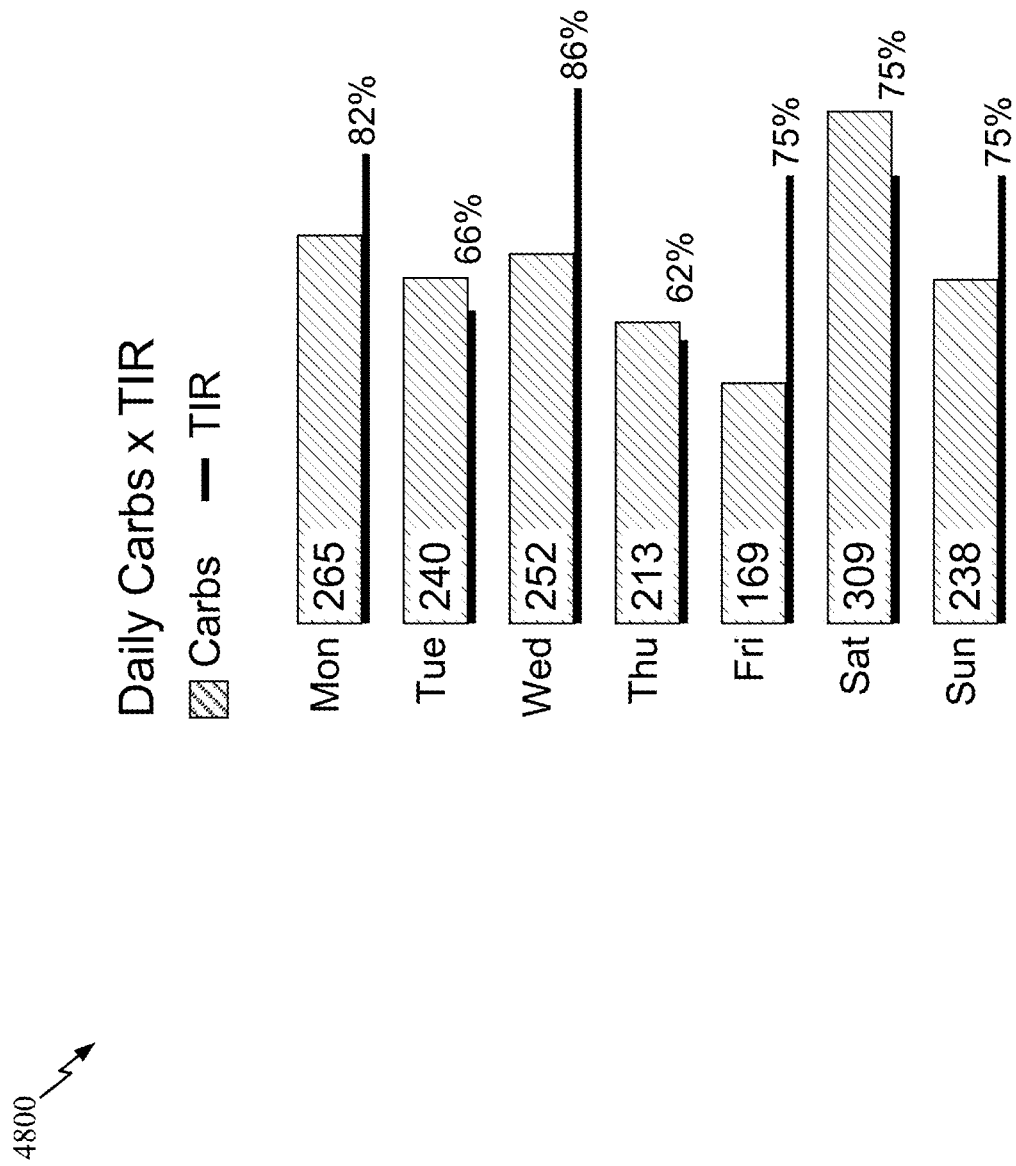
FIG. 48 illustrates another example event type widget, in accordance with some example aspects of the present disclosure.

FIG. 48 illustrates another example event type widget 4800, in accordance with some example aspects of the present disclosure. As shown in FIG. 48, the event type widget 4800 may provide information related to the user's carb intake over a specified period of time. The carb intake information (i.e., calculated based on a user's input of events, including meals logged by the user) may include a day-by-day bar graph of the user's average carb intake and a day-by-day breakdown of the user's percentage of time in a target glucose range (shown as target in range (TIR) in FIG. 48). The TIR percentage illustrated in FIG. 48 represents the percentage of time the user is in a particular glucose range (e.g., a glucose range personalized for the user) for a particular day. Percentage of time in the target glucose range may be provided to assist the user in identifying a correlation, if any, between carb intake and its effect on the user's glucose level.

Figure 49:
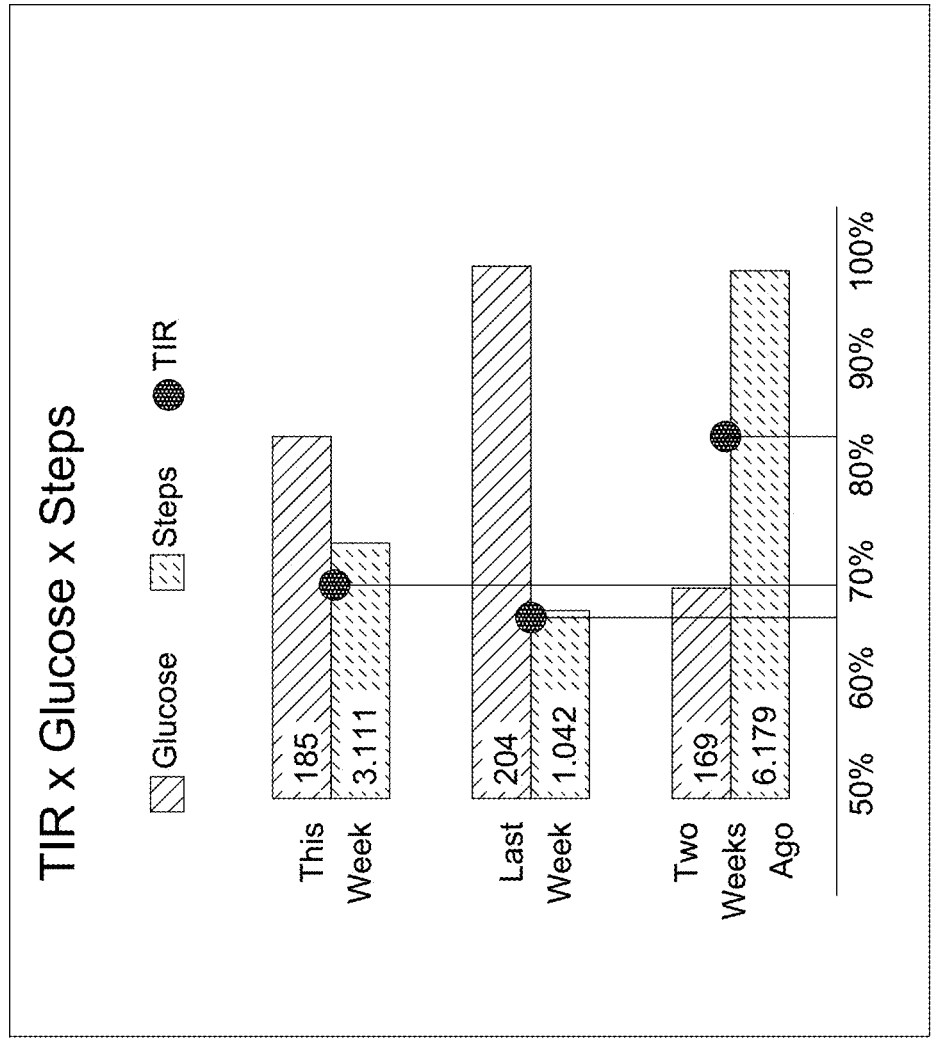
FIG. 49 illustrates another example event type widget, in accordance with some example aspects of the present disclosure.

FIG. 49 illustrates another example event type widget 4900, in accordance with some example aspects of the present disclosure. As shown in FIG. 49, the event type widget 4900 may provide information related to a user's activity over a specified time in combination with glucose levels of the patient. The activity information (i.e., calculated based on a user's input or tracker of events, including steps taken by the user) may include an average number of steps for the current week in comparison to a previous week's average number of steps and the month's average number of steps. The event type widget 4900 may also include a summary of the user's average glucose for the current week in comparison to a previous week's average glucose and the month's average glucose. Further, the event type widget 4900 may also include the user's average percentage of time in a target glucose range for the current week in comparison to a previous week's average percentage of time in the target glucose range and the month's average percentage of time in the target glucose range.

Figure 50:
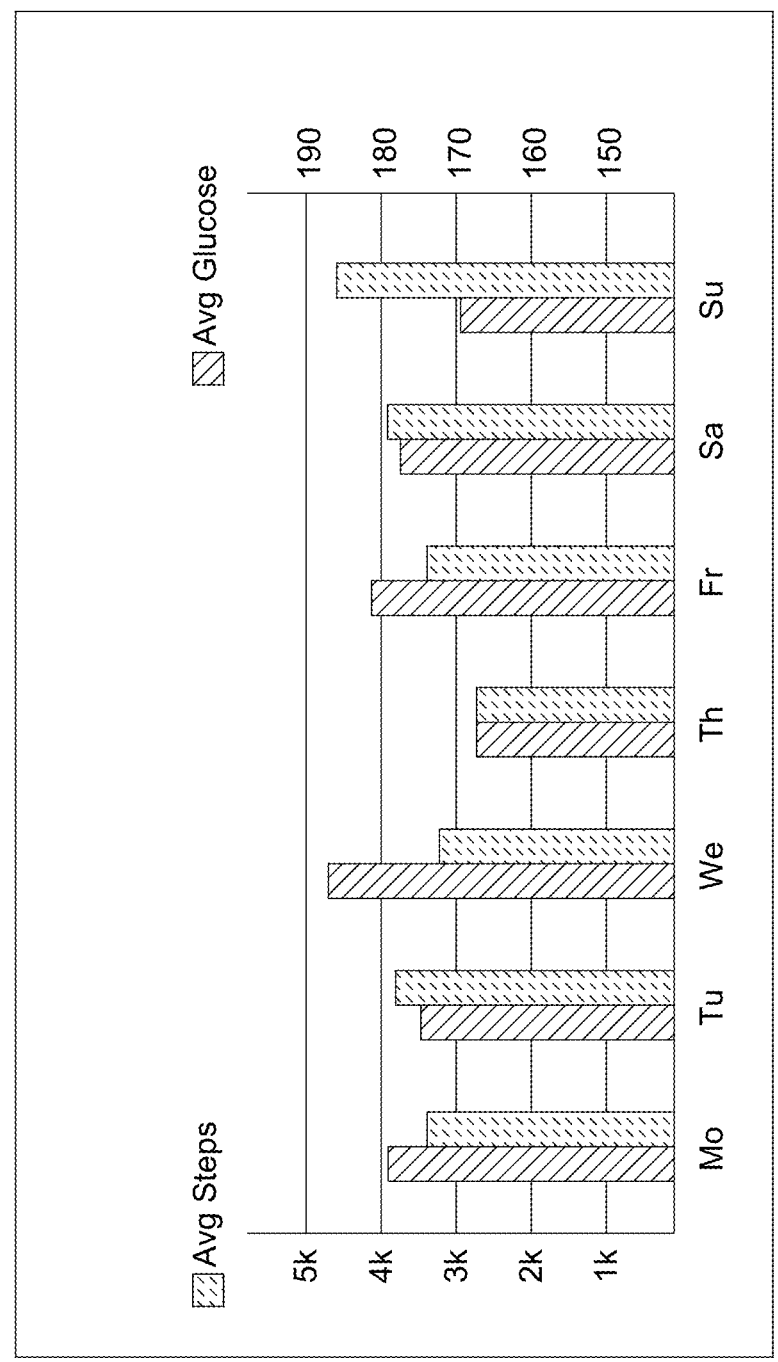
FIG. 50 illustrates another example event type widget, in accordance with some example aspects of the present disclosure.

FIG. 50 illustrates another example event type widget 5000, in accordance with some example aspects of the present disclosure. As shown in FIG. 50, the event type widget 5000 may provide information related to the user's activity over a specified period of time. The activity information may include average steps taken by the user per day. The average steps may be presented in a day-by-day bar graph. The bar graph may also include information about the user's average glucose per day. The comparison may provide insight into activity levels of the patient (e.g., steps taken or not taken) and glucose levels of the user.

Figure 51:
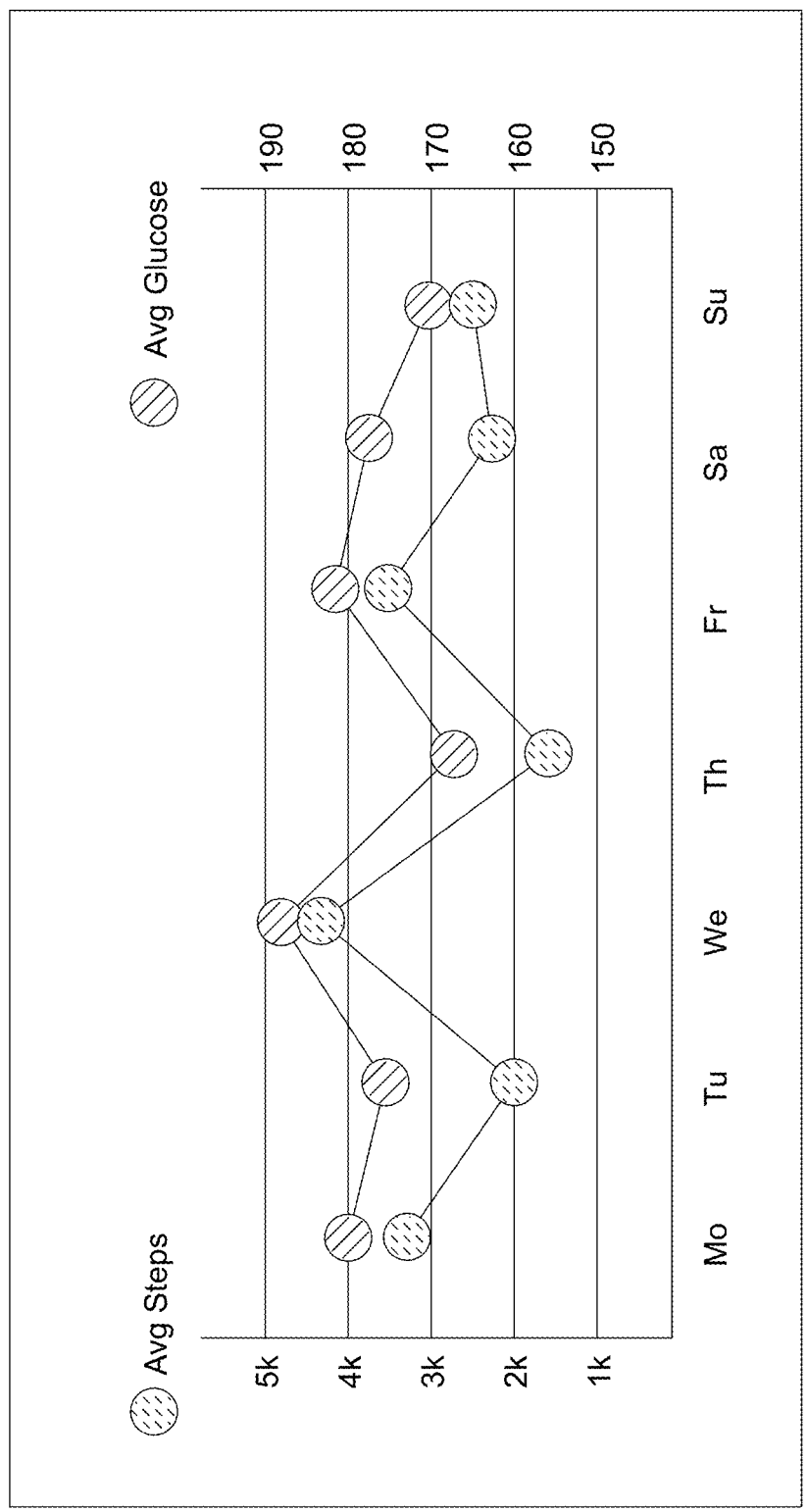
FIG. 51 illustrates another example event type widget, in accordance with some example aspects of the present disclosure.

FIG. 51 illustrates another example event type widget 5100, in accordance with some example aspects of the present disclosure. As shown in FIG. 51, the event type widget 5100 may also provide information related to the user's activity over a specified period of time, similar to the event type widget 5000. However, in the event type widget 5100, the activity information (e.g., the user's steps per day) may be presented in a day-by-day scatter plot as opposed to a day-by-day bar graph. The scatter plot may also include information about the user's average glucose per day. The scatter plot may help to provide a different view to the user of similar information presented in event type widget 5000.

Figure 52:
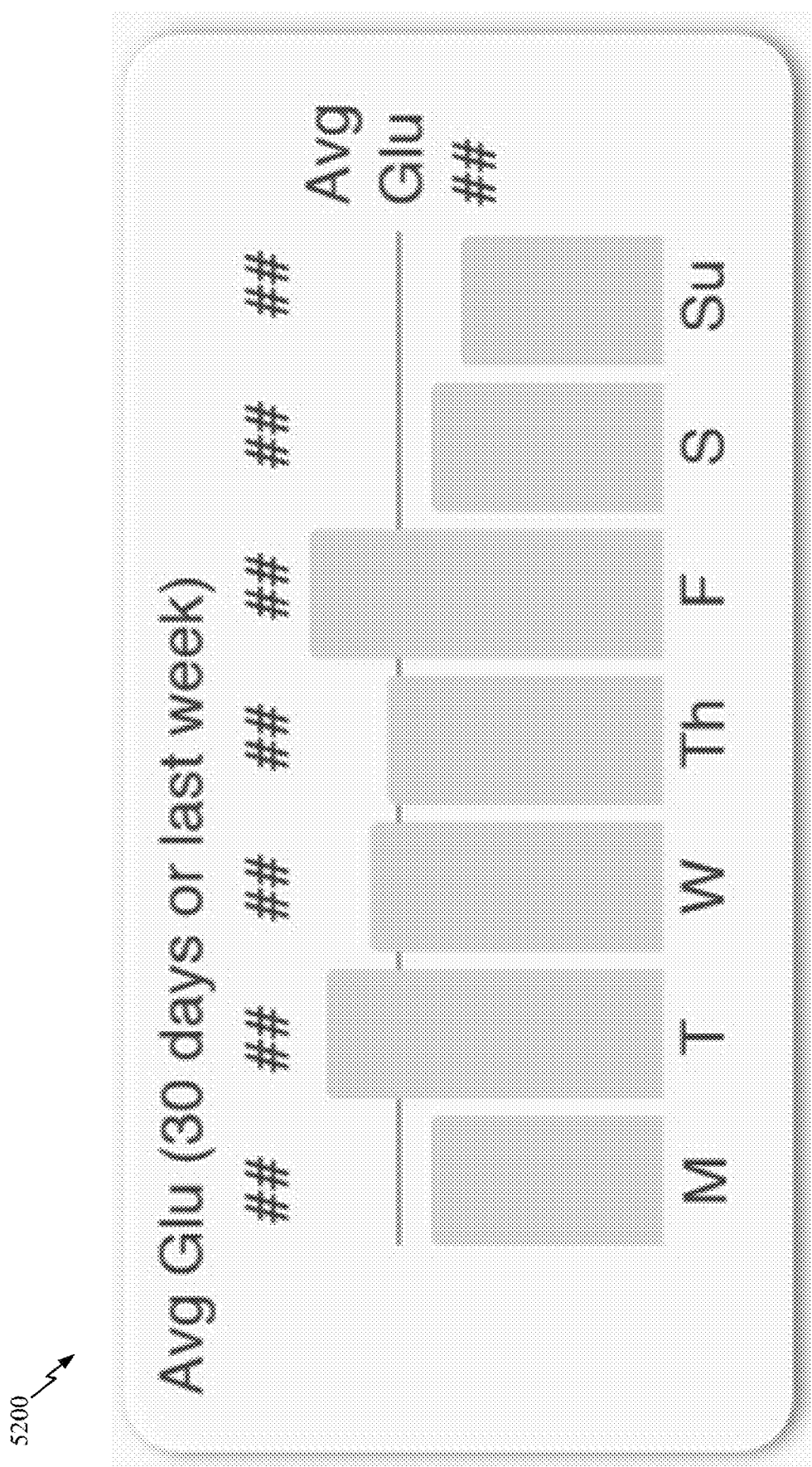
FIG. 52 illustrates a wireframe of an example other type widget, in accordance with some example aspects of the present disclosure.

FIG. 52 illustrates another example type widget 5200, in accordance with some example aspects of the present disclosure. As shown in FIG. 52, the widget 5200 may provide a summary of a user's average glucose for each day of the week over a prior defined period of time, such as the last thirty days (or last week), compared to a goal average glucose per day. As shown, the summary may include both a bar graph and numerical values for average glucose.

Figures 53A, 53B:
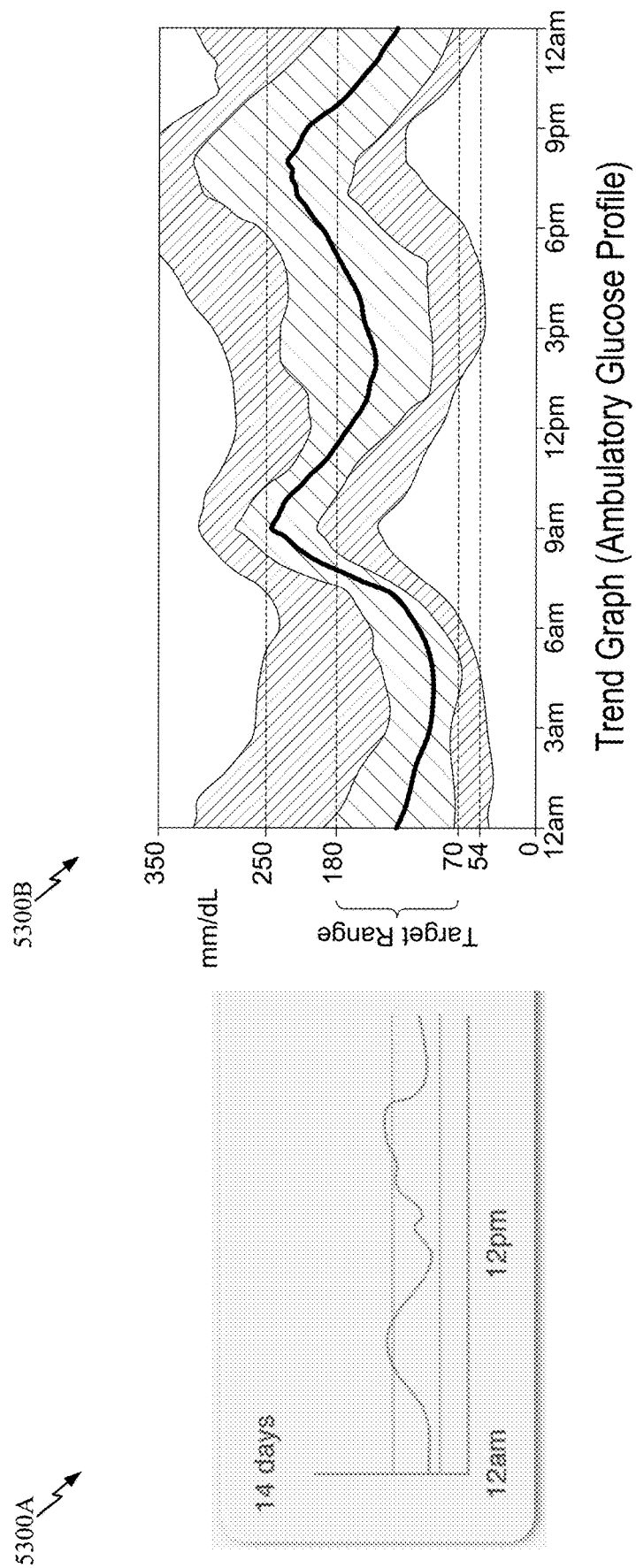
FIGS. 53A and 53B illustrate another example other type widget, and its corresponding wireframe, in accordance with some example aspects of the present disclosure.

FIGS. 53A and 53B illustrate another example type widget 5300b, and its corresponding wireframe 5300a, in accordance with some example aspects of the present disclosure. As shown in FIG. 53B, the widget 5300b may provide a trend of a user's average glucose levels for a defined period of time, such as a twenty-four hour period, over a prior duration of time, such as a prior fourteen day period. In some aspects, the trend graph may also include a box for a "target range" to provide context around average glucose levels measured for the patient, and shown in the trend graph, in comparison to the user's personalized target range.

Figure 54:
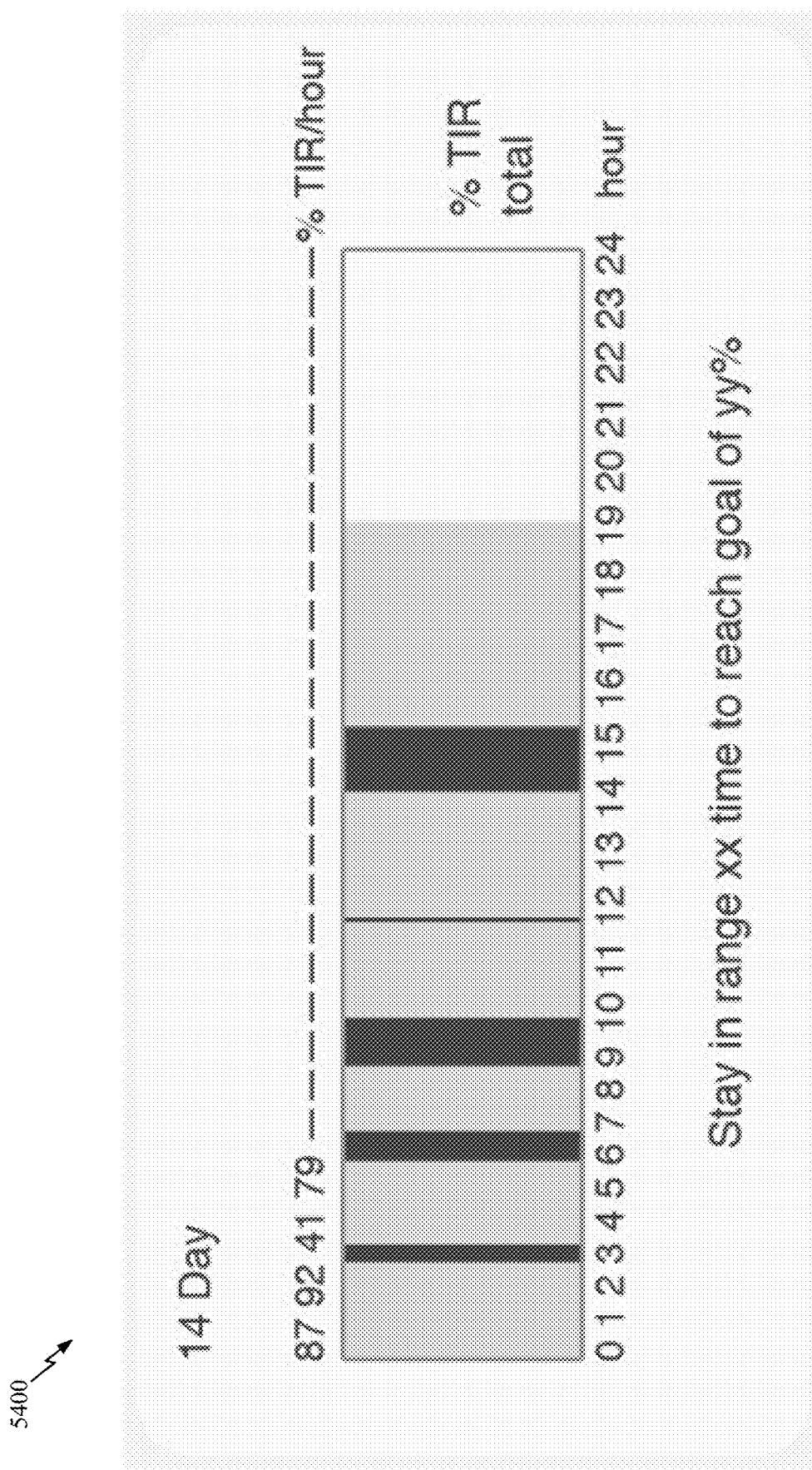
FIG. 54 illustrates another example other type widget, in accordance with some example aspects of the present disclosure.

FIG. 54 illustrates another example type widget 5400, in accordance with some example aspects of the present disclosure. As shown in FIG. 54, the widget 5400 may provide trends of best hours in a defined period of time, such as a twenty-four hour day, over a prior duration of time, such as a fourteen day period, where a user has a highest percentage of time spent in a target glucose range. The widget may also include a notification indicating how much time the user must stay in the target glucose range to reach a goal percentage of time in range. The notification may include a text narrative.

Figure 55:
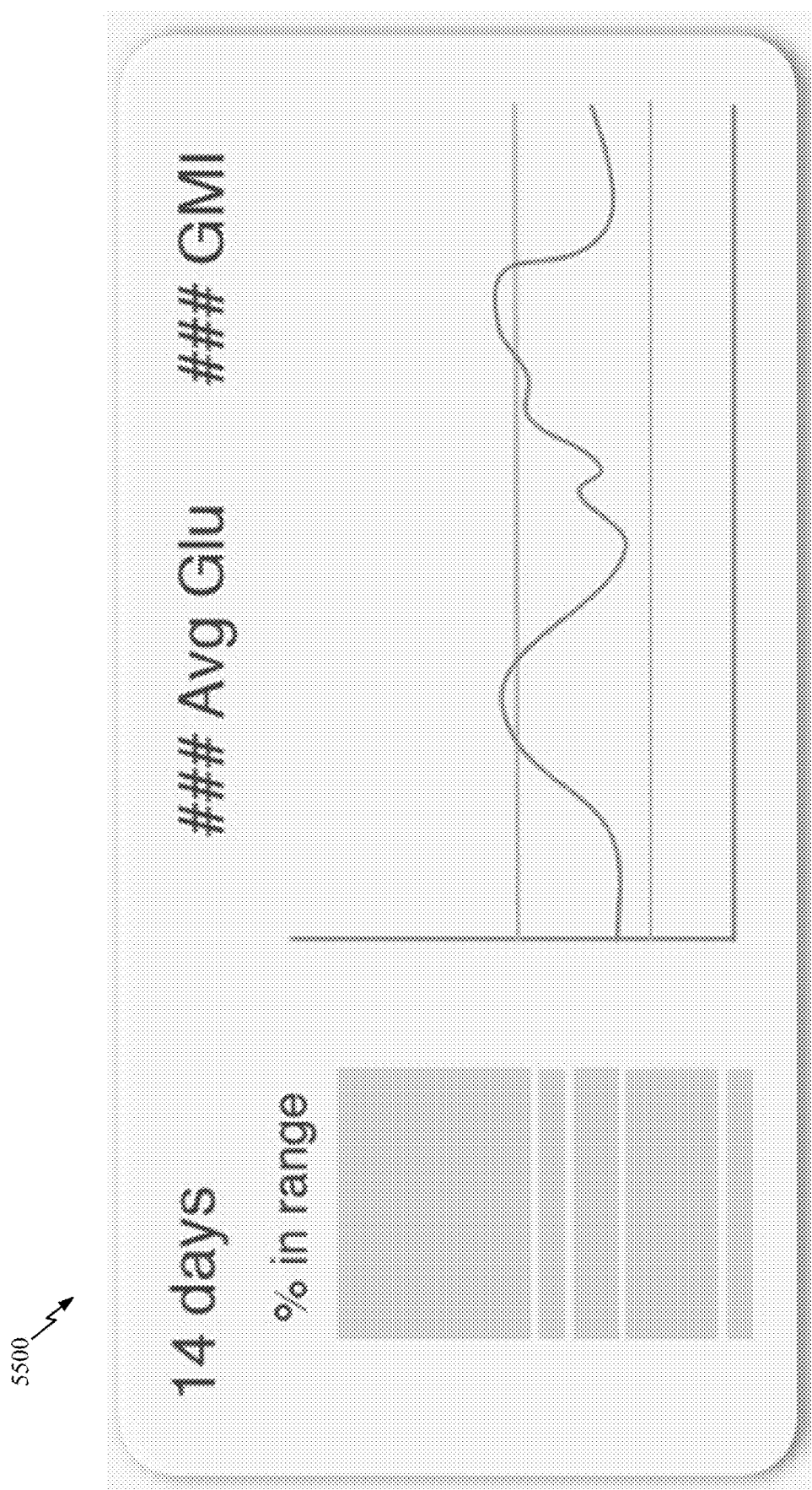
FIG. 55 illustrates a wireframe of another example other type widget, in accordance with some example aspects of the present disclosure.

FIG. 55 illustrates another example type widget 5500, in accordance with some example aspects of the present disclosure. As shown in FIG. 55, the widget 5500 may provide a summary of a user's percentage of time spent in a target glucose range, very high and high glucose ranges, and very low and low glucose ranges over a defined period of time, such as a fourteen day period, the user's average glucose over the defined period of time, and the user's GMI percentage over the defined period of time. The widget 5500 may also include a trend of the user's average glucose levels over a prior similar period of time, such as a prior fourteen day period.

It is to be understood that both the foregoing detailed description is example and explanatory only and is not restrictive. Further features and/or variations of widgets for analyte data visualization may be provided in addition to those set forth above.

According to certain aspects, the widget described herein may be customizable by a user. For example, a user may customize various target values, ranges, and information to be provided on the one or more widgets.

Figure 56:
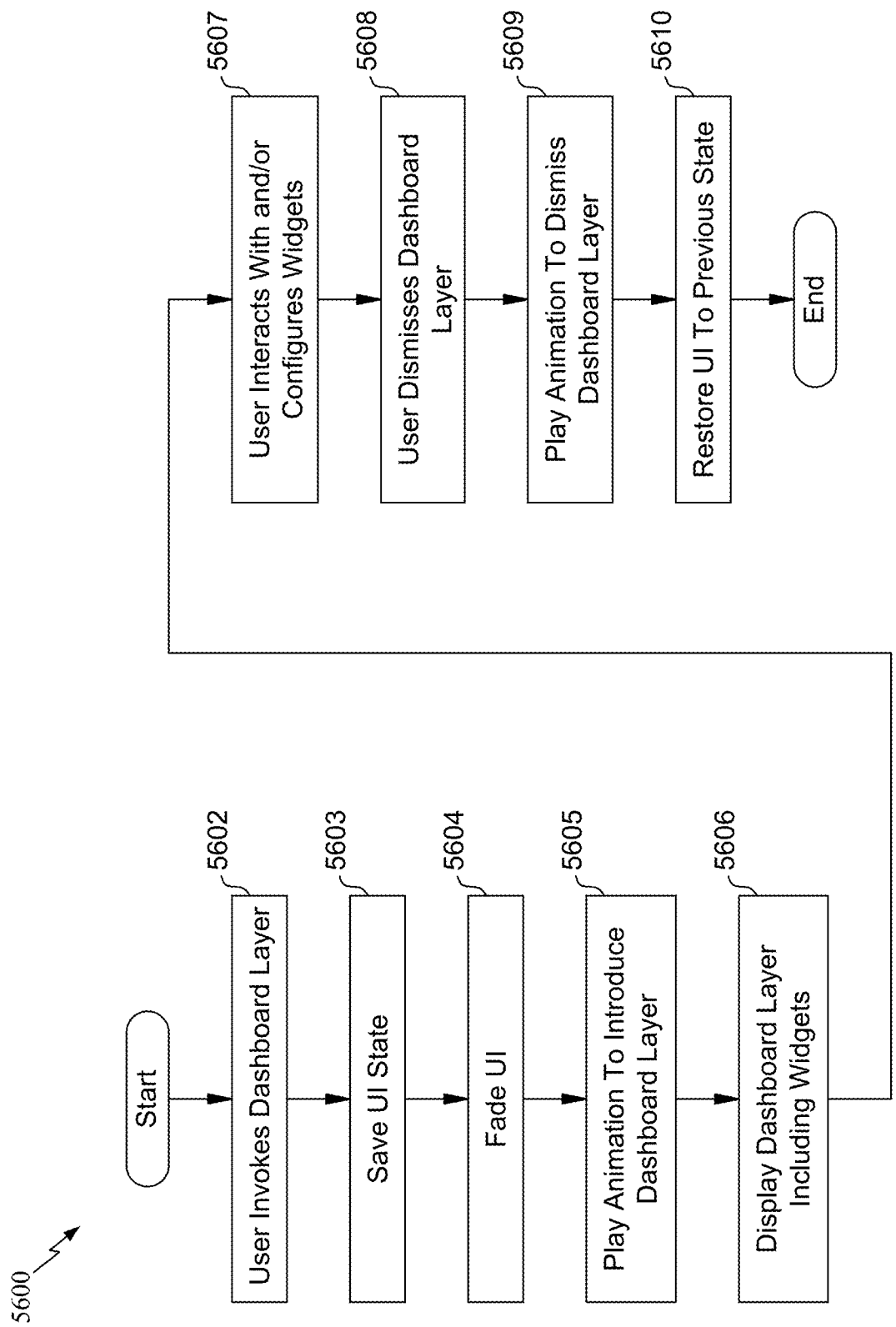
FIG. 56 is a flow diagram illustrating example operations for activating, customizing, and using a dashboard with widgets, in accordance with some example aspects of the present disclosure.

FIG. 56 is a flow diagram illustrating example operations 5600 for activating and using a dashboard with widgets, in accordance with some example aspects of the present disclosure. A dashboard layer (also referred to as a "unified interest layer" or "dashboard") may be used to manage and display widgets. A user may invoke a dashboard, at 5602, in many ways, including by, but not limited to, hitting a designated function key or key combination, clicking on an icon, selecting a command from an onscreen menu, or moving an onscreen cursor to a designated corner of the screen. In response to such user input, the current state of the user interface may be saved, at 5603, the user interface may be temporarily inactivated (e.g., faded), at 5604, an animation or effect may be played or presented to introduce the dashboard, at 5605, and the dashboard may be displayed with one or more widgets, at 5606. Widgets displayed on the dashboard, at 5606, may include one or more of the widgets described previously in FIGS. 19-55.

If applicable, a previous state of the dashboard may be retrieved, so that the dashboard may be displayed in its previous configuration. In some example aspects, the user interface and dashboard may be active at the same time.

At 5607, the user may interact with and/or configure widgets as desired. In some example aspects, the user may move widgets around the screen, and may resize widgets, if applicable. As described previously, some widgets may be resizable and some may have a fixed size. At 5608, the user may dismiss the dashboard by invoking a dismissal command, which may cause the normal user interface to return or re-present itself to the display screen. In some example aspects, the dashboard may be dismissed when the user presses a function key or key combination, clicks on a close box or other icon, clicks on negative space within the dashboard (e.g., a space between widgets), or moves an onscreen cursor to a predefined corner of the screen.

In some example aspects, the dashboard can be automatically dismissed (i.e., without user input) after some predetermined period of time or in response to a trigger event. At 5609, an animation or other effect may be played or presented to provide a transition as the dashboard is dismissed. When the dashboard is dismissed, the current configuration or state of the widgets (e.g., position, size, etc.) may be stored, so that the current configuration or state of the widgets may be retrieved the next time the dashboard is activated. In some example aspects, an animation or effect can be played or presented when re-introducing the user interface. At 5610, the user interface may be restored to its previous state so that the user may resume interaction with software applications and/or the computer operating system.

In some example aspects, the dashboard may be configurable. The user can select a number of widgets to be displayed, for example, by dragging the widgets from a configuration bar (or other user interface element) onto the dashboard. For example, FIG. 57 illustrates an example user interface 5700 that may include various widgets, in accordance with some example aspects of the present disclosure. Widgets selected for display on the dashboard may include one or more of the widgets described previously in FIGS. 19-55.

There are many ways in which dashboards and widgets may be displayed other than those aspects described herein. For example, dashboards and widgets may be displayed on any user interface or user interface element, including but not limited to desktops, browser or application windows, menu systems, trays, multi-touch sensitive displays and other widgets. Additionally, widgets and dashboards may be displayed on any surface capable of displaying widgets and dashboards, such as projections onto surfaces, holograms, surfaces of consumer appliances (e.g., refrigerator doors) and the like.

Additional Considerations

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

While various examples of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various example examples and aspects, it should be understood that the various features and functionality described in one or more of the individual examples are not limited in their applicability to the particular example with which they are described. They instead can be applied, alone or in some combination, to one or more of the other examples of the disclosure, whether or not such examples are described, and whether or not such features are presented as being a part of a described example. Thus the breadth and scope of the present disclosure should not be limited by any of the above-described example examples.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide example instances of the item in discussion, not an exhaustive or limiting list thereof, adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular example of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

The term "comprising as used herein is synonymous with "including," "containing," or "characterized by" and is inclusive or open-ended and does not exclude additional, unrecited elements or method steps.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific examples and examples described herein, but rather to also cover all modification and alternatives coming with the true scope and spirit of the invention.

The invention claimed is:

1. A method for generating a user interface view associated with sensor data representative of analyte levels in a host, comprising:
   receiving sensor data associated with the host in a first time period, the first time period comprising a plurality of analysis time periods of same duration, the sensor data comprising:
   analyte data indicative of analyte levels of the host during the first time period;
   insulin data indicative of insulin intake during the first time period;
   carbohydrate data indicative of carbohydrate intake during the first time period; and
   physical activity data indicative of physical activity levels during the first time period;
   determining a first analysis time period in the first time period during which the host spent a least amount of time in a target analyte range, the first analysis time period comprising a single continuous time period of 24 hours or less;

determining a second time period in the first analysis time during which the host was outside of the target analyte range;

generating a performance report, the performance report comprising:
   a first feature comprising a compilation of first factors contributing to the host spending the least amount of time in the target analyte range, the first factors comprising an average analyte level, an amount of the carbohydrate intake, an amount of the insulin intake, and an amount of physical activity of the host during the first analysis time period; and
   a second feature comprising a second compilation of second factors contributing to the host spending the least amount of time in the target analyte range, the second factors comprising a trend of the analyte levels, a trend of the carbohydrate intake, a trend of the insulin intake, and a trend of the physical activity levels of the host during the first analysis time period, wherein at least one of the first compilation or the second compilation associates the first factors or the second factors with the second time period;

generating a user interface view of the performance report; and providing the user interface view of the performance report for display.

2. The method of claim 1, wherein the performance report further comprises percentages of analyte levels of the host at one or more analyte level ranges during the first analysis time period.

3. The method of claim 1, wherein the performance report further comprises a time spent in at least one of the one or more analyte level ranges during the first analysis time period.

4. The method of claim 3, wherein:
   the one or more analyte level ranges comprises a plurality of analyte level ranges;
   the performance report comprises a time spent in each of the plurality of analyte level ranges; and
   the time spent in each of the plurality of analyte level ranges is represented by a block in a stacked bar graph.

5. The method of claim 4, wherein a color or size of the block in the stacked bar graph corresponds to the time spent in one of the plurality of analyte level ranges.

6. The method of claim 1, wherein the trend of the analyte levels is represented by a scatter plot.

7. The method of claim 1, wherein at least one of the trend of the carbohydrate intake, the trend of the insulin intake, or the trend of the physical activity levels during the first analysis time period is represented by a bar graph.

8. The method of claim 7, wherein the trend of the carbohydrate intake, the trend of the insulin intake, and the trend of the physical activity levels during the first analysis time period are represented by a bar graph broken into multiple stacked data sets to enable comparison of the trend of the carbohydrate intake, the trend of the insulin intake, and the trend of the physical activity levels during the first analysis time period.

9. The method of claim 1, further comprising:
   determining a second analysis time period in the first time period during which the host spent a most amount of time in the target analyte range; and
   determining a third time period in the second analysis time during which the host was within the target analyte range.

10. The method of claim 9, wherein the performance report further comprises:
   an average analyte level and a trend of the analyte levels of the host during the second analysis time period;
   an amount of carbohydrate intake and a trend of the carbohydrate intake during the second analysis time period;
   an amount of insulin intake and a trend of the insulin intake during the second analysis time period; and
   an amount of physical activity and a trend of the physical activity levels during the second analysis time period, and wherein at least one of the average analyte level and the trend of the analyte levels during the second analysis time period, the amount of the carbohydrate intake and the trend of the carbohydrate intake during the second analysis time period, the amount of the insulin intake and the trend of the insulin intake during the second analysis time period, or the amount of the physical activity and the trend of the physical activity levels during the second analysis time period is associated with the third time period.

11. A system for generating a user interface view associated with sensor data representative of analyte levels in a host, comprising:
   at least one memory comprising executable instructions, and
   at least one first processor in data communication with the memory and configured to execute the executable instructions to:
      receive sensor data associated with a host in a first time period, the first time period comprising a plurality of analysis time periods of same duration, the sensor data comprising:
         analyte data indicative of analyte levels of the host during the first time period;
         insulin data indicative of insulin intake during the first time period;
         carbohydrate data indicative of carbohydrate intake during the first time period; and
         physical activity data indicative of physical activity levels during the first time period;
      determine a first analysis time period in the first time period during which the host spent a least amount of time in a target analyte range, the first analysis time period comprising a single continuous time period of 24 hours or less;
      determine a second time period in the first analysis time during which the host was outside of the target analyte range;
      generate a performance report, the performance report comprising:
         a first feature comprising a compilation of first factors contributing to the host spending the least amount of time in the target analyte range, the first factors comprising an average analyte level, an amount of the carbohydrate intake, an amount of the insulin intake, and an amount of physical activity of the host during the first analysis time period; and
         a second feature comprising a second compilation of second factors contributing to the host spending the least amount of time in the target analyte range, the second factors comprising a trend of the analyte levels, a trend of the carbohydrate intake, a trend of the insulin intake, and a trend of the physical activity levels of the host during the first analysis time period, wherein at least one of the first compilation or the second compilation associates the first factors or the second factors with the second time period;

generate a user interface view of the performance report; and provide the user interface view of the performance report for display on a user equipment.

12. The system of claim 11, wherein the performance report further comprises percentages of analyte levels of the host at one or more analyte level ranges during the first analysis time period.

13. The system of claim 11, wherein the performance report further comprises a time spent in at least one of the one or more analyte level ranges during the first analysis time period.

14. The system of claim 13, wherein:
the one or more analyte level ranges comprises a plurality of analyte level ranges;
the performance report comprises a time spent in each of the plurality of analyte level ranges; and
the time spent in each of the plurality of analyte level ranges is represented by a block in a stacked bar graph.

15. The system of claim 14, wherein a color or size of the block in the stacked bar graph corresponds to the time spent in one of the plurality of analyte level ranges.

16. The system of claim 11, wherein the trend of the analyte levels is represented by a scatter plot.

17. The system of claim 11, wherein at least one of the trend of the carbohydrate intake, the trend of the insulin intake, or the trend of the physical activity levels during the first analysis time period is represented by a bar graph.

18. The system of claim 17, wherein the trend of the carbohydrate intake, the trend of the insulin intake, and the trend of the physical activity levels during the first analysis time period are represented by a bar graph broken into multiple stacked data sets to enable comparison of the trend of the carbohydrate intake, the trend of the insulin intake, and the trend of the physical activity levels during the first analysis time period.

19. The system of claim 11, wherein the at least one first processor is further configured to:
determine a second analysis time period in the first time period during which the host spent a most amount of time in the target analyte range.

20. The system of claim 19, wherein the performance report further comprises:
an average analyte level and a trend of the analyte levels of the host during the second analysis time period;
an amount of carbohydrate intake and a trend of the carbohydrate intake during the second analysis time period;
an amount of insulin intake and a trend of the insulin intake during the second analysis time period; and
an amount of physical activity and a trend of the physical activity levels during the second analysis time period.

* * * * *